(12) United States Patent
Sampath et al.

(10) Patent No.: US 11,053,496 B2
(45) Date of Patent: Jul. 6, 2021

(54) CONSEQUENCES OF A DEFECTIVE SWITCH IN CUTANEOUS SQUAMOUS CELL CARCINOMA

(71) Applicant: AGENCY FOR SCIENCE, TECHNOLOGY AND RESEARCH, Singapore (SG)

(72) Inventors: Prabha Sampath, Singapore (SG); Sundaram Gopinath, Singapore (SG); Shan Quah, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/310,395

(22) PCT Filed: Jun. 14, 2017

(86) PCT No.: PCT/SG2017/050302
§ 371 (c)(1),
(2) Date: Dec. 14, 2018

(87) PCT Pub. No.: WO2017/217935
PCT Pub. Date: Dec. 21, 2017

(65) Prior Publication Data
US 2019/0330625 A1    Oct. 31, 2019

(30) Foreign Application Priority Data

Jun. 14, 2016 (SG) .......................... 10201604845W

(51) Int. Cl.
| | | |
|---|---|---|
| *A61K 48/00* | (2006.01) | |
| *C07H 21/04* | (2006.01) | |
| *C12N 15/113* | (2010.01) | |
| *A61P 35/04* | (2006.01) | |
| *A61P 35/00* | (2006.01) | |
| *A61K 31/713* | (2006.01) | |

(52) U.S. Cl.
CPC .......... *C12N 15/113* (2013.01); *A61K 31/713* (2013.01); *A61P 35/00* (2018.01); *A61P 35/04* (2018.01); *C12N 15/1137* (2013.01); *C12N 2310/122* (2013.01); *C12N 2310/14* (2013.01); *C12N 2310/141* (2013.01); *C12N 2310/531* (2013.01); *C12N 2320/31* (2013.01); *C12N 2320/35* (2013.01)

(58) Field of Classification Search
CPC ........................ A61K 31/713; C12N 15/113; C12N 2310/14; C12N 2310/141; C12N 2310/531; C12N 2320/30
See application file for complete search history.

(56) References Cited

U.S. PATENT DOCUMENTS

| | | | |
|---|---|---|---|
| 2009/0326053 A1* | 12/2009 | Walsh ................. | C12Q 1/6883 514/44 R |
| 2011/0306513 A1 | 12/2011 | Song et al. | |
| 2013/0121912 A1 | 5/2013 | Yao et al. | |
| 2019/0194663 A1* | 6/2019 | Yao ..................... | A61K 31/7088 |

FOREIGN PATENT DOCUMENTS

| | | |
|---|---|---|
| CN | 102892898 A | 1/2013 |
| WO | WO2007081720 A2 | 7/2007 |
| WO | WO2010093379 A1 | 8/2010 |
| WO | WO2011088226 A2 | 7/2011 |

OTHER PUBLICATIONS

Mouillet et al. (Placenta, 2015, 36(11), 1231-1238).*
Oshima et al. (Circulation, 2008, 117(24), 3099-3108).*
Wada et al. (Molecular Therapy—Nucleic Acids, 2012, 1, e45).*
Paddison et al. (Methods Mol Biol, 2004, 265, 85-100).*
Bae, et al, "*Mitotic Cell Death Caused by Follistatin-Like 1 Inhibition is Associated With Up-regulated Bim by Inactivated Erk1/2 in Human Lung Cancer*"; Dec. 22, 2015, Oncotarget, vol. 7, No. 14, 9 pages.
Billiar, et al; "*Kupffer Cell and Hepatocyte Interactions*", Journal Of Parenteral (1990), Sage Publications, 7 pages.
Bilzer, et al, "*Role of Kupffer Cells in Host Defense and Liver Disease*" Liver International 2006; 26: 1175-1186, 12 pages.
Blanco-Prieto, et al, "*Serum Calprotectin, CD 26 and EGF to Establish a Panel for the Diagnosis of Lung Cancer*"; Plos One, DOI: 10.1371/journal.pone.0127318 (2015), 17 pages.
Brockhausen, et al; "*miR-181a mediates TGF-β-induced hepatocyte EMT and is dysregulated in cirrhosis and hepatocellular cancer*", Liver International ISSN 1478-3223 (2015), by John Wiley & Sons Ltd; 14 Pages.
Chan, et al; "*Targeting Glioma Stem Cells by Functional Inhibition of a Prosurvival OncomiR-138 in Malignant Gliomas*", Cell Reports 2, 591-602, (2012) 12 pages.

(Continued)

*Primary Examiner* — Amy H Bowman
(74) *Attorney, Agent, or Firm* — Womble Bond Dickinson (US) LLP

(57) ABSTRACT

The present invention refers to a method of treating a carcinoma by administration of one or more of an oligonucleotide comprising the sequence of miR-198 (SEQ ID NO: 1) or a functional part thereof, or an oligonucleotide which reduces expression of Follistatin-related protein 1 (FSTL1), Protein diaphanous homolog 1 (DIAPH1), Laminin subunit gamma-2 (LAMC2) or Urokinase-type plasminogen activator (PLAU). Preferably, the at least one or more oligonucleotides directed against FSTL1, DIAPH1, LAMC2 or PLAU is a shRNA or siRNA. Also provided is a method of determining the presence of carcinoma in a subject, comprising detecting and comparing the presence of miR-198 and/or at least one of FSTL1, DIAPH1, LAMC2 or PLAU, miR-181a, epidermal growth factor (EGF), and epidermal growth factor receptor (EGFR), and comparing the detected levels with that in a control sample.

2 Claims, 35 Drawing Sheets

Specification includes a Sequence Listing.

(56) References Cited

OTHER PUBLICATIONS

Chakraborty, et al., "Gene Expression Profiling of Oral Squamous Cell Carcinoma by Differential Display RT-PCR and Identification of Tumor Biomarkers", Indian Association of Surgical Oncology (2011), 10 pages.
Chatr-Aryamontri, et al, "The BioGRID interaction database 2015 update"; Nucleic Acids Research (2015), vol. 43, 9 pages.
Craig, et al, "Immune Surveillance by the Liver", Nature Immunology vol. 14 No. 10 (2013), 11 pages.
Crispe, et al, "The Liver as a Lymphoid Organ", Anrv371-IY27-06 (2009); 19 pages.
Dang, et al, "Inhibitory Signalling to the Arp2/3 Complex Steers Cell Migration", Nature vol. 503 (2013), 19 pages.
Davis, et al, "Tissue-Resident Macrophages" Europe PMC Funders Group (2013); 23 pages.
Do Canto, et al., "MicroRNA Analysis of Breast Ductal Fluid in Breast Cancer Patients"; International Journal of Oncology 48: 2071-2017 (2016), 8 pages.
Docea, et al., "Immunohistochemical Expression of EGF, c-erbB-2 and EGFR in Intestinal Varian of Gastric Adenocarcinomas", Rom J. Morphol Embryol (2013), 54(3): 545-554; 10 pages.
Duan, et al, "A Straightforward and Highly Efficient Precipitation/On-pellet Digestion Procedure Coupled to a Long Gradient Nano-LC Separation and Orbitrap Mass Spectrometry for Label-free Expression Profiling of the Swine Heart Mitochondrial Proteome", Journal Proteome Res. (Jun. 2009), 27 pages.
Elfimova, et al, "Control of Myogenic and Motogenic Pathways by miR-198, Diminishing Hepatoma Cell Growth and Migration", Biochimica et Biophysica Acta 1833 (2013) 9 pages.
Freedberg, et al, "Keratins and the Keratinocyte Activation Cycle", The Journal of Investigative Dermatology, vol. 116 (May 5, 2001), 8 pages.
Furth, et al, "The Mononuclear Phagocyte System: A New Classification of Macrophages, Monocytes, and their Precursor Cells", Memoranda (1972), 8 pages.
Gaggioli, et al, "Fibroblast-led Collective Invasion of Carcinoma Cells with Differing Roles for RhoGTPases in Leading and Following Cells", Nature Publishing Group (2007), 19 pages.
Garg, et al., "Laminin-5Y-2 Is Highly Expressed in Anaplastic Thyroid Carcinoma and Is Associated With Anaplastic Thyroid Carcinoma and is Associated With Tumor Progression, Migration and Invasion by Modulating Signaling of EGFR", J. Clin Endocrinol Metab (JCEM online) (2014), 99(1):E62-E72; 11 pages.
Griffon, et al, "Activated Macrophages Increase the Susceptibility of Rat Hepatocytes to Ethanol-Induced Oxidative Stress: Conflicting Effects of Nitric Oxide", Nov. 20, 1999, Alcohol & Alcoholism vol. 35, No. 3, pp. 230-235, 6 pages.
Grinchuck, et al, "Sense-Antisense Gene-Pairs in Breast Cancer and Associated Pathological Pathways", Oncotarget, vol. 6 No. 39 (2015), 26 pages.
Hamasaki, et al., "Expression of Laminin 5-Y2 Chain in Cutaneous Squamous Cell Carcinoma and its role in Tumour Invasion", British Journal of Cancer (2011) 105, 824-832; 9 pages.
Han, et al., "Downregulation of Cell-Free miR-198 as a Diagnostic Biomarker for Lung Adenocarcinoma-Associated Malignant Pleural Effusion", International Journal of Cancer: 133, 645-653 (2013), 8 pages.
Hanawa, et al, "EGFR Protein Overexpression and Gene Amplification in Squamous Cell Carcinomas of the Esophagus", Int. J. Cancer: 118, 1173-1180 (2006), 8 pages.
He S., et al., "Has-MicroRNA-1 8 1 a is a Regulator of a Number of Cancer Genes and a Biomarker for Endometrial Carcinoma in Patients: a Bioinformatic and Clinical Study and the Therapeutic Implication", Drug Design, Development and Therapy (2015) 9 1103-1175; 73 pages.
Hendriks, et al, "Isolation, Purification, and Characterization of Liver Cell Types", Methods in Enzymology, vol. 190 (1990), 10 pages.
Ikarashi, et al, "Distinct Development and Functions of Resident and Recruited Liver Kupffer Cells/Macrophages", Journal of Leukocyte Biology vol. 94 (2013), 12 pages.
Isogai, et al, "Initiation of Lamellipodia and Ruffles Involves Cooperation Between mDia 1 and the Arp2/3 Complex", Journal of Cell Science 128, 3796-3810 doi: 10, The Company of Biologist Ltd (2015), 15 pages.
Ito, et al, "Early Hepatic Microvascular Injury in Response to Acetaminophen Toxicity", Microcirculation (2003) 10, 391-400, Nature Publishing Group, 10 pages.
Jiang, et al., "Circulating MicroRNAs as Biomarkers in Hepatocellular Carcinoma Screening: A Validation Set From China", Medicine vol. 94, No. 10 (2015); 10 pages.
Ju, et al, "Protective Role of Kupffer Cells in Acetaminophen-Induced Hepatic Injury in Mice", Chem. Res. Toxicol (2002) 15, 1504-1513, 10 pages.
Karlsson, et al, "Homogeneous Monocytes and Macrophages From Human Embryonic Stem Cells Following Coculture-Free Differentiation in M-CSF and IL-3", Experimental Hematology (2008) 36:1167-1175, 9 pages.
Kim, et al, "Probing Nuclear Pore Complex Architecture with Proximity-Dependent Biotinylation" PNAS (2014), 9 pages.
Kinoshita, et al, "Characterization of two F4/80-Positive Kupffer Cell Subsets by Their Function and Phenotype in Mice" EASL, Journal of Hepatology (2010) vol. 53 903-910, 8 pages.
Kudo-Saito, et al, "Targeting FSTL1 Prevents Tumor Bone Metastasis and Consequent Immune Dysfunction", Cancer Research (2013), 10 pages.
Laskin, et al, "Functional Heterogeneity in Liver and Lung Macrophages" Journal of Leukocyte Biology vol. 70 (2001), 8 pages.
Laskin, et al, "Potential Role of Activated Macrophages in Acetaminophen Hepatotoxicity" Toxicology and Applied Pharmacology 86, 216-226 (1986), 11 pages.
Lin, et al., "Expression of DIAPH1 is Up-Regulated in Colorectal Cancer and Its Down-Regulation Strongly Reduces the Metastatic Capacity of Colon Carcinoma Cells", International Journal of Cancer 134, 1571-1582 (2013), 12 pages.
Lin, et al., "Drosophila Homologue of Diaphanous 1 (DIAPH1) Controls the Metastatic Potential of Colon Cancer Cells by Regulating Microtubule-Dependent Adhesion", Oncotarget, vol. 6, No. 21 (2015), 13 pages.
Linknov, et al., "Early Detection of Head and Neck Cancer: Development of a Novel Screening Tool Using Multiplexed Immunobead-Based Biomarker Profiling", Cancer Epidemiology Biomarkers Prevention (2007); 16(1). 7 pages.
Marin-Muller, et al, "A Tumorigenic Factor Interactome Connected through Tumor Suppressor MicroRNA-198 in Human Pancreatic Cancer" Clinical Cancer Research (2013), 14 pages.
McCawley, et al, "Sustained Activation of the Mitogen-Activated Protein Kinase Pathway; A Mechanism Underlying Receptor Tyrosine Kinase specificity for Matrix Metalloproteinase-9 Induction and Cell Migration", J. Biol. Chem. (1999), pp. 8.
Michael, et al, "Pretreatment of Mice With Macrophage Inactivators Decreases Acetaminophen Hepatotoxicity and the Formation of Reactive Oxygen and Nitrogen Species" Hepatology vol. 30 No. 1 (1999), 10 pages.
Milosevic, et al, "Kupffer Cell-Mediated Differential Down-Regulation of Cytochrome P450 Metabolism in Rat Hepatocytes" EJP 368 (1999) 75-87, 13 pages.
Motakis, et al, "Estimation of Microarray Gene's Prediction Significance by Cox Proportional Hazard Regression Model" IEEE Engineering in Medicine and Biology Magazine (2009), 9 pages.
Movita, et al, "Kupffer Cells Express a Unique Combination of Phenotypic and Functional Characteristics Compared with Splenic and Peritoneal Macrophages", Journal of Leukocyte Biology, vol. 92 (2012), 11 pages.
Nystrom, et al, "Development of a Quantitative Method to Analyse Tumour Cell Invasion in Organotypic Culture", Journal of Pathology (2005); 205: 468-475, 8 pages.

(56) References Cited

OTHER PUBLICATIONS

O-Charoenrat, et al, "*Epidermal Growth Factor-Like Ligands Differentially Up-Regulate Matrix Metalloproteinase 9 in Head and Neck Squamous Carcinoma Cell*" Cancer Research 60, 1121-1128 (2000), 9 pages.

O'Grady, et al, "*Differential Expression of Matrix Metalloproteinase (MMP)-2, MMP-9 and Tissue Inhibitor of Metalloproteinase (TIMP)-1 and TIMP-2 in Non-Melanoma skin Cancer: Implications for Tumour Progression*" Histopathology (2007), 12 pages.

Parker, et al, "*Liver Immunobiology*" Toxicologic Pathology (2005), 11 pages.

Pryczynicz, et al., "*Expression of EGF and EGFR Strongly Correlates with Metastasis of Pancreatic Ductal Carcinoma*", Anticancer Research 28: 1399-1404 (2008), 6 pages.

Pulukuri, et al., "*RNA Interference-Directed Knockdown of Urokinase Plasminogen Activator and u8rokinase Plasminogen Activator Receptor Inhibits Prostate Cancer Cell Invasion, Survival and Tumorigenicity in Vivo*", The Journal of Biological Chemistry vol. 280, No. 43, pp. 36529-36540 (2005), 13 pages.

Ramos-Solano, et al, "*Expression of WNT Genes in Cervical Cancer-Derived Cells: Implication of WNT7A in Cell Proliferation and Migration*" Experimental Cell Research 335 (2015) 39-50, 12 pages.

Rothenberg, et al, "*The Molecular Pathogenesis of Head and Neck Squamous Cell Carcinoma*" The Journal of Clinical Investigation, vol. 122 #6 (2012), 7 pages.

Roux, et al, "*BioID: A Screen for Protein-Protein Interactions*" Curr Protoc Protein Sci. Author Manuscript (2019), 20 pages.

Ruokolainen, et al, "*Expression of Matrix Metalloproteinase-9 in Head and Neck Squamous Cell Carcinoma: A Potential Marker for Prognosis*" Clinical Cancer Research, vol. 10 3110-3116 (2004), 8 pages.

Schafer, et al, "*Cancer as an Overhealing Wound: an Old Hypothesis Revisited*" Nature vol. 9 (2008), Macmillan Publishers Ltd. 11 pages.

Searle, et al, "*Scaffold: A Bioinformatic Tool for Validating MS/MS-Based Proteomic Studies*" Proteomics (2010), 10, 1265-1269, 5 pages.

Sepiashvili, et al., "*Potentially Novel Candidate Biomarkers for Head and Neck Squamous Cell Carcinoma Identified Using and Integrated Cell Line-Based Discovery Strategy*", The American Society for Biochemistry and Molecular Biology, Inc. (2012), 12 pages.

Shalapour, et al, "*Immunity, Inflammation, and Cancer: An Eternal Fight between Good and Evil*" The Journal of Clinical Investigation, vol. 125 #9 (2015). 9 pages.

Sundaram, et al, "*See-Saw Expression of MicroRNA-198 and FSTL1 From a Single Transcript in Wound Healing*", Nature vol. 495 (2013), 6 pages.

Sunman, et al, "*Kupffer Cell-Mediated IL-2 Suppression of CYP3A Activity in Human Hepatocytes*"The American Society for Pharmacology and Experimental Therapeutics vol. 32, No. 3 (2004), 5 pages.

Takezawa, et al, "*Direct Evidence of Macrophage Differentiation from Bone Marrow Cells in the Liver: A Possible Origin of Kupffer Cells*"J. Biochem. 118, 1175-1183 (1995), 9 pages.

Tan, et al, "*miR-198 Inhibits Migration and Invasion of Hepatocellular Carcinoma Cells by Targeting the HGF/c-MET Pathway*" FEBS Letters 585 (2011) 2229-2234, 6 pages.

Tang, et al, "*Meta-Analysis of Transcriptome Reveals Let-7b as an Unfavorable Prognostic Biomarker and Predicts Molecular and Clinical Subclasses in High-Grade Serous Ovarian Carcinoma*" International Journal of Cancer 134, 306-318 (2014), 13 pages.

Tasnim, et al, "*Generation of Mature Kupffer Cells From Human Induced Pluripotent Stem Cells*", Biomaterials 192 (2019) 377-391, 15 pages.

Taylor, et al, "*TGFβ Upregulates miR-181 a Expression to Promote Breast Cancer Metastasis*", The Journal of Clinical Investigation, vol. 123 #1 (2013), 14 pages.

Torres, et al., "*Proteome Profiling of Cancer-Associated Fibroblasts Identifies Novel Proinflammatory Signatures and Prognostic Markers for Colorectal Cancer*", Clin. Cancer Res; 12(21) AACR (2013), 15 pages.

Trabucchi, et al, "*The RNA-Binding Protein KSRP Promotes de Biogenesis of a Subset of miRNAs*", Nature. Author Manuscript (2009), 14 pages.

Troester, et al, "*Activation of Host Wound Responses in Breast Cancer*" Clin. Cancer Res. Author manuscript (2010), 16 pages.

Vollmar, et al, "*The Hepatic Microcirculation: Mechanistic Contributions and Therapeutic Targets in Liver Injury and Repair*", American Physiological Society Rev. 89: 1269-1339 (2009), 71 pages.

Wilgenburg, et al, "*Efficient, Long Term Production of Monocyte-Derived Macrophages from Human Pluripotent Stem Cells Under Partly-Defined and Fully-Defined Conditions*" Plos One vol. 8, Issue 8 (2013), 18 pages.

Winn, et al, "*Antitumorigenic Effect of Wnt 7a and Fzd 9 in Non-Small Cell Lung Cancer Cells Is Mediated Through ERK-5-Dependent Activation of Peroxisome Proliferator-Activated Receptor Y\**" The Journal of Biological Chemistry, vol. 281, No. 37, pp. 26943-26950 (2006), 9 pages.

Winn, e al, "*Restoration of Wnt-7a Expression Reverses Non-small Cell Lung Cancer Cellular Transformation Through Frizzled-9-Mediated Growth Inhibition and Promotion of Cell Differentiation\**" The Journal of Biological Chemistry, vol. 280, No. 20 pp. 19625-19634 (2005), 11 pages.

Wu, et al, "*Suppression of Hepatocyte CYP1A2 Expression by Kupffer Cells Via AhR Pathway: The Central Role of Proinflammatory Cytokines*", International Journal of Molecular Medicine 18: 339-346 (2006); 8 pages.

Yan, et al, "*Squamous Cell Carcinoma—Similarities and Differences Among Anatomical Sites*", Am J Cancer Res 1(3): 275-300 (2011); 26 pages.

Yang, et al, "*MicroRNA-198 Inhibits Proliferation and Induces Apoptosis of Lung Cancer Cells Via Targeting FGFR1*", Journal of Cellular Biochemistry 115: 987-995 (2014); 9 pages.

Yang, et al, "*CLEC4F Is an Inducible C-Type Lectin in F4/80-Positive Cells and Is involved in Alpha-Galactosylceramide Presentation in Liver*," Jun. 6, 2013, PLOS ONE vol. 8, issue 6; 14 pages.

Zuo, et al, "*Activation of EGFR Promotes Squamous Carcinoma SCC20A Cell Migration and Invasion Via Including EMT-Like Phenotype Change and MMP-9-Mediated Degradation of E-Cadherin*", Journal of Cellular Biochemistry 112: 2508-2517 (2011); 10 pages.

Martins et al., "Increased invasive behaviour in cutaneous squamous cell carcinoma with loss of basement-membrane type VII collagen" Journal of Cell Science, May 20, 2009, vol. 122 No. 11, pp. 1788-1799.

Purkis et al., "Antibody markers of basal cells in complex epithelia", Journal of Cell Science, Sep. 1, 1990, vol. 97 No. 1, pp. 39-50.

Wong et al., "Anti-c-Met antibodies recognising a temperature sensitive epitope, inhibit cell growth", Oncotarget, Jun. 29, 2013, vol. 4 No. 7, pp. 1019-1036.

The First Office Action for Chinese Application No. 201780049544.9 dated Nov. 4, 2020, 18 pages.

The International Preliminary Report on Patentability for International Application No. PCT/SG2017/050302 dated Dec. 18, 2018, 10 pages.

Li et al., "Detection and Analysis on MicroRNA Expression Profiles in Tongue Squamous Cell Carcinoma", Chin J Stomatol Res, Dec. 2008, 9 pages, vol. 2, No. 6.

\* cited by examiner a b

A

B

C

D

CONSEQUENCES OF A DEFECTIVE SWITCH IN CUTANEOUS SQUAMOUS CELL CARCINOMA

CROSS-REFERENCE TO RELATED APPLICATIONS

This patent application is a U.S. National Phase Application Under 35 U.S.C. § 371 of International Application No. PCT/SG2017/050302, filed on 14 Jun. 2017, which claims the benefit of priority of Singapore application no. 10201604845W, filed 14 Jun. 2016, the contents of which were incorporated by reference in the entirety for all purposes.

INCORPORATION BY REFERENCE

This patent application incorporates by reference the material (i.e., Sequence Listing) in the ASCII text file named 9322P146 Seq_List.txt, created on Nov. 28, 2018, having a file size of 31,901 bytes, and the content of the ASCII text file of the sequence listing named 9869SG4510 SEQLIST amended 2 7-10 21-22 ST25 6801615 1.txt created on Apr. 13, 2020, having a file size of 32,309 bytes.

FIELD OF THE INVENTION

The present invention generally relates to the field of biochemistry. In particular, the present invention relates to mi-RNAs, anti-miRNAs and polypeptides, which can be used for the treatment of carcinomas.

BACKGROUND OF THE INVENTION

Carcinomas, for example squamous cell carcinomas (SCC), result from the uncontrolled growth of squamous cells, a subtype of epithelial cell. Another example, head and neck squamous cell carcinoma (HNSCC) develops from mucosal linings of the upper aero-digestive tract, mainly in the nasal cavity, paranasal sinuses, nasopharynx, larynx, trachea, oropharynx and oral cavity. Head and neck squamous cell carcinoma (HNSCC) is the sixth highest cancer by incidence worldwide, with 40% to 50% of patients with head and neck squamous cell carcinoma (HNSCC) having a median survival rate of only 5 years. Aggressive disease progression with high rates of metastasis contributes to poor patient survival rates. The identification of therapeutics targeting metastasis in carcinomas is therefore of clinical interest in the management of carcinomas, such as head and neck squamous cell carcinoma (HNSCC). There is thus a need to find a method of targeting and treating cancers, for example epithelial cancers.

SUMMARY

In one aspect, the present invention refers to a method of treating a carcinoma, wherein the method comprises administration of i) one or more of an oligonucleotide comprising or consisting of the sequence of miR-198 (SEQ ID NO: 1), a functional part thereof, or a combination thereof; and/or ii) at least one oligonucleotide which reduces expression of any one or more of the following target proteins: follistatin-related protein 1 (FSTL1), Protein diaphanous homolog 1 (DIAPH1), Laminin subunit gamma-2 (LAMC2) or Urokinase-type plasminogen activator (PLAU).

In another aspect, the present invention refers to a method of determining the presence or absence of a carcinoma in a subject, wherein the method comprises detecting the absence or presence of miR-198 in a sample obtained from a subject; and/or detecting the absence or presence of at least one or more target proteins in the sample; and comparing the detected level of miR-198 with the level of miR-198 detected in a control sample; and/or comparing the detected level of the at least one or more target proteins with the level of the at least one or more target proteins detected in the control sample, wherein the at least one or more target proteins is/are selected from a group consisting of follistatin-related protein 1 (FSTL1), Protein diaphanous homolog 1 (DIAPH1), laminin subunit gamma-2 (LAMC2), urokinase-type plasminogen activator (PLAU) and combinations thereof.

In yet another example, the present invention refers to a method of determining the presence or absence of a carcinoma in a subject, wherein the method comprises a. detecting the absence or presence of miR-198 in a sample; and b. comparing the detected level of miR-198 with the level of miR-198 detected in a control sample; and/or c. detecting the absence or presence of at least one or more biomarkers in the sample; and d. comparing the detected level of the at least one or more biomarkers with the level of the at least one or more biomarkers detected in the control sample; wherein the at least one or more biomarkers is/are selected from a group consisting of miR-181a, epidermal growth factor (EGF) and epidermal growth factor receptor (EGFR) or a combination thereof.

In a further example, the present invention refers to a pharmaceutical composition comprising at least one or more oligonucleotides as disclosed herein.

In one example, the present invention refers to a method of treating a carcinoma, wherein the method comprises administration of one or more oligonucleotides comprising or consisting of the sequence of miR-198 (SEQ ID NO: 1), a functional part thereof, or a combination thereof, in combination with an expression inhibitor of any one of more of the target proteins: follistatin-related protein 1 (FSTL1), Protein diaphanous homolog 1 (DIAPH1), Laminin subunit gamma-2 (LAMC2) or Urokinase-type plasminogen activator (PLAU); wherein the expression inhibitor is selected from the group consisting of siRNA, shRNA and RNAi.

In another example, the present invention refers to a method of treating carcinoma using siRNA and/or shRNA targeting the expression of one or more of the following proteins: follistatin-related protein 1 (FSTL1; SEQ ID NO: 3), Protein diaphanous homolog 1 (DIAPH1; SEQ ID NO: 4), laminin subunit gamma-2 (LAMC2; SEQ ID NO: 5), and urokinase-type plasminogen activator (PLAU; SEQ ID NO: 6):

In yet another example, the present invention refers to use of at least one or more oligonucleotides, as defined herein, in the manufacture of a medicament for treating a carcinoma

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
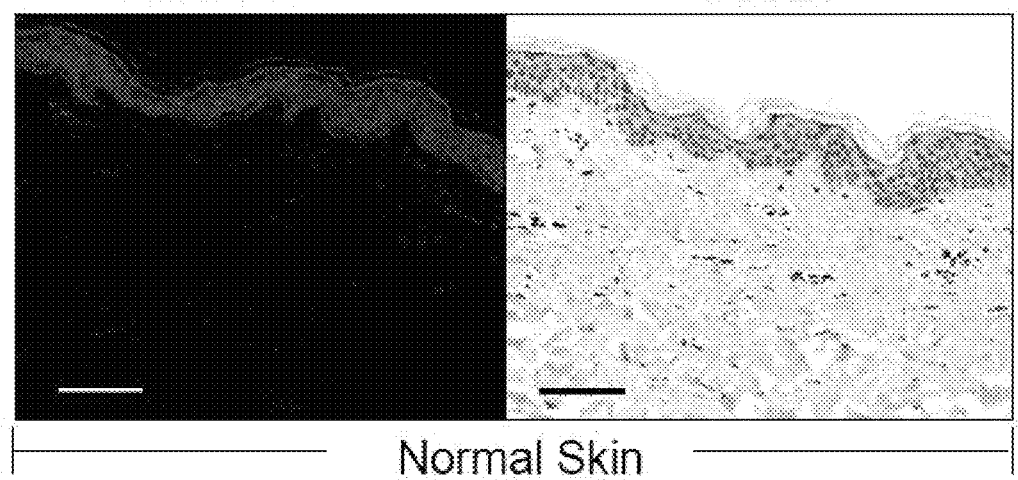
FIG. 1 shows data showing a defective molecular switch in cutaneous SCC. a) shows the results of the expression of miR-198 and FSTL1 protein detected by in situ hybridization (left panel) and immunohistochemistry (right panel) respectively, in normal skin (n=5). b) Expression of miR-198 detected by in situ hybridization (top panel) and immunohistochemical localization of FSTL1 protein (bottom panel) in SCC patient samples (n=73); Scale bar: 100 µM.
Figure 1:
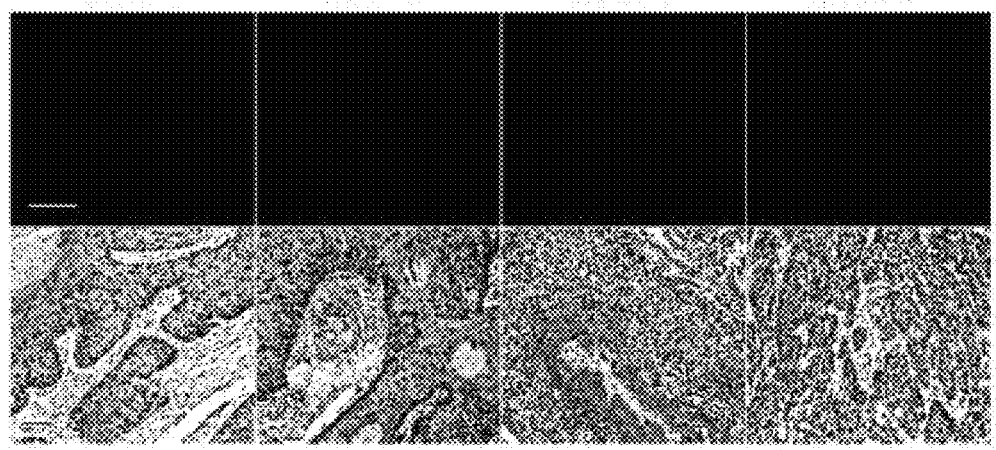

Carcinomas, for example squamous cell carcinomas (SCC), result from the uncontrolled growth of squamous cells, a subtype of epithelial cell. For example, Head and neck squamous cell carcinomas (HNSCC) develop from mucosal linings of the upper aero-digestive tract, mainly in the nasal cavity, paranasal sinuses, nasopharynx, larynx, trachea, oropharynx and oral cavity.

The molecular switch disclosed herein is based on the concept that the status of a cell can have an impact, not only on the expression level of a specific gene, but also on what product is expressed by said gene. By way of an explanation, in on example the gene FSTL1 can produce either the pro-migratory FSTL1 protein, or the anti-migratory miR-198, depending on the state of the cell. It is shown, for example, the carcinoma cells have an increased level of FSTL1 protein, which, in itself is, understood to result in the pro-migratory behaviour of carcinoma cells. Carcinoma-free cells, on the contrary, are understood to express higher levels of miR-198, which contributes to the non-migratory behaviour that is observed in most disease/carcinoma free (in other words, healthy) cells. Therefore, one possible treatment method is to shift a state of a diseased cell into a state akin to a disease-free cell, thereby targeting the regulatory pathways of various targets, for example, but not limited to, any of the target proteins disclosed herein, or RNA targets disclosed herein.

Disclosed herein is a molecular switch, which is essential in wound healing, but is hijacked or mis-regulated in squamous cell carcinoma (SCC). In one example, the cancer is comprised of cells, in which a molecular switch comprises, but is not limited to, the genes and/or nucleic acids involved in wound healing. In one example, the genes are, but are not limited to, genes encoding follistatin-related protein 1 (FSTL1), genes encoding Protein diaphanous homolog 1 (DIAPH1), genes encoding Laminin subunit gamma-2 (LAMC2), genes encoding Urokinase-type plasminogen activator (PLAU) and combinations thereof. In another example, the molecular switch comprises miR-198. In another example, the molecular switch comprises miR-198, and a gene, which is, but is not limited to, follistatin-related protein 1 (FSTL1), Protein diaphanous homolog 1 (DIAPH1), Laminin subunit gamma-2 (LAMC2) or Urokinase-type plasminogen activator (PLAU). In yet another example, the molecular switch comprises the gene follistatin-related protein 1 (FSTL1), and a second gene, which is, but is not limited to, miR-198, Protein diaphanous homolog 1 (DIAPH1), Laminin subunit gamma-2 (LAMC2) or Urokinase-type plasminogen activator (PLAU). In a further example, the molecular switch comprises the gene follistatin-related protein 1 (FSTL1), miR-198 and a third gene, which is, but is not limited to, Protein diaphanous homolog 1 (DIAPH1), Laminin subunit gamma-2 (LAMC2) or Urokinase-type plasminogen activator (PLAU).

The present application shows that rectification of the defective switch results in the reduction of invasive properties of, for example squamous cell carcinoma (SCC), indicating this is a strategy for the treatment of carcinomas. Thus, in one example, disclosed herein is a method of treating a carcinoma, wherein the method comprises administration of at least one or more oligonucleotides and/or at least one or more RNA molecules, wherein the one or more oligonucleotides is homologous in sequence to the nucleic acid sequence of miR-198 or a functional part thereof. In another example, the method is as disclosed herein, wherein the one or more RNA molecules reduce the level of and/or inhibit gene expression of an RNA target of, for example, miR-198. In one example, the one or more RNA molecules are, but are not limited to siRNA (small interfering RNA), shRNA (short hairpin RNA), RNAi (interfering RNA) and combinations thereof. In another example, the one or more RNA molecules are shRNA or siRNA. In yet another example, the siRNA comprises one or more sequences consisting of SEQ ID NO: 7, SEQ ID NO: 8, SEQ ID NO: 9 and SEQ ID NO: 10 and combinations thereof. In another example, the one or more RNA molecules is/are shRNA directed against FSTL1, or a combination of shRNAs which are directed against one or more targets. In another example, the one or more RNA molecules is/are siRNA directed against FSTL1, or a combination of siRNAs which are directed against one or more targets.

As used herein, the term "oligonucleotide" refers to single-stranded or double-stranded nucleic acid polymers. In certain examples, the nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term includes single and double stranded forms of DNA, and single and double stranded forms of RNA. Oligonucleotides may also refer to sense or antisense oligonucleotides, depending on the context in which the term is used.

As used herein, the term "siRNA" refers to a single-stranded RNA molecule, produced by the cleavage and processing of double-stranded RNA. The siRNA can be from 21 to 25 nucleotides in length, but can also be longer or shorter, as there is no convention in the art in regards to the length of siRNA. siRNA bind to complementary sequences in, for example, mRNA or any other RNA targets, and bring about the cleavage and degradation of the target, for example, mRNA. Other functions of siRNAs are for example, their binding to complementary sequences in DNA and bringing about their methylation.

As used herein, the term "shRNA" refers to a short hairpin RNA or small hairpin RNA (shRNA/Hairpin Vector), which is an artificial RNA molecule with a tight hairpin turn that can be used to silence target gene expression via RNA interference. A hairpin turn, also known as a stem-loop, is an intramolecular structure that can occur in oligonucleotides, for example DNA and RNA, and is due to base pairing patterns that occur within the DNA or RNA sequence.

As used herein, the term "RNAi" refers to RNA interference, which is a biological process in which RNA molecules inhibit gene expression or translation, by neutralizing targeted RNA molecules, for example mRNA. Two types of ribonucleic acid (RNAs) are considered to fall under the term RNAi, namely miRNA (microRNA) and siRNA (small interfering RNA).

As used herein, the term "functional", when used in relation to oligonucleotide sequences, refers to the capability of a fragment oligonucleotide to mimic and act in the same manner as the wild type, naturally occurring counterpart. The term "functional" also depends on the function that is to be achieved. For example, when referring to a protein (which also functions as an enzyme) to say that a fragment thereof is functional, that is to say that the peptide fragment functions in the same way as the full-length peptide, in spite of being only a fragment of the full-length peptide.

Also disclosed herein, in one example, is a method of treating a carcinoma, wherein the method comprises administration of one or more oligonucleotides homologous in sequence to the nucleic acid sequence of miR-198 (SEQ ID NO: 1), or a functional part thereof, in combination with an inhibitor of an RNA target of miR-198, wherein the inhibitor is selected from the group consisting of siRNA, shRNA and RNAi, wherein the RNA target is selected from the group consisting of group consisting of follistatin-related protein 1 (FSTL1), Protein diaphanous homolog 1 (DIAPH1), laminin subunit gamma-2 (LAMC2), urokinase-type plasminogen activator (PLAU) and combinations thereof. In other words, disclosed herein is a method of treating a carcinoma, wherein the method comprises administration of A) one or more of an oligonucleotide comprising or consisting of the sequence of miR-198 (SEQ ID NO: 1), a functional part thereof, or a combination thereof; and/or B) at least one oligonucleotide which reduces expression of any one or more of the following target proteins: follistatin-related protein 1 (FSTL1), Protein diaphanous homolog 1 (DIAPH1), Laminin subunit gamma-2 (LAMC2) or Urokinase-type plasminogen activator (PLAU).

In another example, a method of treating carcinoma using siRNA and/or shRNA directed against any part of follistatin-related protein 1 (FSTL1) and/or Protein diaphanous homolog 1 (DIAPH1) and/or laminin subunit gamma-2 (LAMC2) and/or urokinase-type plasminogen activator (PLAU) sequence provided in SEQ ID NOs: 3, 4, 5 and 6, and combinations thereof, is disclosed. In one example, the treatment is directed towards any part of follistatin-related protein 1 (FSTL1). In another example, the treatment is directed towards any part of. In another example, the treatment is directed towards any part of Protein diaphanous homolog 1 (DIAPH1). In another example, the treatment is directed towards any part of laminin subunit gamma-2 (LAMC2). In another example, the treatment is directed towards any part of urokinase-type plasminogen activator (PLAU).

As used herein, the term "modified" refers the alteration of a compound, usually chemically, to add or remove functional groups to or from the chemical structure of the compound. Such a modification usually pertains to the covalent addition of a reagent or a functional group to the compound. Conversely, "unmodified" refers to the fact that a compound has not been chemically altered from the form it which it is most commonly found and/or which is found in nature or under standard conditions. Such modifications are can be found in proteins, and such modifications include, but are not limited to acylation (for example, myristoylation, palmitoylation), isoprenylation or prenylation, glypiation, glycosylphosphatidylinositol (GPI) anchor addition, lipoylation, addition of a flavin moiety (for example, FMN or FAD), addition of a heme group, phosphopantetheinylation, retinylidene Schiff base, glycosylation, fucosylation, alkylation, amidation, amide bond formation, hydroxylation, phosphate ester (O-linked) or phosphoramidate (N-linked) formation, pegylation, biotinylation, carbamylation, oxidation and combinations thereof. In one example, the oligonucleotide is unmodified, or is modified, with one or more chemical groups being one or more of 2'O-methoxy, phosphorothioate, locked nucleic acid and cholesterol.

Without being bound by theory, various methods are encompassed in the present disclosure for targeting and influencing or changing the level of gene expression of target genes. The influence of gene expression, as disclosed herein, can be an increase or decrease in the level of a target gene, for example, or any downstream product of a target gene.

As used herein, the terms "increase" and "decrease" refer to the relative alteration of a chosen trait or characteristic, for example gene expression level or protein levels in a subject, in a subset of a population (for example, of cells) in comparison to the same trait or characteristic as present in the whole population. In one example, the comparison is made between diseased cells and disease-free cells. In other words, the comparison is made between diseased cells and cells from a healthy, disease-free subject. An increase, for example, in expression level, thus indicates a change on a numerically positive scale, whereas a decrease indicates a change on a numerically negative scale. The term "change", as used herein, also refers to the difference between a chosen trait or characteristic of an isolated population subset (for example, a diseased population) in comparison to the same trait or characteristic in the population as a whole, or the same trait or characteristic in a disease-free, healthy population. These terms are used without valuation of the difference seen. Thus, in one example, the control sample is a sample obtained from a carcinoma-free subject.

Also disclosed herein is a method of determining if a subject has a carcinoma, wherein the method comprises providing a sample comprising nucleic acids from a subject and detecting the absence or presence of miR-198; and/or detecting the absence or presence of at least one or more biomarkers in the same sample; and comparing the detected level of miR-198 with the level of miR-198 detected in a control sample; and/or comparing the detected level of the at least one or more biomarkers with the level of the at least one or more biomarkers detected in a control sample. In one example, the at least one or more biomarkers is, but not limited to, of follistatin-related protein 1 (FSTL1), Protein diaphanous homolog 1 (DIAPH1), laminin subunit gamma-2 (LAMC2), urokinase-type plasminogen activator (PLAU) and combinations thereof. In another example, the biomarker is FSTL1.

In another example, method of determining if a subject has a carcinoma, wherein the method comprises providing a first sample comprising nucleic acids from a subject and a. detecting the absence or presence of miR-198 in the first sample; and/or b. comparing the detected level of miR-198 with the level of miR-198 detected in a control sample; and/or providing a second sample comprising tissue from a subject and c. detecting the absence or presence of at least one or more biomarkers in the second sample; and d. comparing the detected level of the at least one or more biomarkers with the level of the at least one or more biomarkers detected in a control sample. In one example, the one or more biomarkers are one or more of the biomarkers as disclosed herein. In another example, the at least one or more biomarkers is, but is not limit to, miR-181a, epidermal growth factor (EGF) and epidermal growth factor receptor (EGFR), or a combination thereof.

In the methods disclosed herein, wherein the absence or the presence of one or more biomarkers is determined, the presence of the carcinoma in question is correlated to the increase or decrease of said biomarker. In one example, the presence of a decreased level of miR-198, compared to the control sample, is indicative of the presence of carcinoma cells. In another example, the presence of an increased level of miR-198, compared to the control sample, is indicative of the absence of carcinoma cells. This effect can also be correlated to other biomarkers, as disclosed herein, which can also be present in the sample. In a further example, the presence of an increased level of at least one or more of the following biomarkers follistatin-related protein 1 (FSTL1), protein diaphanous homolog 1 (DIAPH1), laminin subunit gamma-2 (LAMC2) and urokinase-type plasminogen activator (PLAU), compared to levels of the same one or more biomarkers in a control sample, is indicative of the presence of carcinoma cells in the sample. In another example, the presence or absence of at least two or more of the biomarkers as disclosed herein is required to determine the presence or absence of carcinoma cells. In one example, the presence of an increased level of follistatin-related protein 1 (FSTL1), protein diaphanous homolog 1 (DIAPH1), laminin subunit gamma-2 (LAMC2) and urokinase-type plasminogen activator (PLAU), compared to the control sample, is indicative of the presence of carcinoma cells in the sample. In a further example, the presence of an increased level of FSTL1, compared to a control sample, is indicative of the presence of carcinoma cells in the sample. In one example, the presence of an increased level of miR-181a, EGF and EGFR, compared to a control sample, is indicative of the presence of carcinoma cells in the sample.

In one example, the presence of a decreased level of at least one or more of the following biomarkers follistatin-related protein 1 (FSTL1), protein diaphanous homolog 1 (DIAPH1), laminin subunit gamma-2 (LAMC2) and urokinase-type plasminogen activator (PLAU), compared to levels of the same one or more biomarkers in a control sample, is indicative of the absence of carcinoma cells. In another example, the presence of a decreased level of follistatin-related protein 1 (FSTL1), protein diaphanous homolog 1 (DIAPH1), laminin subunit gamma-2 (LAMC2) and urokinase-type plasminogen activator (PLAU), compared to the control sample, is indicative of the absence of carcinoma cells. In another example, the presence of a decreased level of FSTL1, compared to a control sample, is indicative of the absence of carcinoma cells in the sample. In another example, the presence of a decreased level of miR-181a, EGF and EGFR, compared to a control sample, is indicative of the presence of carcinoma cells in the sample. In another example, at least the presence or absence of FSTL1 and DIAPH1 is used to determine the presence or absence of carcinoma cells. In yet another example, at least the presence or absence of miR-181a, EGF and EGFR are used to determine the presence or absence of carcinoma cells.

Once it is determined, according to any one or more of the methods disclosed herein, whether a carcinoma is present in a subject or not, if a carcinoma is present, the subject can be treated according to the methods of treatment disclosed in the present disclosure. In one example, the method of determining the presence of a carcinoma in a subject is performed as disclosed herein, wherein the subject is subsequently administered i) one or more of an oligonucleotide comprising or consisting of the sequence of miR-198 (SEQ ID NO: 1), a functional part thereof, or a combination thereof; and/or ii) at least one oligonucleotide which reduces expression of any one or more of the following target proteins: follistatin-related protein 1 (FSTL1), Protein diaphanous homolog 1 (DIAPH1), Laminin subunit gamma-2 (LAMC2) or Urokinase-type plasminogen activator (PLAU). In another example, the functional part of miR-198, as referred to above, comprises or consists of 5'GTCCAGAG 3' (SEQ ID NO: 2).

The term "increased" as used herein refers to greater amount, intensity, or degree relative to a control expression level. The increased in expression may be at least about 5%, 10%, 15%, 20%, 25%, 30%, 35%, 40%, 45%, 50%, 55%, 60%, 65%, 70%, 75%, 80%, 85%, 90%, 95% or 100% more than that of a control expression level.

The term "reduced" as used herein refers to decreased amount, intensity, or degree relative to a control expression level. The reduced in expression may be at least about 5%, 10%, 15%, 20%, 25%, 30%, 35%, 40%, 45%, 50%, 55%, 60%, 65%, 70%, 75%, 80%, 85%, 90%, 95% or 100% less than that of a control expression level.

Disclosed herein is a method of treating a carcinoma, wherein the method comprises administration of at least one or more oligonucleotides and/or at least one or more RNA molecules, wherein the one or more oligonucleotides is homologous in sequence to the nucleic acid sequence of miR-198 (SEQ ID NO: 1) or a functional part thereof; wherein the one or more RNA molecules reduce the level of and/or inhibit gene expression of an RNA target of miR-198. Thus, it is also possible and contemplated to target one or more RNA targets or miR-198. These targets can be targeted simultaneously or sequentially. In one example, the RNA target is a gene, which is, but is not limited to, follistatin-related protein 1 (FSTL1), Protein diaphanous homolog 1 (DIAPH1), Laminin subunit gamma-2 (LAMC2) and Urokinase-type plasminogen activator (PLAU), and combinations thereof. In one example, the RNA target expresses a protein with an amino acid sequence selected from a group consisting of SEQ ID NO: 3, SEQ ID NO: 4, SEQ ID NO: 5, and SEQ ID NO: 6 and combinations thereof.

In another example, there is disclosed the use of at least one or more oligonucleotides and/or at least one or more RNA molecules in the manufacture of a medicament for treating a carcinoma. In one example, the one or more oligonucleotides is homologous in sequence to the nucleic acid sequence of miR-198 (SEQ ID NO: 1) or a functional part thereof. In another example, the one or more RNA molecules reduce the level of and/or inhibit gene expression of an RNA target. In yet another example, wherein the RNA target is a gene selected from a group consisting of follistatin-related protein 1 (FSTL1), Protein diaphanous homolog 1 (DIAPH1), Laminin subunit gamma-2 (LAMC2) and Urokinase-type plasminogen activator (PLAU). In a further example, the use of at least one or more oligonucleotides and/or at least one or more RNA molecules in the manufacture of a medicament for treating a carcinoma is disclosed, wherein the one or more oligonucleotides is homologous in sequence to the nucleic acid sequence of miR-198 (SEQ ID NO: 1) or a functional part thereof; and/or wherein the one or more RNA molecules reduce the level of and/or inhibit gene expression of an RNA target; wherein the RNA target is a gene selected from a group consisting of follistatin-related protein 1 (FSTL1), Protein diaphanous homolog 1 (DIAPH1), Laminin subunit gamma-2 (LAMC2) and Urokinase-type plasminogen activator (PLAU). In yet a further example, the use of at least one or more oligonucleotides and/or at least one or more RNA molecules in the manufacture of a medicament for treating a carcinoma is disclosed, wherein the one or more oligonucleotides is homologous in sequence to the nucleic acid sequence of miR-198 (SEQ ID NO: 1) or a functional part thereof; and wherein the one or more RNA molecules reduce the level of and/or inhibit gene expression of an RNA target; wherein the RNA target is a gene selected from a group consisting of follistatin-related protein 1 (FSTL1), Protein diaphanous homolog 1 (DIAPH1), Laminin subunit gamma-2 (LAMC2) and Urokinase-type plasminogen activator (PLAU).

In order for, for example, oligonucleotides to bind and thereby target, or affect, the target gene, the oligonucleotides must possess a sequence similarity to the target gene, as such a binding is understood in the art to be dictated by, for example, complementary binding to the target sequence. In other example, the oligonucleotides mimic the function of the target gene. In such examples, the oligonucleotides would then have sequences that are similar (that is homologous to a defined percentage) or identical (i.e. 100% homologous) to the target sequence. Thus, in one example, the one or more oligonucleotides disclosed herein are about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99% homologous in sequence to the nucleic acid sequence of miR-198 (SEQ ID NO: 1). In another example, the one or more oligonucleotides disclosed herein are between 50% to 99%, between 66% to 77%, between 75% to 99%, between 82% to 99%, between 86% to 95%, between 87% to 93%, or between 95% to 99.9% homologous in sequence to the nucleic acid sequence of miR-198 (SEQ ID NO: 1). In another example, the oligonucleotide has the nucleic acid sequence of miR-198 according to SEQ ID NO: 1, that is the oligonucleotide is 100% homologous to the nucleic acid sequence of miR-198.

In another example, the one or more oligonucleotides disclosed in the present application comprise 5'GGTCCAGAGG GGAGATAGGT TC 3' (SEQ ID NO: 1) or a functional part thereof. In another example, the one or more oligonucleotides comprise 5'GTCCAGAG 3' (SEQ ID NO: 2).

The term "sequence identity", as used herein, refers to the situation where two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

Thus, in one example, the one or more oligonucleotides disclosed herein have about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99% sequence identity to the nucleic acid sequence of miR-198 (SEQ ID NO: 1). In another example, the one or more oligonucleotides disclosed herein have between 50% to 99%, between 66% to 77%, between 75% to 99%, between 82% to 99%, between 86% to 95%, between 87% to 93%, or between 95% to 99.9% sequence identity to the nucleic acid sequence of miR-198. In another example, the oligonucleotide has the nucleic acid sequence of miR-198 according to SEQ ID NO: 1, that is the oligonucleotide has 100% sequence identity to the nucleic acid sequence of miR-198.

The present application identifies a dual-state molecular switch, in which a single transcript can make either an anti-migratory microRNA-198 (miR-198) or the pro-migratory follistatin-like-1 (FSTL1) protein. In normal, that is disease-free, skin, expression of exonic miR-198 switches from FSTL1 mRNA to the pro-migratory FSTL1 protein upon wounding, thereby enhancing temporal migration and orchestrating wound re-epithelialization.

In the present application, a defect in the wound-healing switch is revealed, in which miR-198 expression is shut off in favour of sustained FSTL1 expression. This scenario is shown to be present in cancers, such as for example, head and neck squamous cell carcinomas (HNSCC). An epidermal growth factor (EGF)-driven micro-circuitry hijacks this molecular switch of miR-198 and FSTL1, and then steers the cells towards a two-pronged pathway of metastasis. In the absence of miR-198, persistent expression of its target, DIAPH1, enhances directional persistence of migration by sequestering Arpin, a competitive inhibitor of this migration process. The secreted glycoprotein FSTL1 interacts with Wnt7a and blocks Wnt7a mediated repression of ERK phosphorylation. This allows the phosphorylation of ERK, which in turn stimulates the expression of MMP9, leading to extracellular matrix degradation and the promotion of metastatic behaviour of carcinoma cells, and/or the formation of metastasis of carcinoma cells. This prognostic significance of this exemplary FSTL1-DIAPH1 gene pair in the absence of miR-198 highlights this gene pair as a potential target for therapeutic intervention.

The miR-198/FSTL1 molecular switch had been previously shown to control the context-specific expression of two alternate gene products from a single transcript, thereby regulating wound re-epithelialization. miR-198 is an exonic miRNA and its precursor sequence is located within the 3'-untranslated region of the protein coding follistatin-like-1 (FSTL1) gene. In normal skin, the transcript functions as a primary miRNA, which is processed into mature miR-198, which in turn functions as an inhibitor of keratinocyte migration. However, upon injury, the same transcript functions as a messenger RNA (mRNA) and results in the expression of the FSTL1 protein (follistatin-like-1 protein), which has a pro-migratory effect on cells. This switch from the expression of the anti-migratory miR-198 in normal skin to the pro-migratory FSTL1 expression upon wounding facilitates temporal migration of keratinocytes and wound re-epithelialization.

The proliferation and migration of keratinocytes is essential for, for example, wound healing, but is also a hallmark of all epithelial carcinomas. This process is self-limiting in healing wounds and normally terminates when re-epithelialization is complete. In carcinomas, keratinocyte proliferation and migration is prolonged resulting in uncontrolled growth and metastasis. The parallels between wound healing and epithelial carcinoma in keratinocyte migration and proliferation prompted the investigation of the wound healing switch in the context of progressive head and neck squamous cell carcinomas (HNSCC). A defect was observed in this switch, which resulted in the down-regulation of anti-migratory miR-198, in favour of persistent expression of the pro-migratory FSTL1. In some cases, the expression of pro-migratory targets in head and neck squamous cell carcinomas (HNSCC) were analysed in the absence of miR-198. Persistent, increased expression of DIAPH1, a target of miR-198, together with FSTL1, is shown to enhance migration, invasion and metastasis of carcinoma cells.

Thus, in one example, the target is a gene selected from a group consisting of follistatin-related protein 1 (FSTL1), Protein diaphanous homolog 1 (DIAPH1), Laminin subunit gamma-2 (LAMC2) and Urokinase-type plasminogen activator (PLAU). In another example, the target is an RNA target. In yet another example, the RNA target is a gene selected from a group consisting of follistatin-related protein 1 (FSTL1), Protein diaphanous homolog 1 (DIAPH1), Laminin subunit gamma-2 (LAMC2) and Urokinase-type plasminogen activator (PLAU).

The secreted (glyco-) protein FSTL1 interacts with Wnt7a and antagonises Wnt7a-mediated repression of ERK phosphorylation in head and neck squamous cell carcinomas (HNSCC). This allows the phosphorylation of ERK, which in turn stimulates the expression of matrix metallopeptidase 9 (MMP9), a protein involved in the degradation of the extracellular matrix. Thus, the phosphorylation of MMP9 results in the activation of said MMP9 protein, thereby leading to extracellular matrix degradation and the promotion of metastatic behaviour of carcinoma cells.

DIAPH1 enhances directional persistence of migration by sequestering Arpin, an inhibitor of this process. As a result, Arpin is hindered in its activity and cell migration continues, thereby supporting metastatic behaviour in cancer cells. In summary, the defective molecular switch exerts a double-pronged effect to enhance invasion and metastasis of head and neck squamous cell carcinomas (HNSCC), leading to the progression of the disease.

Epithelial carcinomas activate underlying wound healing program of the host in a prolonged manner to facilitate malignant transformation. Here, a molecular switch was examined at the crossroads of wound healing and squamous cell carcinoma (SCC). This molecular switch controls context-specific expression of two alternate gene products from a single transcript. Investigation of cutaneous squamous cell carcinoma (SCC) samples revealed absence of exonic microRNA-198 (miR-198) however sustained expression of FSTL1 from the linked open reading frame was apparent. In the tumour microenvironment, persistent expression of pro-invasive miR-198 target genes and FSTL1-mediated expression of matrix metalloproteinases (MMP) promote squamous cell carcinoma (SCC) invasion. Expression of human antigen R (HuR) and the EGF-mediated expression of microRNA-181a, which down-regulates KH-type splicing regulatory protein (KSRP), enabled persistent expression of FSTL1. Together, EGF-signalling microcircuit facilitates acquisition of the regulatory switch by cancer cells; prevents processing of tumour suppressor miR-1983 and permits sustained expression of pro-oncogenic factor FSTL1, leading to the progression of SCC.

A novel miR-198/FSTL1 regulatory switch was discovered that is hijacked in cutaneous squamous cell carcinoma (SCC), a common form of skin cancer. The absence of miR-198 and the concomitant, sustained expression of pro-migratory genes FSTL1, as well as miR-198 target genes DIAPH1, LAMC2 and PLAU have been observed in human squamous cancer cell (SCC) samples. It was further demonstrated that knockdown of FSTL1, DIAPH1, LAMC2 and PLAU inhibits keratinocyte invasion (via in vitro transwell and organotypic assays). Moreover, it was also demonstrated that FSTL1 mediates expression of pro-inflammatory genes, the expression of pro-inflammatory genes being a common observation in cancers. The miR-198/FSTL1 regulatory switch is essential for the regulation of keratinocyte migration and wound re-epithelialization in wound healing; pathways which are mis-regulated and overactive in the context of oncogenic transformation in SCC.

To explore parallel molecular mechanisms involved in wound healing and squamous cell carcinomas (SCC), it was sought to investigate the role of a wound healing switch in cancers, for example, in epithelial cancers, such as head and neck squamous cell carcinoma (HNSCC) and cutaneous squamous cell carcinomas. As used herein, the terms "carcinoma" are used interchangeably and refer to a proliferative disease that originates or develops from epithelial cells.

Thus, in one example, the disease disclosed herein is a cancer. In another example, the disease is carcinoma. In another example, the cancer is epithelial carcinoma. In yet another example, the carcinoma originates from cells that are, but are not limited to, cells from the upper aerodigestive tract, mainly in the nasal cavity, paranasal sinuses, nasopharynx, larynx, trachea, oropharynx and oral cavity. In another example, the cells are epithelial cells. In yet another example, the cells are cells of the mucosal lining. In one examples, the disease is, but is not limited to, squamous cell carcinomas (SCC), head and neck squamous cell carcinomas (HNSCC), cutaneous squamous cell carcinomas, basal cell carcinomas (BCC), basal cell neoplasms, melanomas, adenocarcinoma, adenosquamous cell carcinoma, transitional cell carcinoma, anaplastic carcinoma, large cell carcinoma, small cell carcinoma, cholangiocarcinoma, hepatocellular carcinoma, adenoid cystic carcinoma, renal cell carcinoma, Grawitz tumour, adnexal and Skin appendage neoplasms, mucoepidermoid neoplasms, cystic neoplasms, mucinous neoplasms, serous neoplasms, ductal neoplasms, lobular neoplasms, medullary neoplasms, acinar cell neoplasms, complex epithelial neoplasms, cholangiocarcinoma and carcinoma of unknown origins. In one example, the carcinoma is a squamous cell carcinoma (SCC). In another example, the carcinoma is cutaneous squamous cell carcinoma. In another example, the carcinoma is head and neck squamous cell carcinomas (HNSCC). As appreciated by a person skilled in the art, in the field of carcinomas, the location of a carcinoma is one of the defining traits in the characterisation of the carcinoma. For example, a carcinoma found in the thyroid is considered to be a thyroid carcinoma. Further characterisation is performed based on the morphology of the diseased cells, that is comparison of the shape of the diseased cells themselves and of the cells in a disease-free state. For example, a squamous cell thyroid carcinoma is a rare malignant neoplasm of the thyroid gland, which shows tumour cells with distinct squamous differentiation. Having said that, squamous cells are not usually found in the thyroid glands, but may be derived from the embryonic remnants such as thyroglossal duct or branchial clefts.

The present invention also discloses methods for the diagnosis and treatment of epithelial carcinoma, such as squamous cell carcinoma (SCC) and head and neck squamous cell cancer (HNSCC). In one example, there is disclosed a method or use of miR-198 and/or a further biomarker in the diagnosis of epithelial carcinoma. In another example, there is disclosed a method or use of oligonucleotide mimics of miR-198, or miR-198 itself, in the treatment of epithelial carcinoma. In yet another example, there is disclosed a method or use of siRNAs against FSTL1, DIAPH1, LAMC2, PLAU or combinatorial siRNAs in the treatment of epithelial carcinoma. In one example, the epithelial carcinoma is squamous cell carcinoma (SCC). In another example, the epithelial cancer is cutaneous squamous cell carcinoma (SCC). In another example, the epithelial carcinoma is head and neck squamous cell carcinoma (SCC).

The present disclosure also relates to the absence of miR-198 expression and/or the presence of FSTL1 expression as biomarkers for the diagnosis of a carcinoma. In one example, the carcinoma is cutaneous squamous cell carcinoma (SCC). In addition, miR-198 and its downstream targets, DIAPH1, LAMC2 and PLAU are also considered therapeutic targets for the treatment of carcinomas, for example cutaneous squamous cell carcinoma (SCC).

It was shown that cutaneous squamous cell carcinoma (SCC) cells show a specific and robust expression of FSTL1 and concomitant low (negligible) levels of miR-198, compared to normal skin samples. It was also demonstrated that knockdown of FSTL1, as well as miR-198 target genes (DIAPH1, LAMC2 and PLAU), resulted in a reduction in the invasiveness of cutaneous squamous cell carcinoma (SCC) cell lines. This data points to the fact that a defective miR-198/FSTL1 switch is present in cutaneous squamous cell carcinoma (SCC) and that restoring normal function of this switch provided an innovative strategy for the treatment of SCC.

miR-198/FSTL1 can be used effectively as a biomarker in the diagnosis of cutaneous squamous cell carcinoma (SCC), as it was demonstrated that miR-198 is highly expressed in normal skin epidermis and lowly expressed in all cutaneous squamous cell carcinoma (SCC) tissue sections assayed (n=73). Conversely, FSTL1 is present in high levels in cutaneous squamous cell carcinoma (SCC) tissue sections (n=73) and negligible levels in normal tissue.

Cutaneous squamous cell carcinoma (SCC) is the second most common skin cancer and is a primary malignancy, characterized by significant cell atypia, abnormal keratinization and invasive features. Cutaneous squamous cell carcinoma (SCC) shares the features of basal cell carcinoma (BCC) and melanoma, being locally invasive with a capacity to metastasize. Malignant transformation is considered as a severe complication of non-healing ulcer wounds. Also, epithelial tumours promote formation of their stroma by activating an uncontrolled wound healing response. In an attempt to explore the common molecular mechanisms in re-epithelialization phase of wound healing and the parallels to cutaneous squamous cell carcinoma (SCC), the miR-198/FSTL1 regulatory switch, which controls context-specific expression of two alternate gene products and serves as an orchestrator of wound re-epithelialization, was analysed. At steady state, healthy epidermal keratinocytes express high levels of exonic miR-198, but no FSTL1 protein (FIG. 1a). On the contrary, similar to wound microenvironment, migrating and proliferating keratinocytes in cutaneous squamous cell carcinoma (SCC) tissue sections express high levels of FSTL1, and very little or no miR-198 (FIG. 1b). Together, and without being bound by theory, this supports the hypothesis that tumours are over-healing wounds and strengthens the link between wound healing and carcinoma. However, persistent expression of pro-migratory FSTL1 and the absence of anti-migratory miR-198 suggest that cancer cells potentially exploit the molecular switch to enhance migration and invasion of cutaneous squamous cell carcinoma (SCC) cells.

Figure 2:
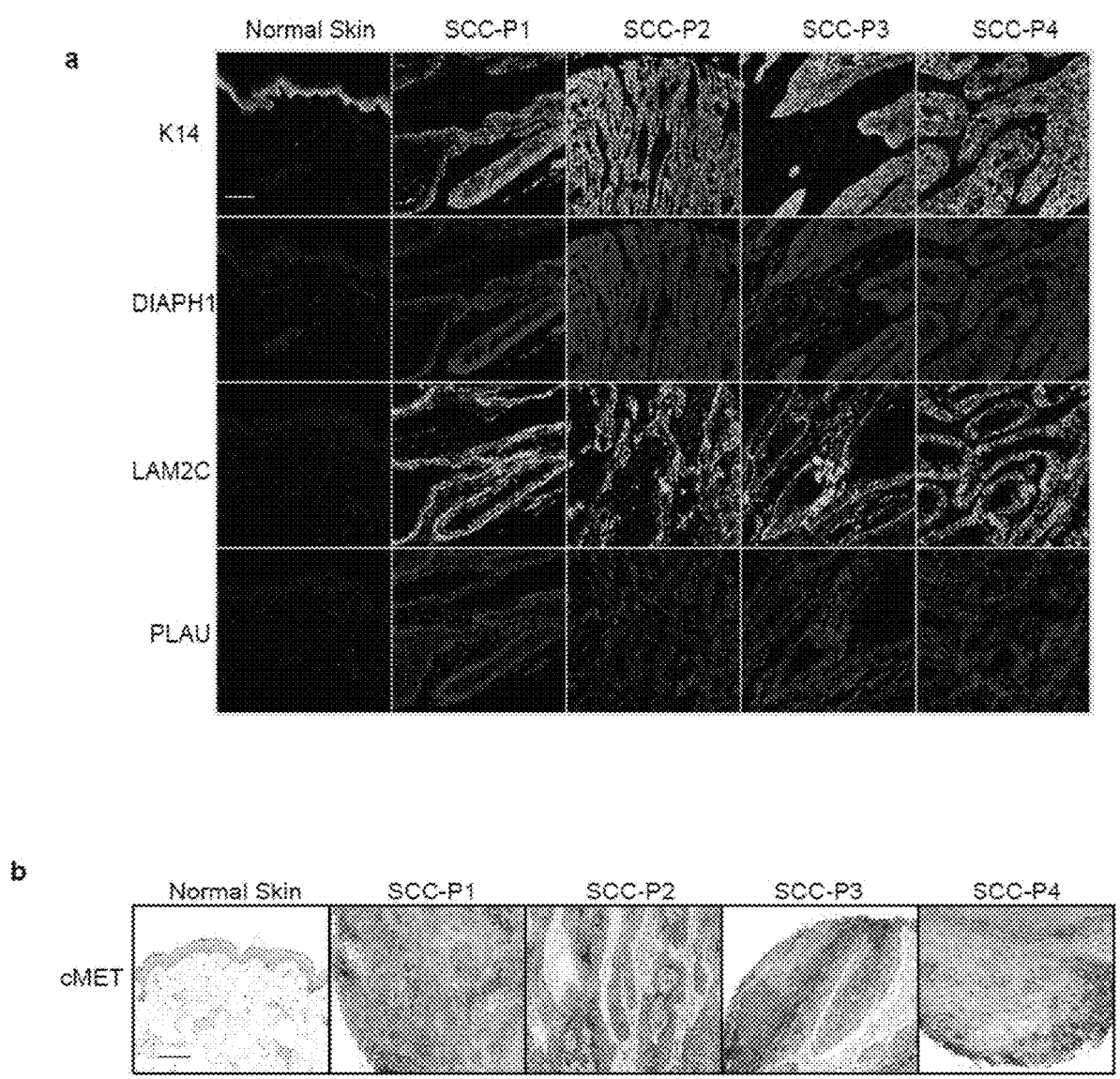
FIG. 2 shows data showing that expression of pro-invasive miR-198 target genes enhance invasion of carcinoma cells. a) Immunofluorescence staining of KRT14, PLAU, LAMC2 and DIAPH1 on normal skin and SCC patient samples. A significant increase in protein expression of target genes is clearly observed in all SCC patient samples compared to the normal skin (left column) (n=73). b) Immunohistochemistry of c-MET in SCC patient samples and normal skin (n=73). c) Boyden chamber invasion assay on SCC12 transfected with a non-targeting siRNA or siRNA against DIAPH1, LAMC2 and PLAU. Representative images of migrated cells detected with Giemsa staining. Cells were counted from six independent fields and histogram represents the relative number of invaded cells. P<0.001 Error bars represent s.d d) Organotypic invasion assay with SCC12 cells expressing control shRNA or shRNA against LAMC2, DIAPH1 and PLAU. SCC12 cells were detected by immunohistochemistry against KRT14 (in red). Number of cells invading the dermal matrix were counted and plotted as relative percentage of invaded cells. P<0.001 Error bars represent the standard deviation (s.d.)
Figure 2:
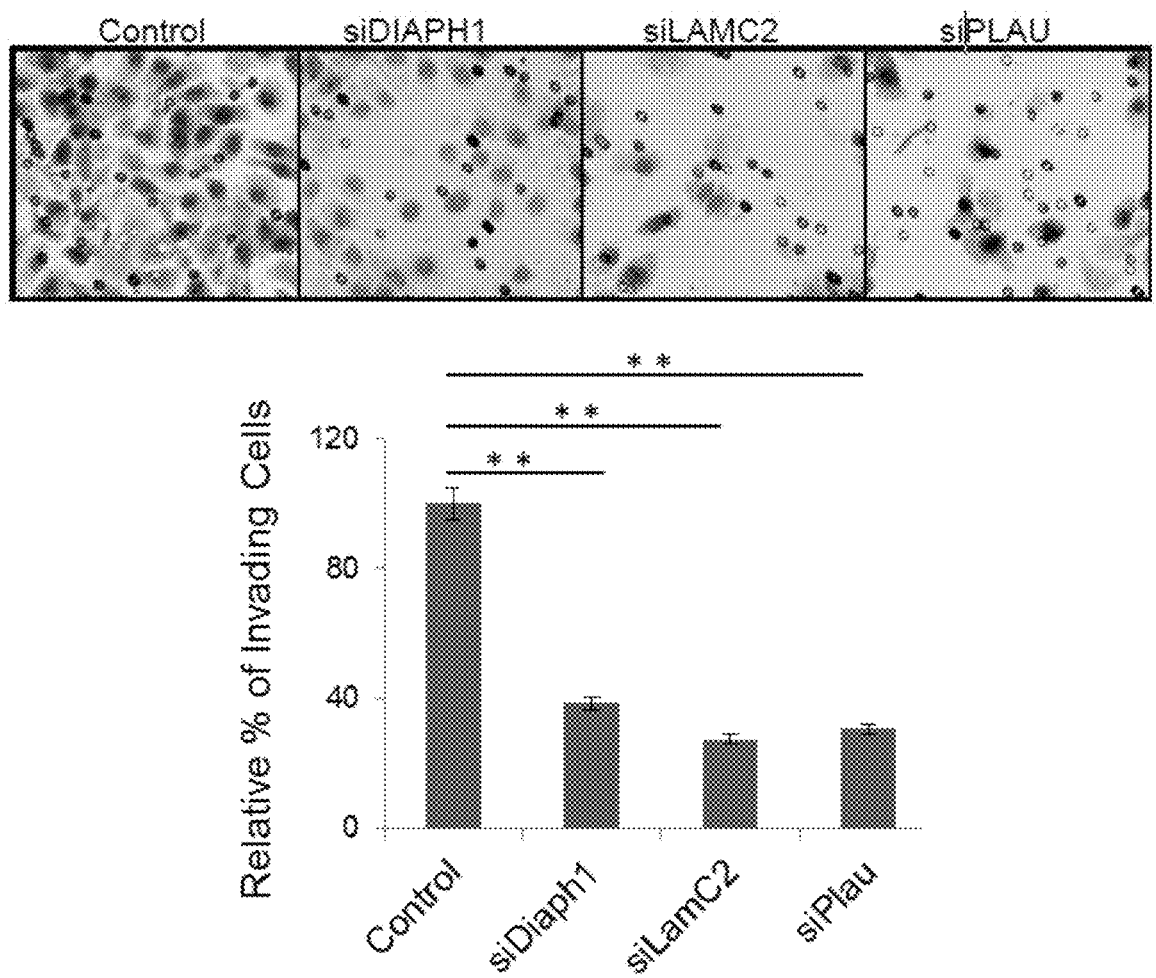
Figure 2:
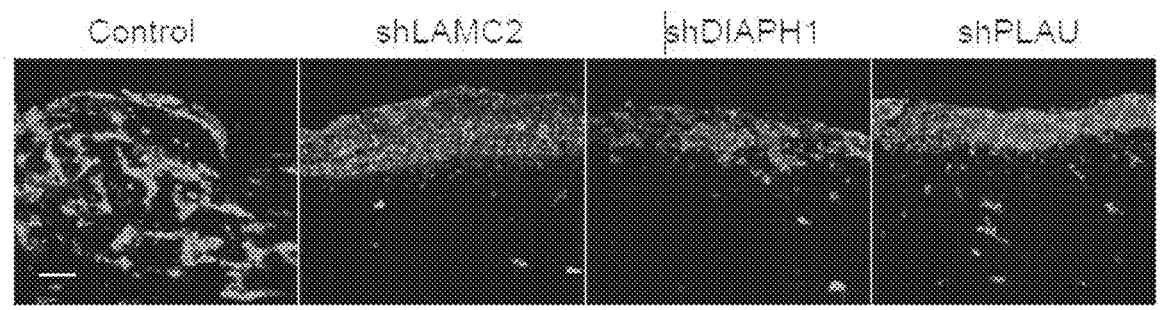
Figure 2:
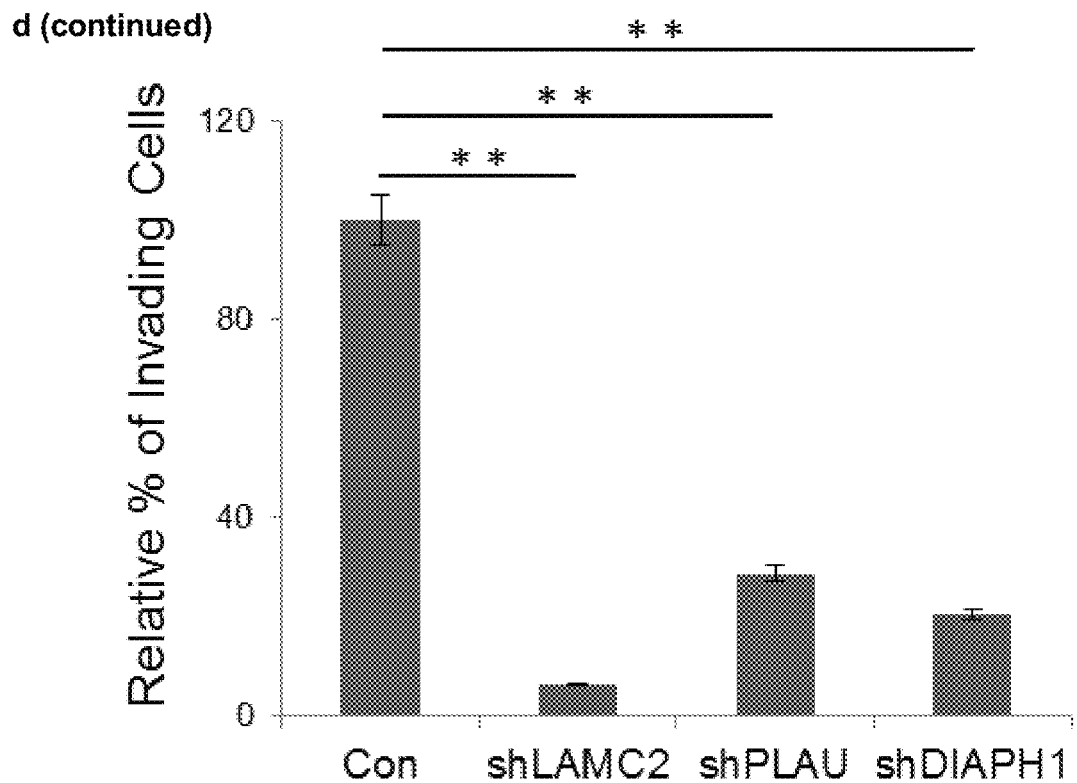
Figure 5:
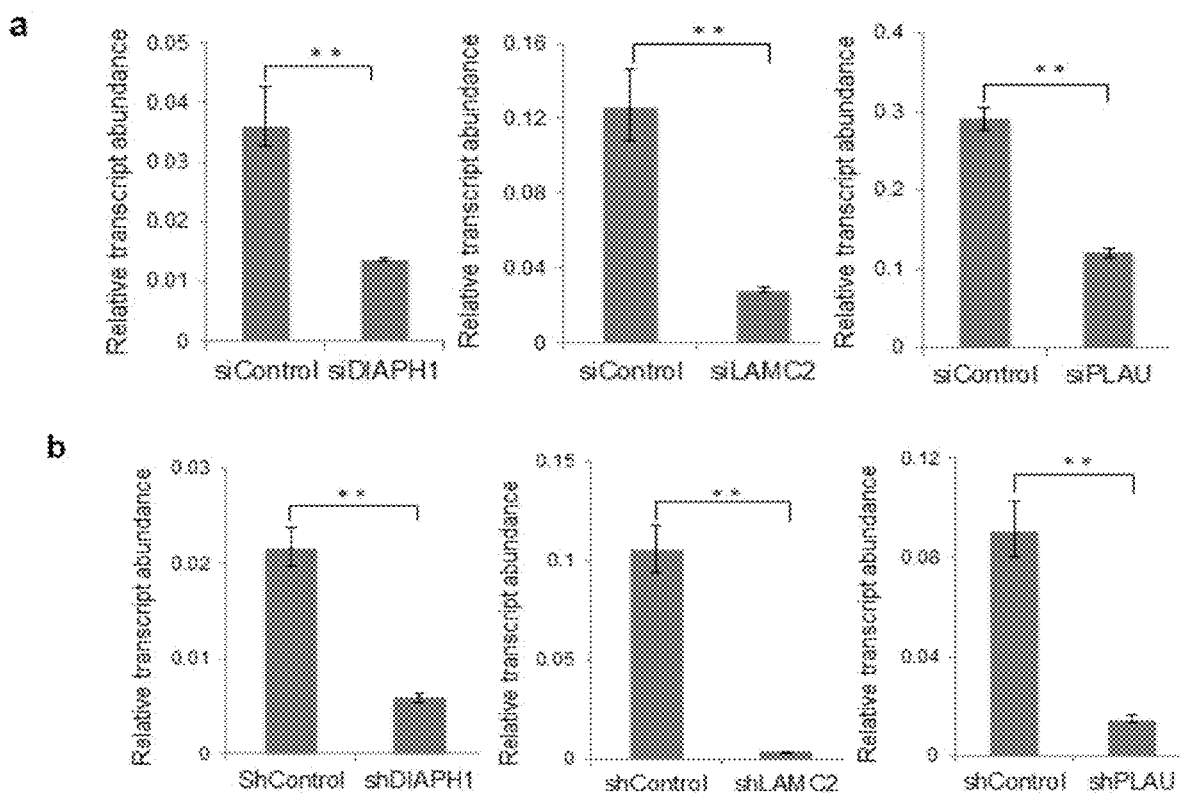
FIG. 5 shows the results of the down-regulation of miR-198 target genes using specific siRNA or shRNA in SCC12 cells. a) Histogram representing DIAPH1, LAMC2 and PLAU transcript abundance in SCC12 cells transfected with control non-targeting siRNA or gene-specific siRNA against DIAPH1, PLAU or LAMC2 (n=3) P<0.001. b) Histogram representing DIAPH1, LAMC2 and PLAU transcript abundance in SCC12 cells transduced with control shRNA or shRNA against DIAPH1, PLAU or LAMC2 (n=3) Student's t-test was used to calculate P value. Error bars denote mean±s.e.m. P<0.001.

Due to striking similarity in collective migration of squamous carcinoma cells and cell migration during wound healing, the expression of miR-198 target genes in cutaneous squamous cell carcinoma (SCC) was investigated. In the absence of anti-migratory miR-198, all the examined pro-migratory target genes, including urokinase-type plasminogen activator (PLAU), a serine protease degrading extracellular matrix 6, diaphanous homolog 1 (DIAPH1), involved in actin polymerization 7, laminin gamma 2 chain (LAMC2), an essential component of the basement membrane protein laminin 3328 and met proto-oncogene 9 (cMET), which encodes tyrosine-kinase activity, were clearly expressed in highly proliferating keratinocytes in cutaneous squamous cell carcinoma (SCC) (FIG. 2a, 2b). Furthermore, the role of these target genes in promoting invasion of keratinocytes was investigated. SCC12 cells transfected with siRNA against miR-198 target genes or control siRNA were subjected to Boyden chamber transwell assay (FIG. 5a). Following migration, cells that had attached to the lower surface of the filters were counted 24 hours after incubation (FIG. 2c, 2d). Knockdown of target genes resulted in a significant reduction in number of cells that invade through the matrix (FIG. 2c, right panel).

Figure 6:
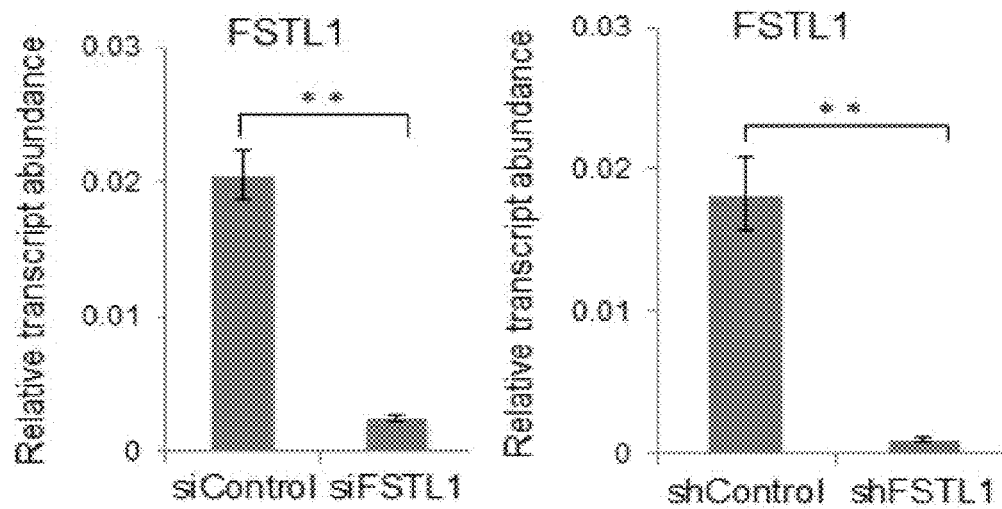
FIG. 6 shows data supporting that FSTL1 is pro-invasive and pro-inflammatory in SCC. a) Histogram representing FSTL1 transcript abundance in SCC12 cells transfected with control non-targeting siRNA or shRNA or gene-specific siRNA or shRNA against FSTL1 (n=3). Student's t-test was used to calculate P value. Error bars denote mean±s.e.m. **P<0.001. b) Gene expression values of selected genes from microarray data of SCC12 cells transfected with control non-targeting shRNA or shRNA against FSTL1 represented as a heat-map. Expression values displayed in shades of red (low) or blue (high) relative to the individual mean value of the gene in a linear scale. c) Histogram representing relative transcript abundances (control versus FSTL1 knockdown) of selected genes identified from microarrays and validated by qRT-PCR (n=3). Results show significant correlation with microarray data. Student's t-test was used to calculate P value and error bars denote mean±s.e.m. *P<0.05, **P<0.001.
Figure 6:
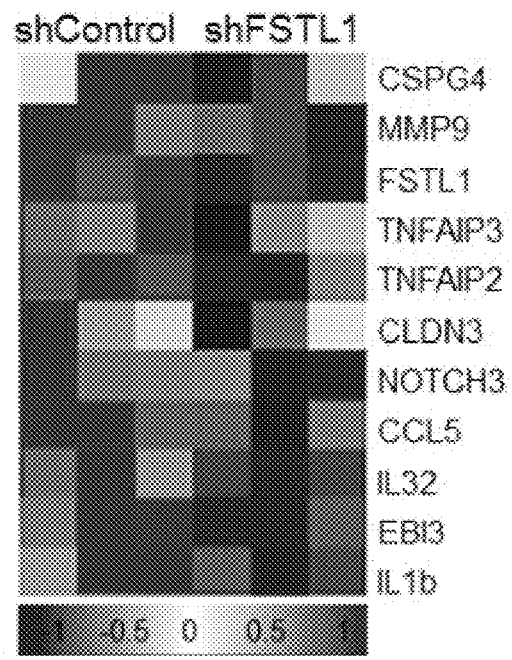
Figure 6:
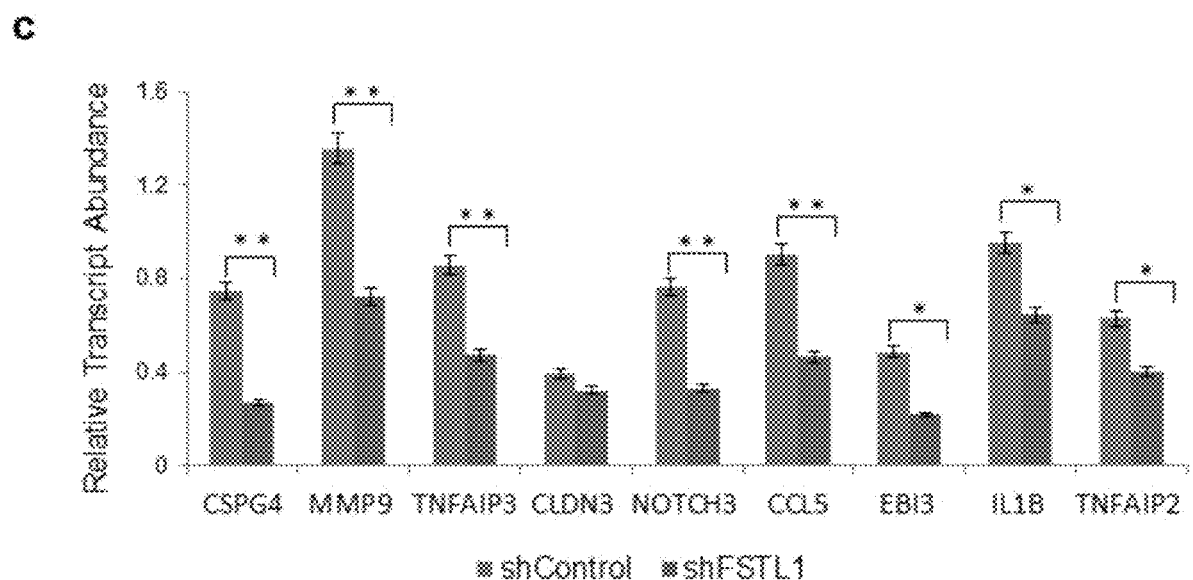

To confirm the role of miR-198 target genes in cutaneous squamous cell carcinoma (SCC) invasion, an organotypic model of cancer cell invasion was used, which closely mimics in vivo stromal invasion. SCC12 cells transduced with specific shRNA against LAMC2, PLAU and DIAPH1 were cultured on collagen:matrigel gels with incorporated fibroblasts. Substantial knockdown of target genes (FIG. 6) lead to a significant reduction in the number of invading cells in collagen matrix (FIG. 2d) Taken together, this clearly indicates that knock-down of targets of miR-198 inhibits migration and invasion of keratinocytes and highlights the role of exonic miR-198 as a tumour suppressor in cutaneous squamous cell carcinoma (SCC).

Figure 3:
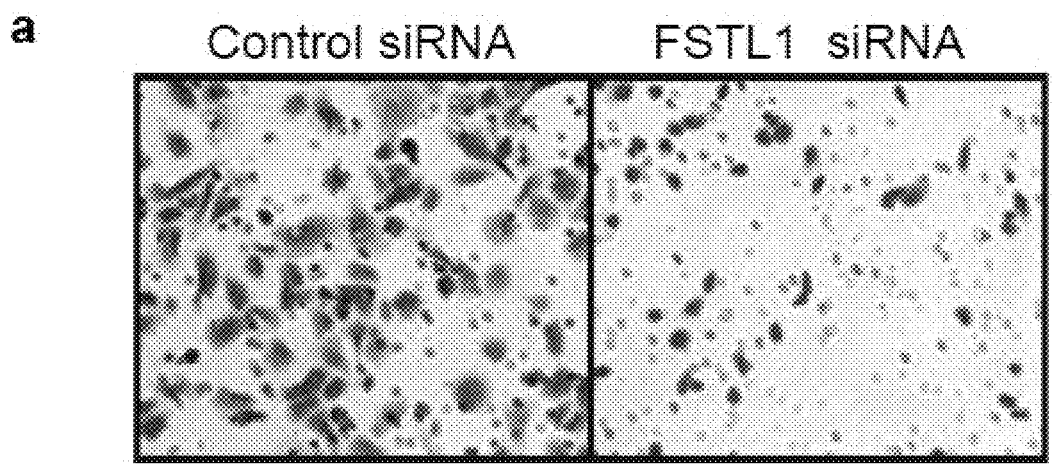
FIG. 3 presents data showing pro-invasive FSTL1 enhances carcinoma invasion. a) SCC12 cells transfected with control siRNA (left panel) or siRNA against FSTL1 (right panel) subjected to Boyden chamber assay. Representative images of migrated cells detected with Giemsa staining. b) Cells were counted from six independent fields and histogram represents relative number of invaded cells. c) Organotypic invasion assay performed using SCC12 cells transduced with control shRNA or shRNA against FSTL1. Sections were stained for KRT14 (in red) and CSPG4 or FSTL1 (in green). SCC12 cells treated with shRNA against FSTL1 displayed decreased invasion into the gel compared to the control. d) Histogram shows quantification of the no of cells invaded. P<0.001 Error bars represent s.d e) Quantification of band intensities form three independent experiment represented as a histogram. P<0.001 Error bars represent s.d f) Gelatin zymography was performed with equal amount of cell culture supernatant from SCC12 cells transduced with control shRNA or shRNA against FSTL1.g) Immunohistochemistry detection of MMP9 (top panel) and CSPG4 (bottom panel) on normal skin sections or SCC patient tissues (n=73).
Figure 3:
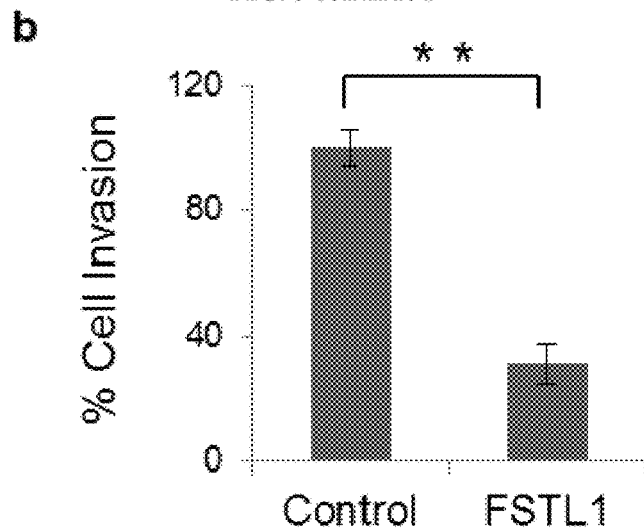
Figure 3:
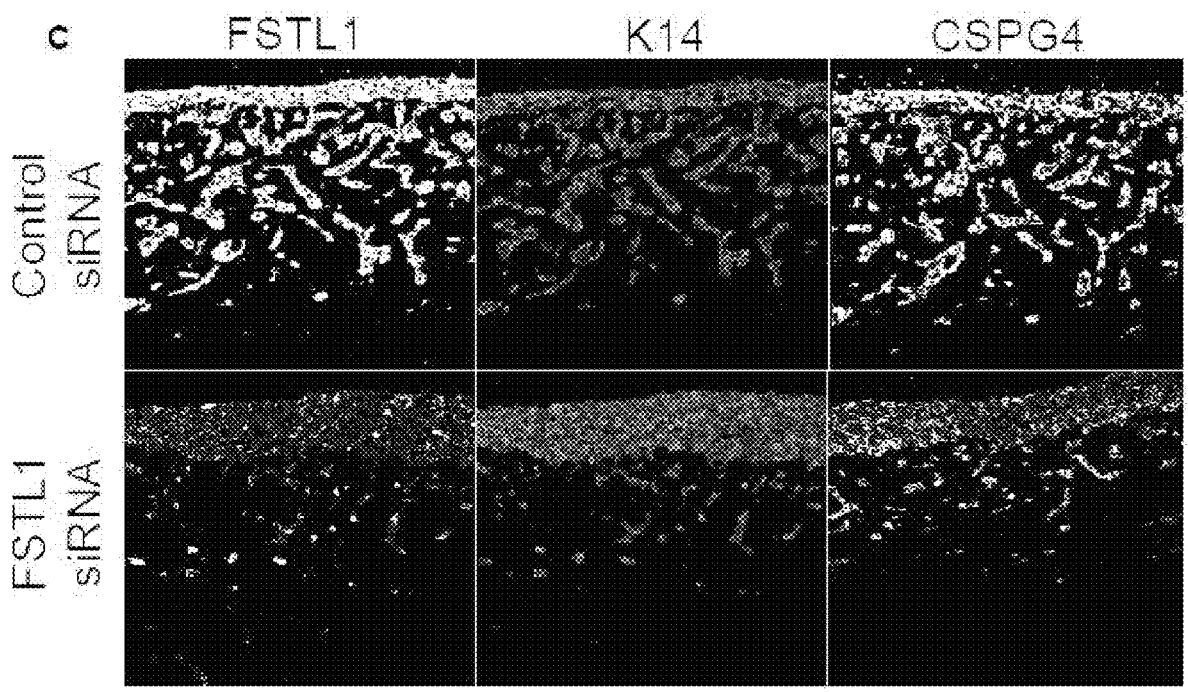
Figure 3:
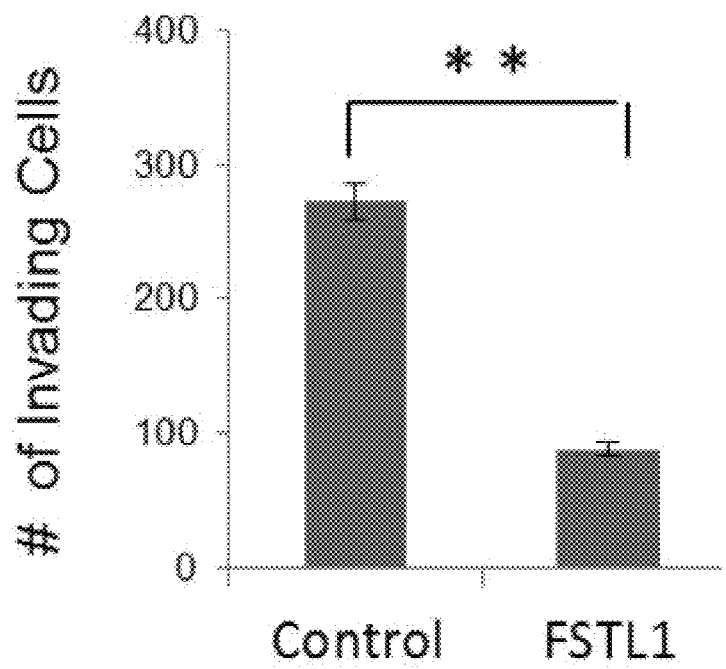
Figure 3:
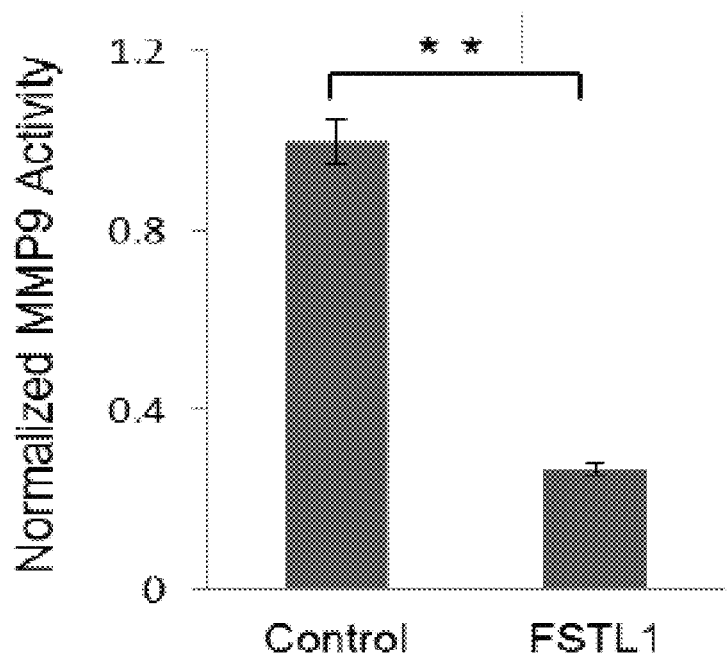
Figure 3:
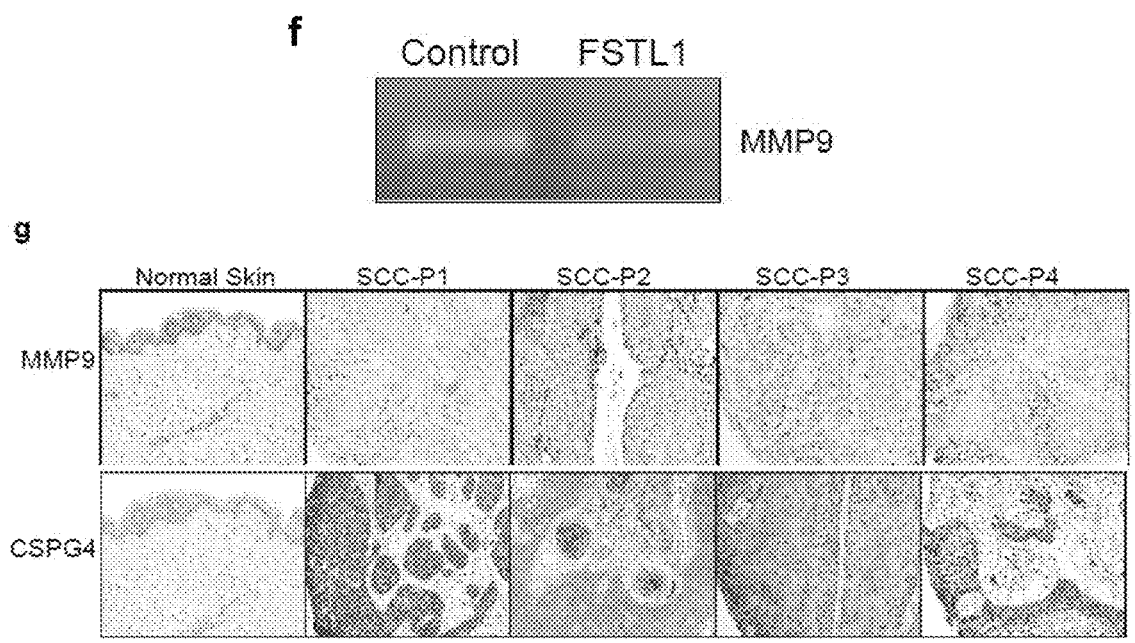

To disseminate the role of pro-migratory glycoprotein FSTL1 expressed from the linked open reading frame of miR-198 primary transcript in SCC, SCC12 cells transfected with siRNA against FSTL1 or control siRNA were subjected to Boyden chamber trans-well assay (FIG. 6a). Knockdown of FSTL1 resulted in a significant reduction in the number of migrated cells (FIG. 3a, 3b). Stable knock down of FSTL1 using shRNAs in SCC12 cells showed a significant reduction in the number of invading cells, as well as the depth of invasion in organotypic assay (FIG. 3c). Quantification of depth of invasion showed that cutaneous squamous cell carcinoma (SCC) cells with FSTL1 invaded almost two-fold deeper into the gel (FIG. 6b, FIG. 3d). Further, knockdown of FSTL1 in SCC12 cells lead to a significant down-regulation of chondroitin sulfate proteoglycan 4 (CSPG4), which is essential for the growth, migration, and metastatic dissemination of tumour cells 11 (FIG. 3c, 3d). As an activator of MMP complexes 12, CSPG4 is an essential factor for localised invasion at the leading edge of invasive primary tumours. Cancer invasion is generally associated with over-expression of extra-cellular matrix (ECM) degrading proteinases, such as the gelatinase B MMP913. FSTL1 knockdown in SCC12 cell lines resulted in decreased expression and activity of pro-MMP9, as detected by qRT-PCR and gelatin zymography on conditioned media (FIG. 3e, 3f). Taken together, the multifunctional glycoprotein FSTL1 potentially regulates expression of CSPG4 which can activate MMP complexes and promote cancer invasion. In support of the aforementioned results, analysis of cutaneous squamous cell carcinoma (SCC) tissue arrays showed increased expression of both CSPG4 and MMP9 in cancer cells, compared to normal epidermal keratinocytes (FIG. 3g). In conclusion, although not an oncogene according to the classical definition in the art, increased persistent expression of FSTL1 directly, or indirectly, enhances activation of multiple signalling pathways associated with oncogenic transformation and facilitates progression of cutaneous SCC.

Figure 4:
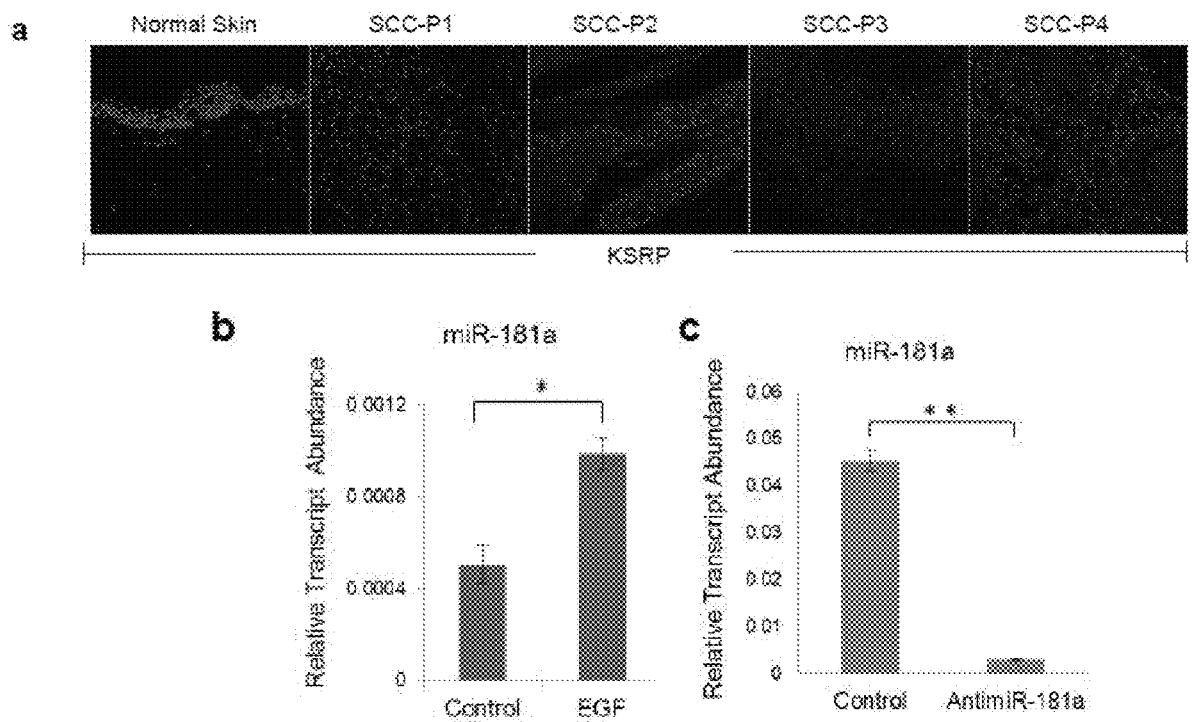
FIG. 4 shows data depicting how the interplay between two RNA-binding proteins controls the fate of FSTL1 expression. a) Immunofluorescence staining of KSRP on normal skin and SCC patient samples. Compared to the normal skin (left column), a significant decrease in KSRP protein expression observed in all patient samples. b) Histogram representing miR-181a relative transcript abundance in keratinocytes treated with EGF or control (n=3) c) Histogram representing miR-181a relative transcript abundance in SCC12 cells treated with control or antimiR-181a oligonucleotides (n=3) Student's t-test was used to calculate P value. Error bars denote mean±s.e.m. (*[P<0.05], **[P<0.001]) d) Western blot detection of KSRP, FSTL1 and β-actin on SCC12 cells transfected with control or anti-miR-181a. e) Histogram representing miR-198 relative transcript abundance in SCC12 cells treated with control or anti-miR-181a oligonucleotides (n=3) Student's t-test was used to calculate P value. Error bars denote mean±s.e.m. *[P<0.05] f) In situ hybridization with LNA probes specific for mature miR-181a on normal skin (left panel) (n=5) and SCC tissue samples (n=73). miR-198 is stained red and nuclei are stained blue. g) Immunofluorescence staining of HuR on normal skin and SCC patient samples. Compared to the normal skin (left column), a significant increase in HuR protein expression observed in all patient samples (n=73). h) RNA-gel retardation assay shows binding of HuR to the AU rich motif in the loop of pre-miR-198 transcript (left panel) and abrogation of binding with mutant precursor lacking U-rich motif (right panel). i) Western blot detection of KSRP, HuR, FSTL1 and β-actin in SCC12 cells transfected with a non-targeting siRNA or siRNA against KSRP or HuR (n=3). J) Chimeric Luciferase reporter constructs and control GFP cRNA were subjected to in vitro translation in the presence of cytosolic extracts from SCC12 cells transduced with control siRNA or siRNA against HuR or KSRP.
Figure 4:
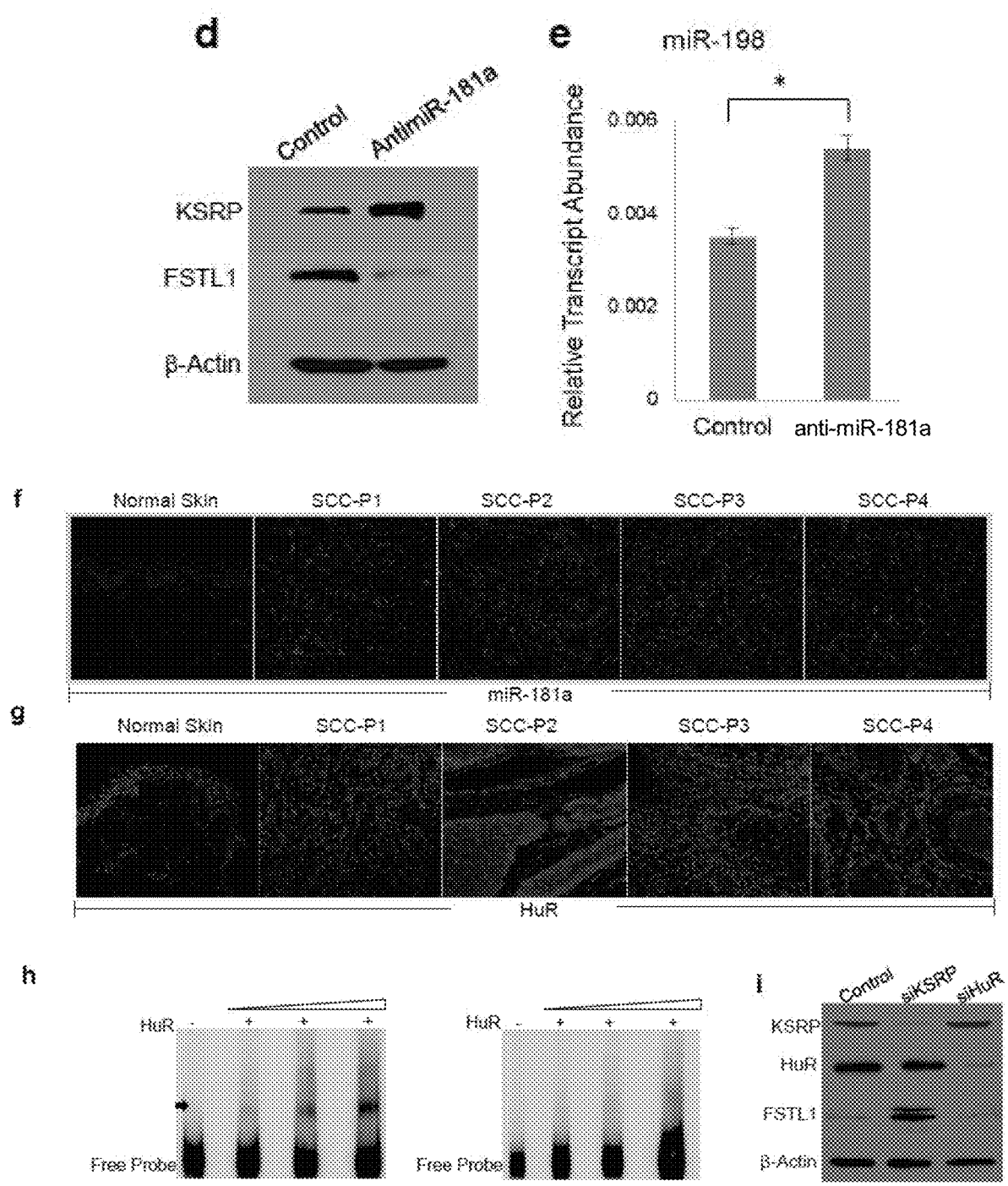
Figure 4:
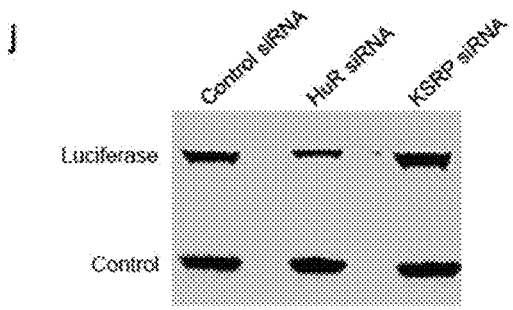

To understand the molecular mechanisms that lead to the failure of molecular switch in cutaneous squamous cell carcinoma (SCC), the expression of KSRP, which is essential for the processing of miR-198, was analysed. In comparison to the normal skin, low levels of KSRP were observed in cutaneous squamous cell carcinoma (SCC) samples (FIG. 4a). Epidermal growth factor (EGF), a factor frequently over-expressed in cancer, is known to stimulate the expression of miR-181a. miR-181a is shown to directly target and significantly down-regulate KSRP expression in SCC14 (FIG. 4b-f). Down-regulation of miR-181a using anti-miR-181a resulted in the up-regulation of KSRP, with a significant down-regulation of FSTL1 and a concomitant up-regulation of miR-198 (FIG. 4c-e). In summary, low levels of KSRP impede processing of miR-198 and facilitate FSTL1 expression in cutaneous squamous cell carcinoma (SCC).

Prolonged and persistent expression of FSTL1 in cutaneous squamous cell carcinoma (SCC) prompted the examination of other factors, capable of enhancing the stability of FSTL1 transcripts. For example, Hu antigen R (HuR) is an mRNA-binding protein which binds to labile transcripts, including cyclo-oxygenase-2 (COX-2) associated with carcinogenesis in SCC. It was hypothesised that Hu antigen R (HuR) controls the stability of FSTL1 transcript based on the presence of consensus HuR binding motif (NNUUNN-UUU-U rich element) in the precursor sequence of exonic miR-19817 (data not shown). Elevated expression of HuR was shown to be present in cutaneous squamous cell carcinoma (SCC) samples (FIG. 4g). RNA gel retardation assays using recombinant HuR confirmed the binding of HuR to the precursor miR-198 transcript (FIG. 4h, left panel). Formation of an RNA-protein complex in the presence of recombinant HuR with wild-type probe containing a U-rich motif, but not with a mutant probe (which lacked U-rich motif), confirmed the specificity of binding (FIG. 4h, right panel). Using siRNA specifically targeting HuR or KSRP, knockdown of HuR, but not KSRP in the presence of actinomycin D, resulted in the loss of FSTL1 protein expression. This emphasises the role of HuR in enhancing the stability of FSTL1 transcript (see FIG. 4i).

Finally, an in vitro translation assay using capped, chimeric reporter transcript containing Luc upstream of the full-length FSTL1 3'-UTR [Luc-FSTL1 3'-UTR] was performed to confirm the role of HuR. The reporter was subjected to in vitro translation in rabbit reticulocyte lysate, in the presence of lysate from SCC12 cells transfected with control siRNA or siRNA against HuR or KSRP. Down-regulation of HuR, but not KSRP, clearly affected the translation of the reporter, thereby confirming the role of the HuR to confer stability to the transcript. As a control for target specificity, a cRNA encoding GFP was added to each reaction mixture. The expression of the GFP was shown to be constant under all conditions, indicating that the inhibitory activity was specific for the FSTL1 3'-UTR-containing chimeric transcript (FIG. 4i). In summary, down-regulation of KSRP and expression of HuR, which is shown to enhance the stability of FSTL1 mRNA, leading to constitutive expression of FSTL1 protein in cutaneous squamous cell carcinoma (SCC).

Wound healing is a self-limiting dynamic event where barrier disruption is transient and inflammation resolves with the completion of re-epithelialisation. Following wound repair keratinocytes revert to epithelial-like phenotype and re-differentiate to restore epidermal barrier, whereas carcinoma cells lose cell-cell contact, and transdifferentiate to acquire a mesenchymal-like phenotype with a gene expression profile that contributes to increased migration and invasion. Furthermore, perpetual perturbation of epidermal gene expression not only results in uncontrolled growth but also leads to chronic inflammation, linked to carcinogenesis. The miR-198/FSTL1 genetic switch is shown to tightly regulate gene expression in the wound microenvironment to facilitate effective wound healing.

Upon cutaneous injury, transient down-regulation of anti-migratory miR-198 is essential to facilitate migration of keratinocytes towards the wound edge. However, in cutaneous squamous cell carcinoma (SCC), perpetual absence of miR-198 and sustained expression pro-migratory target genes enhance keratinocyte migration and invasion. Persistent expression of PLAU and LAMC2 by carcinoma cells leads to increased fibrinolysis and degradation of extracellular matrix components. Although basement membranes are protective and serve as a barrier for tumour growth, enhanced secretion of autocrine factors, including LAMC2 and Laminin 332, by basement membrane promotes tumourigenesis in cutaneous squamous cell carcinoma (SCC). Expression of an actin-binding protein DIAPH1 facilitates polarised cancer cell migration. By targeting regulators of mitogenic and motogenic pathways, miR-198 inhibits migration. Further suppressing the oncogene cMET, miR-198 also functions as a tumour suppressor. By targeting FUT8 and FGFR1, miR-198 further controls metastasis in colorectal cancer and induces apoptosis in lung cancer respectively, all emphasising the role of miR-198 as a tumour suppressor.

Examining the role of FSTL1 at the intersection of wound healing and cancer; the protein is essential for keratinocyte migration and wound re-epithelialisation. However, in carcinoma cells sustained expression of FSTL1 contributed to oncogenic transformation through downstream regulators CSPG4 and MMP9. CSPG4 not only activated FAK and ERK1/2 to facilitate tumour invasion and growth, CSPG4 also activated proteolytic degradation of extracellular matrix by regulating the activity of MMP-2 and MMP-912. Additionally, FSTL1 is a secreted pro-inflammatory glycoprotein, which, when elevated in various inflammatory conditions, mediated inflammatory response and enhances the synthesis of pro-inflammatory cytokines and chemokines including, but not limited to, IL-6, TNF-α and IL1-β, by immune cells. Supporting this observation, FSTL1 knockdown in SCC12 cells lead to the down-regulation of pro-inflammatory genes including IL-27B, IL-10, TNFAIP2/3, CCL5 and IL-32 (FIG. 6c). In summary, neutralising FSTL1 lead to the development of an efficient strategy for resolution of inflammation in chronic inflammatory conditions. Finally, expression of FSTL1 as a pro-inflammatory signature in cutaneous squamous cell carcinoma (SCC), colorectal cancer, and role of FSTL1 as a mediator of cancer cell invasion in bone metastasis all indicate the therapeutic potential of targeting FSTL1 to treat multiple forms of cancer.

The subtle but crucial boundaries between the role of FSTL1 in wound healing and its role in the pathology of cutaneous squamous cell carcinoma (SCC) indicated that FSTL1 expression is tightly regulated, allowing the protein to perform its physiological function while avoiding the serious consequences of sustained expression. The contrast between the essential role of FSTL1 in injury/wound healing and its contribution to oncogenic transformation in cutaneous squamous cell carcinoma (SCC) highlights the regulatory complexity of FSTL1. In summary, this highlights the importance of the regulatory switch which controls temporal and mutually exclusive expression of miR-198 and FSTL1. However, cancer cells exploit the regulatory switch by blocking the processing of the anti-migratory, tumour suppressor miR-198 to facilitate sustained production of the pro-migratory, pro-invasive and pro-inflammatory FSTL1. Events that occur in normal wound healing are not sufficient to trigger tumour formation; however, sustained aberrant expression of components in the wound microenvironment can trigger epidermal hyperproliferation, chronic inflammation and invasion, thus leading to carcinogenesis. Modulation of the components of the molecular switch can lead to design of better therapeutic options for cutaneous squamous cell carcinoma (SCC) with improved patient outcome.

The term "miRNA", as used herein, is understood as a single stranded non-coding RNA sequence which is capable of interacting with the 3'-untranslated region of a mRNA thus preventing its translation. The terms "microRNA" or "miRNA" that may be used interchangeably herein, are endogenous RNAs, some of which are known to regulate the expression of protein-coding genes at the post-transcriptional level. As used herein, the term "microRNA" refers to any type of micro-interfering RNA, including but not limited to, endogenous microRNA and artificial microRNA. Typically, endogenous microRNAs are small RNAs encoded in the genome which are capable of modulating the productive utilisation of mRNA. A mature miRNA is a single-stranded RNA molecule of about 21-23 nucleotides in length which is complementary to a target sequence, and hybridises to the target RNA sequence to inhibit its translation. miR-NAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression.

Thus, as used herein, an "inhibitor" refers to any molecule which inactivates and/or down-regulates the expression of any one or more of the biomarkers or biomarkers disclosed herein. The inhibitor can be a small molecule, an antisense nucleic acid, a small interfering RNA or a microRNA-based compound. For example, the FSTL1 expression inhibitor may be a direct inhibitor such that it interacts with the FFSTL1 protein or with a nucleic acid encoding the FSTL1 protein. Alternatively, the inhibitor may be an indirect inhibitor which interacts upstream or downstream of, for example, the FSTL gene in the regulatory pathway and which does not interact with the FSTL protein or with a nucleic acid encoding the FSTL protein directly. In one example, the inhibitor may be peptide nucleic acid (PNA) derivatives of FSTL inhibitor sequence or Tiny locked nucleic acid (LNA) anti-miRs for seed-sequence of the inhibitor.

The term "peptide nucleic acid (PNA)" as used herein refers to DNA mimics with a pseudo-peptide backbone.

As used herein, the term "locked nucleic acid" (also known as LNA or "inaccessible RNA") refers to a modified RNA nucleotide. The ribose moiety of an LNA nucleotide is modified with an extra bridge connecting the 2' oxygen and 4' carbon. The bridge "locks" the ribose in the 3'-endo (North) conformation, which is the same confirmation often found in the A-form duplexes. The, usually synthetic, locked nucleic acid nucleotides can be mixed with DNA or RNA residues in the oligonucleotide, whenever desired, and hybridize with DNA or RNA according to Watson-Crick base-pairing rules. The locked ribose conformation enhances base stacking and backbone pre-organization. This significantly increases the hybridization properties (melting temperature) of oligonucleotides.

The term "tiny LNA anti-miRs" as used herein refers inaccessible RNA, is a modified RNA nucleotide. In one example, transfection of tiny LNAs into cells resulted in simultaneous inhibition of RNAs within families sharing the same seed with concomitant upregulation of direct targets. In one example, transfection of tiny LNAs systemically showed long term RNA silencing.

It was demonstrated, in transwell and organotypic assays, that the knockdown of FSTL1, as well as miR-198 target genes DIAPH1, LAMC2 and PLAU, resulted in dramatic loss of invasive properties in a cutaneous squamous cell carcinoma (SCC) cell line. Modulating levels of miR-198 via KSRP, which is essential for the processing of miR-198, resulted in the inverse modulation of FSTL1. This data indicated that enhancing the levels of miR-198, for example through the application of oligonucleotide mimics, which can be readily manufactured for, for example, topical application, can be used in the treatment of cutaneous squamous cell carcinoma (SCC).

The compositions as described herein may be administered in a number of ways depending upon whether local or systemic treatment is desired and upon the area to be treated. Administration may be topical, pulmonary (e.g., by inhalation or insufflation of powders or aerosols, including by nebuliser; intratracheal, intranasal, epidermal and transdermal) or systemic such as oral, and/or parenteral. In one example, the compositions as described herein may be administered via systemic or topical administration. In another example, the compounds disclosed herein are administered according to any one of the following methods: orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravenously, intravesicularlly, intravitreally, liposomally, locally, mucosally, orally, enterally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion or any combination thereof.

Parenteral administration includes intravenous, intraarterial, subcutaneous, intraperitoneal or intramuscular injection or infusion; or intracranial, e.g., intrathecal or intraventricular, administration.

In one example, the administration is via topical administration. Compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In one example, the composition for topical administration comprises the composition as described herein and a dermatologically acceptable vehicle. The vehicle may be aqueous or non-aqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous non-aqueous or oil phase (oil-in-water emulsion), or a continuous non-aqueous or oil phase and a discontinuous aqueous phase (water-in-oil emulsion).

In one example, the composition as described herein may be topically administered using a transdermal patch. In one example, the transdermal patch comprises an adhesive layer for attachment to the patch to the skin, and a drug-impermeable backing layer. In one example, the adhesive layer contains the composition as described herein in combination with an adhesive polymer. In this type of system, the composition as described herein is released from the adhesive layer and passes directly to the skin.

In one example, the transdermal system has a reservoir layer containing the composition as described herein. The drug reservoir layer is a liquid, gel, or semisolid compartment containing a drug solution or suspension, where the reservoir layer is positioned in between the adhesive layer and the backing layer. In this type of system, the composition as described herein is released from the reservoir layer and passes through the adhesive layer.

The pharmaceutical excipients used in the topical preparation of the present disclosure may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include, but are not limited to, water; ethyl alcohol; isopropyl alcohol; mixtures of water and ethyl and/or isopropyl alcohols; glycerine; ethylene, propylene or butylene glycols; DMSO; and mixtures thereof. Suitable solvents for a hydrophobic topical formulation include, but are not limited to, mineral oils, vegetable oils, and silicone oils. If desired, the composition as described herein can be dissolved or dispersed in a hydrophobic oil phase, and the oil phase can then be emulsified in an aqueous phase comprising water, alone or in combination with lower alcohols, glycerine, and/or glycols.

Suitable emollients include, but are not limited to, hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include, but are not limited to, dimethyl polysiloxanes, methyl(phenyl) polysiloxanes, and water-soluble and alcohol-soluble silicone glycol copolymers. Suitable triglyceride esters for use as emollients include, but are not limited to, vegetable and animal fats and oils including castor oil, safflower oil, cotton seed oil, corn oil, olive oil, cod liver oil, almond oil, avocado oil, palm oil, sesame oil, soybean oil and combinations thereof.

Suitable esters of carboxylic acids or diacids for use as emollients include, but are not limited to, methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, diisopropyl sebacate and combinations thereof.

Other suitable classes of emollients or emulsifiers which may be used in the topical formulations include, but are not limited to, fatty acids, fatty alcohols, fatty alcohol ethers, ethoxylated fatty alcohols, fatty acid esters of ethoxylated fatty alcohols, waxes and combinations thereof.

Specific examples of fatty acids for use as emollients include, but are not limited to pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, erucyl alcohols, as well as 2-octyl dodecanol and combinations thereof.

Specific examples of waxes suitable for use as emollients include, but are not limited to, lanolin and derivatives thereof, including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes; and combinations thereof.

Polyhydric alcohols and polyether derivatives can be used as solvents and/or surfactants in the topical formulations. Suitable polyhydric alcohols and polyethers include, bur are not limited to, propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2, 6-hexanetriol, 2-ethyl-1,3-hexanediol, vicinal glycols having 15 to 18 carbon atoms, polyoxypropylene derivatives of trimethylolpropane, and combinations thereof.

Polydydric alcohol esters can be used as emulsifiers or emollients. Suitable polydydric alcohol esters include, but are not limited to, ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and combinations thereof.

Suitable emulsifiers for use in topical formulations include anionic, cationic, non-ionic, and zwitterionic surfactants. Suitable ionic emulsifiers include phospholipids, such as lecithin and derivatives.

Lecithin and other phospholipids can be used to prepare liposomes containing the composition as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multi-lamellar liposomes. Continued high-shear sonication tends to form smaller uni-lamellar liposomes. Hydrophobic chemicals can be dissolved into the phospholipid bilayer membrane. The lipid bilayers of the liposomes deliver the composition as described herein to keratinocytes by fusing with the cell membrane of the keratinocytes.

In one example, the topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, but are not limited to, cholesterol and cholesterol fatty acid esters; amides such as fatty acid amides, ethoxylated fatty acid amides, and fatty acid alkanolamides can also be used as emollients and/or penetration enhancers.

Suitable viscosity enhancers or thickeners which can be used to prepare a viscous gel or cream with an aqueous base include, but are not limited to, sodium polyacrylate, xanthan gum, polyvinyl pyrollidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, polyethoxylated alkane thiols and combinations thereof.

Suitable preservatives and/or antioxidants for use in topical formulations include, but are not limited to, benzalkonium chloride, benzyl alcohol, phenol, urea, parabens, butylated hydroxytoluene (BHT), butylated hydroxyanisole (BHA), Tocopherol, and mixtures thereof.

Suitable chelating agents for use in topical formulations include, but are not limited to, ethylene diamine tetraacetic acid (EDTA), alkali metal salts thereof, alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid.

The various examples of creams, ointments, lotions, solutions, gels, sprays and patches may incorporate the composition as described herein as the active ingredient, in combination with penetration enhancing agents and other active agents acting synergistically on the skin for the promotion of wound healing or wound closure or the treatment of chronic cutaneous wound.

In one example, of the topical formulation can includes at least one or more oligonucleotides and/or at least one or more RNA molecules in a concentration of from about 0.005% by weight to about 50% by weight. Formulations containing at least one or more oligonucleotides and/or at least one or more RNA molecules in an aqueous carrier can typically contain from about 0.005% by weight to about 0.5% by weight of the at least one or more oligonucleotides and/or at least one or more RNA molecules, preferably about 0.01% by weight to about 0.1% by weight, more preferably about 0.01% by weight to about 0.05% by weight. Formulations containing at least one or more oligonucleotides and/or at least one or more RNA molecules in an oil or wax carrier can typically contain from about 0.005% to about 50% by weight of at least one or more oligonucleotides and/or at least one or more RNA molecules, preferably about 0.01% by weight to about 25% by weight, more preferably about 0.1% by weight to about 10% by weight, most preferably from about 0.1% by weight to about 5% by weight. Creams, lotions, or other emulsions containing an oil phase and an aqueous phase typically contain at least one or more oligonucleotides and/or at least one or more RNA molecules in an amount of from about 0.005% to about 25% by weight, preferably about 0.005% to about 10% by weight, more preferably about 0.01% to about 5% by weight. The creams, lotions, or other emulsions may be prepared as water-in-oil or oil-in-water emulsions; in either case, the hydrophobic compound containing at least one or more oligonucleotides and/or at least one or more RNA molecules is dissolved or dispersed in the oil phase.

A suitable formulation comprises at least one or more oligonucleotides and/or at least one or more RNA molecules in a concentration of from about 0.1 to about 0.3 mg/mL (0.01% to 0.03%), and the preservative benzalkonium chloride in a concentration of from about 0.05 to about 0.2 mg/ml. The formulation is provided in a vehicle comprising water having a pH of between about 6.8 and about 7.8 as a solvent. The formulation can further comprise sodium chloride, a dibasic sodium phosphate/citric acid buffer, and optionally sodium hydroxide and/or hydrochloric acid to adjust the pH.

The topical formulation can be provided to a subject having, for example, a carcinoma found on the surface of the subject, in a bottle designed to administer the formulation in a drop-wise fashion. The subject can then administer the topical formulation at regular intervals to affected tissue, for example, in an amount of from 1 drop per 5 square centimetres of affected skin to 5 drops per square centimetre of affected skin, preferably 1 drop (where 1 drop is about 0.02 mL to about 0.05 mL, more preferably about 0.03 mL) per 5 square centimetres of affected skin to 1 drop per square centimetre of affected skin, more preferably 1 drop per 2 square centimetres of affected skin. In various embodiments, topical formulations can be administered at intervals ranging from four times per day to once per week, preferably two times per day to twice a week, more preferably two times per day to once a day. Frequency of administration can be adjusted depending on concentration of in the topical formulation, i.e., a topical formulation having a high concentration of the composition as described herein can be administered less frequently than a similar formulation having a lower concentration.

Compositions and formulations for oral administration can include powders or granules, suspensions or solutions in water or non-aqueous media, capsules, sachets or tablets. Thickeners, flavouring agents, diluents, emulsifiers, dispersing aids or binders may be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Thus, in one example, the one or more oligonucleotides and/or the one or more RNA molecules further comprise a compound selected from a group consisting of a pharmaceutically acceptable carrier, a liposomal carrier, an excipient, an adjuvant or combinations thereof.

Compositions as described herein include, but are not limited to, solutions, emulsions, and liposome-containing formulations. These compositions can be generated from a variety of components that include, but are not limited to, preformed liquids, self-emulsifying solids and self-emulsifying semisolids.

The formulations as described herein, which may conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein can be formulated into any of many possible dosage forms such as, but not limited to, tablets, capsules, liquid syrups, soft gels, suppositories, and enemas. The compositions as described herein can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilisers.

Thus, in one example, the one or more oligonucleotides and/or the one or more RNA molecules is/are provided as tablets, caplets, capsules, hard capsules, soft capsules, soft elastic gelatine capsules, hard gelatine capsules, cachets, troches, lozenges, dispersions, suppositories, ointments, cataplasms, poultices, pastes, powders, dressings, creams, plasters, solutions, patches, aerosols, nasal sprays, inhalers, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof.

In one example, the pharmaceutical compositions can be formulated and used as foams. Pharmaceutical foams include formulations such as, but not limited to, emulsions, micro-emulsions, creams, jellies and liposomes. While basically similar in nature these formulations vary in the components and the consistency of the final product.

Thus, in one example, there is disclosed a pharmaceutical composition comprising at least one or more oligonucleotides and/or at least one or more RNA molecules, wherein the one or more oligonucleotides is homologous in sequence to the nucleic acid sequence of miR-198 (SEQ ID NO: 1) or a functional part thereof; and/or wherein the one or more RNA molecules reduce the level of and/or inhibiting gene expression of a RNA target; wherein the RNA target is a gene selected from a group consisting of follistatin-related protein 1 (FSTL1), Protein diaphanous homolog 1 (DIAPH1), Laminin subunit gamma-2 (LAMC2) and urokinase-type plasminogen activator (PLAU). In another example, the one or more RNA molecules comprised in the pharmaceutical composition is/are shRNA directed against FSTL1 or a combination of shRNAs. In another example, the siRNA sequence is selected from the group consisting of SEQ ID NO: 7, SEQ ID NO: 8, SEQ ID NO: 9, and SEQ ID NO: 10 and combinations thereof.

The compositions as described herein can additionally contain other adjunct components conventionally found in pharmaceutical compositions. Thus, for example, the compositions can contain additional, compatible, pharmaceutically active materials such as, for example, antipruritics, astringents, local anaesthetics or anti-inflammatory agents, or may contain additional materials useful in physically formulating various dosage forms of the compositions of the present invention, such as dyes, flavouring agents, preservatives, antioxidants, opacifiers, thickening agents and stabilisers. However, such materials, when added, should not unduly interfere with the biological activities of the components of the compositions of the present invention. The formulations can be sterilised and, if desired, mixed with auxiliary agents, e.g., lubricants, preservatives, stabilisers, wetting agents, emulsifiers, salts for influencing osmotic pressure, buffers, colourings, flavourings and/or aromatic substances and the like which do not deleteriously interact with the nucleic acid(s) of the formulation.

The term "therapeutically effective amount" as used herein includes within its meaning a sufficient but non-toxic amount of the at least one or more oligonucleotides and/or at least one or more RNA molecules to provide the desired therapeutic effect. The exact amount required will vary from subject to subject depending on factors such as the species being treated, the age and general condition of the subject, the severity of the condition being treated, the particular agent being administered, the mode of administration, bioavailability of the active compound and so forth. Thus, it is not possible to specify an exact "effective amount". However, for any given case, an appropriate "effective amount" can be determined by one of ordinary skill in the art using routine experimentation.

Dosing is dependent on severity and responsiveness of the disease to be treated, with the course of treatment lasting from several days to several months, or until a cure is effected, or a diminution of the disease is achieved. Optimal dosing schedules can be calculated from measurements of drug accumulation in the body of the subject. The person skilled in the art can easily determine optimum dosages, dosing methodologies and repetition rates. Optimum dosages can vary depending on the relative potency of the composition, and can generally be estimated based on $EC_{50}$ values found to be effective in in vitro and in vivo animal models or based on the examples described herein. In general, dosage is from 0.01 µg to 100 g/kg of body weight, and can be given once or more daily, weekly, monthly or yearly. Thus, in one example, wherein the oligonucleotide and/or the RNA molecule are administered daily, weekly, twice a week, three times a week, every two weeks and/or monthly.

The person skilled in the art can estimate repetition rates for dosing based on measured residence times and concentrations of the drug in bodily fluids or tissues. Following successful treatment, it can be desirable to have the subject undergo maintenance therapy to prevent the recurrence of the disease, wherein the composition is to be administered in maintenance doses, for example, ranging from 0.01 µg to 100 g/kg of body weight, once or more daily, to once every 2 years.

In one example, the composition comprising at least one or more oligonucleotides and/or at least one or more RNA molecules, as described, herein can be administered in an concentration or amount of between any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, or 300 mg It is understood that the values provided here refer to values per kilogram body weight of the subject to be treated.

In one example, the at least one or more oligonucleotides and/or the at least one or more RNA molecules can be administered independently or as a combination of each other. In one example, the oligonucleotide and the RNA molecule are to be administered independently of each other in an amount of between any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, or 300 mg. It is understood that the values provided here refer to values per kilogram body weight of the subject to be treated. In one example, the at least one or more oligonucleotides and the at least one or more RNA molecules are to be administered independently of each other in an amount of between about 10 µg/kg to 300 mg/kg body weight.

In one example, the at least one or more oligonucleotides and/or the at least one or more RNA molecules can be administered, independently of each other, in an amount of between any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, or 300 mg. It is understood that the values provided here refer to values per kilogram body weight of the subject to be treated.

In another example, the at least one or more oligonucleotides and/or the at least one or more RNA molecules are administered at a concentration of between 0.1 mg/kg and 10 mg/kg, between 0.1 mg/kg and 5 mg/kg, between 1 mg/kg to 2.5 mg/kg, between 2.5 mg/kg to 5 mg/kg, between 5 mg/kg and 10 mg/kg, between 5 mg/kg and 7.5 mg/kg, between 7.5 mg/kg and 10 mg/kg, at least 1 mg/kg, at least 1.5 mg/kg, at least 1.8 mg/kg, at least 2 mg/kg, at least 2.5 mg/kg, at least 2.8 mg/kg, at least 3 mg/kg, at least 3.2 mg/kg, at least 3.5 mg/kg, at least 4 mg/kg, at least 4.5 mg/kg, at least 5 mg/kg, at least 5.5 mg/kg, at least 6 mg/kg, at least 6.5 mg/kg, at least 7 mg/kg, at least 7.5 mg/kg, at least 8 mg/kg, at least 8.5 mg/kg, at least 9 mg/kg, at least 9.5 mg/kg or at least 10 mg/kg body weight.

As used herein, the term "about", in the context of amounts or concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

In one example, the oligonucleotide and/or the RNA molecule as disclosed herein can be administered either simultaneously or sequentially from each other.

Kits, as disclosed and encompassed herein, can further incorporate a detectable label, such as a fluorophore, radioactive moiety, enzyme, biotin/avidin label, chromophore, chemiluminescent label, or the like, or the kits may include reagents for labelling the nucleic acid primers, the nucleic acid probes or the nucleic acid primers and nucleic acid probes for detecting the presence or absence of at least one mutation as described herein. The primers and/or probes, calibrators and/or controls can be provided in separate containers or pre-dispensed into an appropriate assay format, for example, into micro-titre plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pre-treatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognised that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other embodiments are within the following claims and non-limiting examples. In addition, where features or aspects of the invention are described in terms of Markush groups, those skilled in the art will recognise that the invention is also thereby described in terms of any individual member or subgroup of members of the Markush group.

EXPERIMENTAL SECTION

A Defective Molecular Switch in SCC

Figure 7:
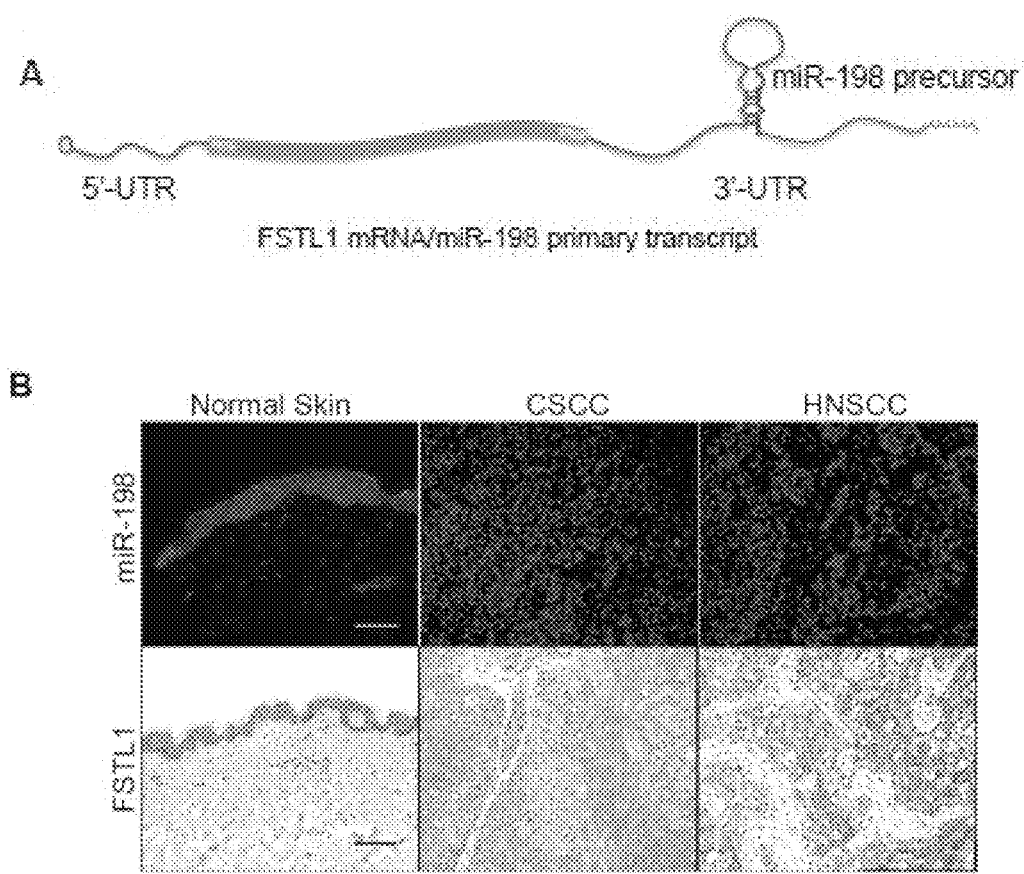
FIG. 7 shows data underlining the presence of a defective molecular switch in SCC. A) Schematic representation of a transcript which functions as FSTL1 mRNA or as primary miR-198 transcript in a context-specific manner. B) Expression of miR-198 detected by in situ hybridization (top panel) and immunohistochemical localization of FSTL1 protein (bottom panel) on normal skin (n=5), CSCC (n=73) and HNSCC (n=64) tissue sections. miR-198 is stained red and nuclei are stained blue (top panel). FSTL1 is stained brown and nuclei are stained blue (bottom panel). C) Immunofluorescence staining of KSRP on normal skin and SCC tissue sections. Compared to the normal skin (n=5), a significant decrease in KSRP protein expression observed in both CSCC (n=73) and HNSCC (n=64) tissue sections (top panel). In situ hybridization with LNA probes specific for mature miR-181a on normal skin (n=5), CSCC (n=73), HNSCC (n=64) tissue sections (bottom panel). Scale bar— 100 µM. D) Western blot detection of KSRP, FSTL1 and β-actin on SCC cells transfected with control or anti-miR-181a. E) Histogram representing miR-198 relative transcript abundance in SCC cells treated with control or antimiR-181a oligonucleotides. Student's t-test was used to calculate P value. Error bars denote mean±s.e.m. *[P<0.05]
Figure 7:
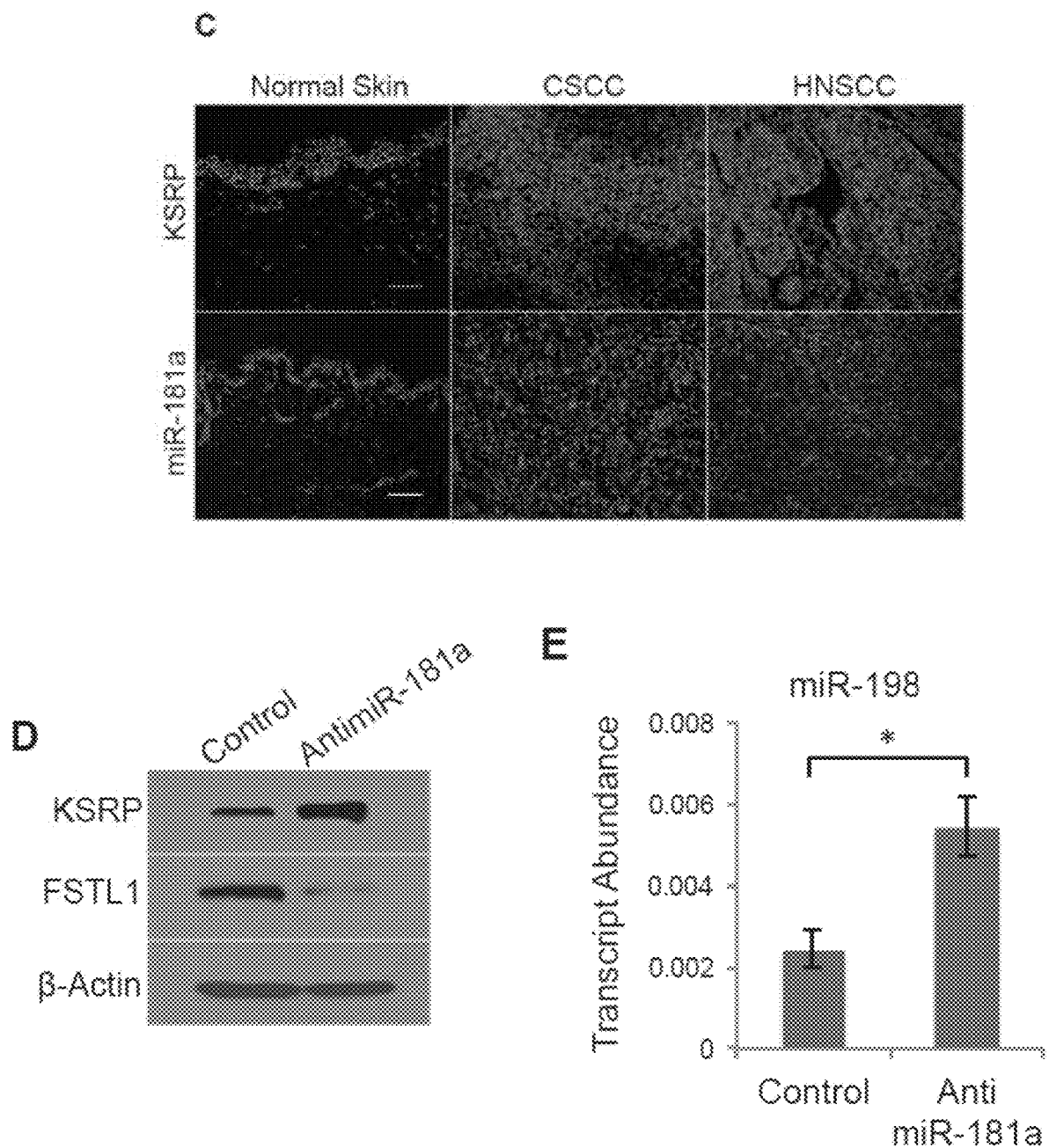

Previously a miR-198/FSTL1 molecular switch had been described, which controls expression of two alternate gene products from a single transcript (FIG. 7A). In normal skin, expression of anti-migratory miR-198 from the 3'-UTR of FSTL1 switches to the expression of pro-migratory FSTL1 protein upon wounding to facilitate keratinocyte migration and wound re-epithelialization. Exploring the molecular mechanisms in parallel between wound healing and progressive SCC, the expression of miR-198 and FSTL1 in CSCC and HNSCC was examined. Fluorescent in situ hybridization using specific probes to detect mature miR-198 revealed very little or no miR-198 in tissue sections from CSCC and HNSCC, compared to the normal skin (FIG. 7B, upper panel). However, immuno-histochemistry with anti-FSTL1 antibodies on CSCC and HNSCC tissue sections revealed sustained expression of FSTL1 protein (FIG. 7B, lower panel). This indicates a prolonged wound-healing phase in SCC. Further, sustained expression of pro-migratory FSTL1 and perpetual absence of anti-migratory miR-198, suggests a defective switch, which potentially enhances cell migration in SCC.

Figure 14:
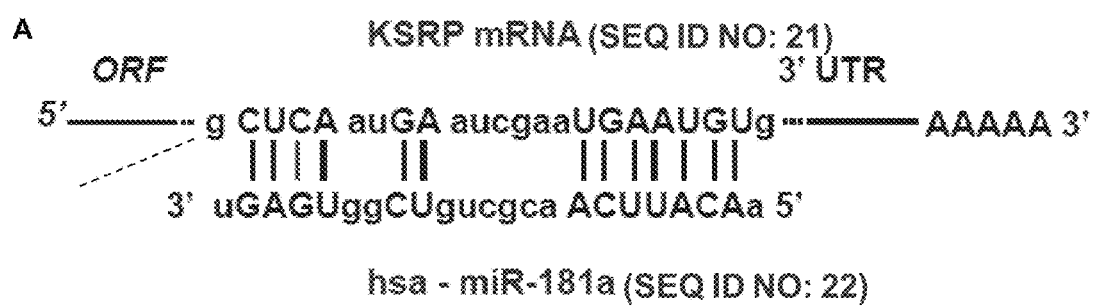
FIG. 14 shows data showing that microRNA miR-181a targets KSRP. A) miR-181a binding site in KSRP mRNA (NM_003685) B) shows a histogram representing miR-181a relative transcript abundance in SCC12 cells treated with control or antimiR-181a oligonucleotides. Student's t-test was used to calculate P value. Error bars denote mean±s.e.m **P<0.001.
Figure 14:
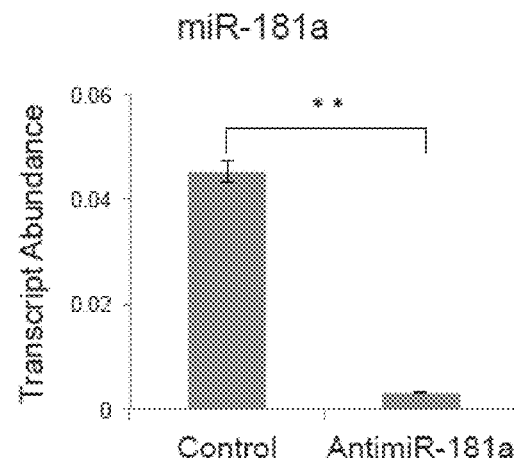

MicroRNA-198 belongs to a small cohort of miRNAs that require KH-type splicing regulatory protein (KSRP) for processing. The absence of miR-198 prompted us to examine the expression of KSRP in SCC. Immunohistochemistry on SCC tissue sections revealed significant down-regulation of KSRP expression compared to normal skin (FIG. 7C, upper panel). The RNA binding protein KSRP is a potential target of microRNA-181a (miR-181a; FIG. 14a). Investigation of SCC tissue sections revealed a significant up-regulation of miR-181a expression (FIG. 7C lower panel) suggesting that KSRP may be a target of miR-181a in SCC. Knockdown of miR 181a using antimiR-181a (FIG. 14b), resulted in a substantial increase in KSRP protein expression (FIG. 7D, top panel) confirming, KSRP is a direct target of miR-181a in SCC. Further, a significant decrease in FSTL1 expression (FIG. 7D, middle panel) with a concomitant increase in miR-198 expression (FIG. 7E) was evident upon knockdown of miR-181a. Together, these results indicate that miR-181a is an upstream regulator of the molecular switch in SCC. Increased aberrant expression of miR-181a suppresses KSRP and in the absence of KSRP, the processing of miR-198 fails, resulting in sustained expression of FSTL1.

EGF-Driven Micro-Circuitry Hijacks the Molecular Switch

Figure 8:
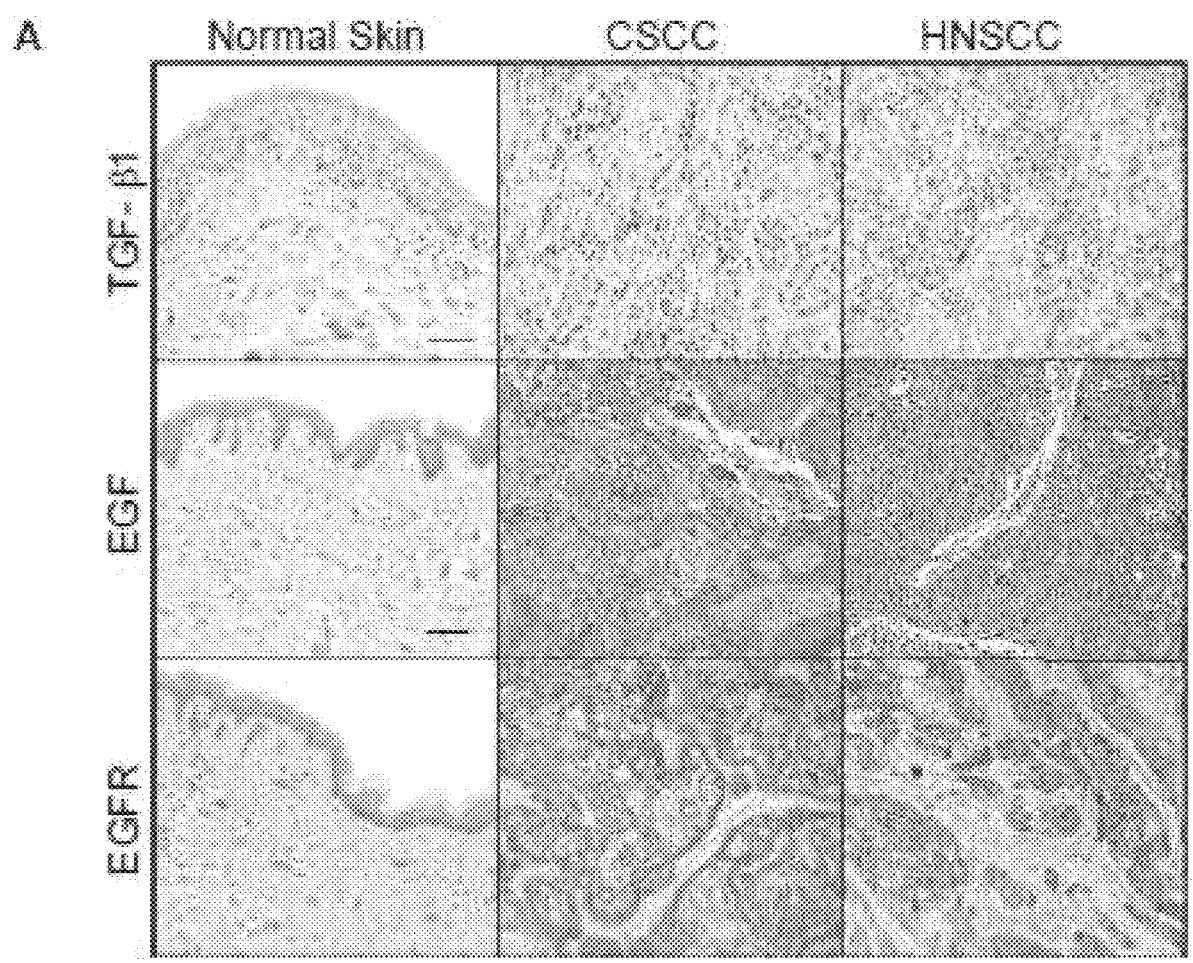
FIG. 8 shows data supporting that the EGF-driven microcircuitry hijacks the molecular switch: A) Detection of TGF-β1 ligand (top panel), EGF ligand (middle panel) and EGFR (bottom panel) by immunohistochemistry in normal skin (n=5), CSCC (n=73) and HNSCC (n=64) tissue sections. Scale bar—50 μM in top panel and 100 μM in middle and bottom panel. B) Histogram representing miR-181a transcript abundance in SCC12 cells treated with EGF alone or EGF & PD153035, a selective inhibitor of EGFR tyrosine kinase. C) Western blot detection of KSRP, FSTL1 and β-actin from SCC cell lysates treated with EGF alone or EGF & PD153035. D) Histogram representing miR-198 transcript abundance in SCC cells treated with EGF alone or EGF & PD153035. Student's t-test was used to calculate P value. Error bars denote mean±s.e.m. (*[P<0.05], **[P<0.001]). E) Schematic representation of EGF-driven microcircuitry which hijacks the molecular switch.
Figure 8:
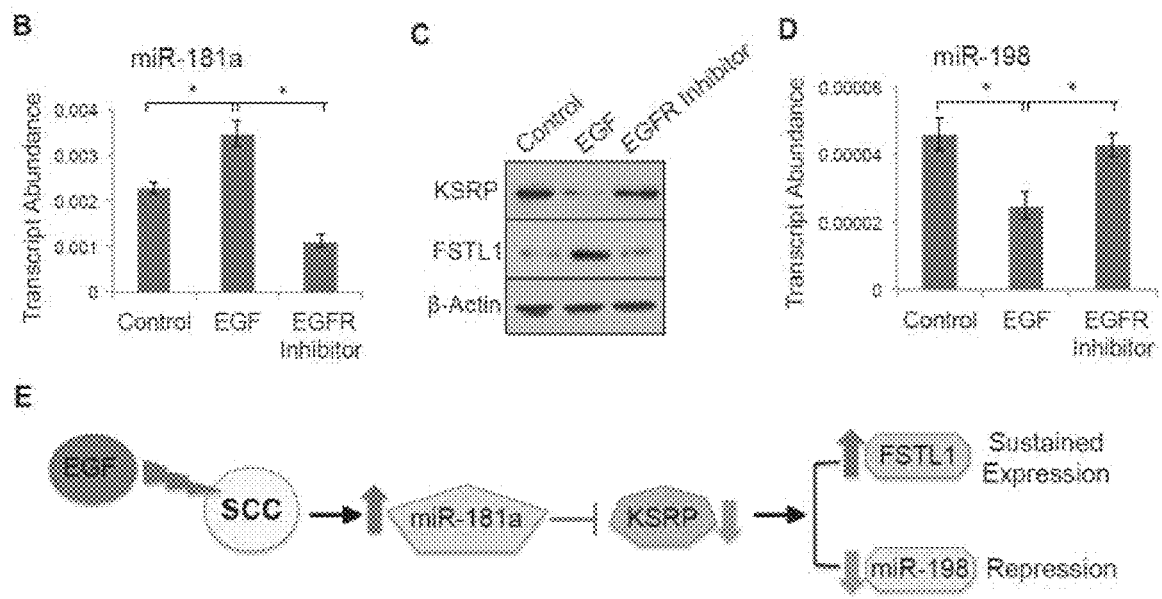

TGF-β-mediated upregulation of oncogenic miR-181a expression is known to promote breast cancer metastasis and induce epithelial-mesenchymal transition (EMT) in hepatocellular carcinoma. Despite aberrant overexpression of miR-181a in CSCC and HNSCC, extremely low levels of TGF-β (FIG. 8A, upper panel) were observed. As EGFR amplification and EGF-induced EMT are well known in SCC, the role of EGF as an upstream regulator of miR-181a was investigated. When compared with normal skin, increased expression of EGF (FIG. 8A, middle panel) and EGFR (FIG. 8A, lower panel) was clearly seen in CSCC and HNSCC tissue sections. Stimulation of SCC12 cells with exogenous EGF resulted in an up-regulation of miR-181a and addition of EGFR inhibitor (PD153035) resulted in down-regulation of miR-181a, confirming the role of EGF as an upstream regulator of miR-181a in SCC (FIG. 8B). Further, down-regulation of KSRP expression with EGF and restoration of KSRP expression with EGFR inhibitor PD153035 (FIG. 8C, upper panel) confirms that EGF is an up-stream regulator of miR-181a in SCC. Finally, treatment with EGF results in an up-regulation of FSTL1 with a concomitant down-regulation of miR-198. Ablation of EGF signalling using EGFR inhibitor reverses this response indicating that, EGF is the master controller of the switch in SCC (FIG. 8C, 8D). This observation was consistent across cell lines from both CSCC and HNSCC. In summary, EGF-driven micro-circuitry hijacks the molecular switch, thus preventing the expression of anti-migratory miR-198 and allows sustained expression of pro-migratory FSTL1 (FIG. 8E).

FSTL1 and DIAPH1 Enhance Migration and Invasion of SCC Cells

Figure 9:
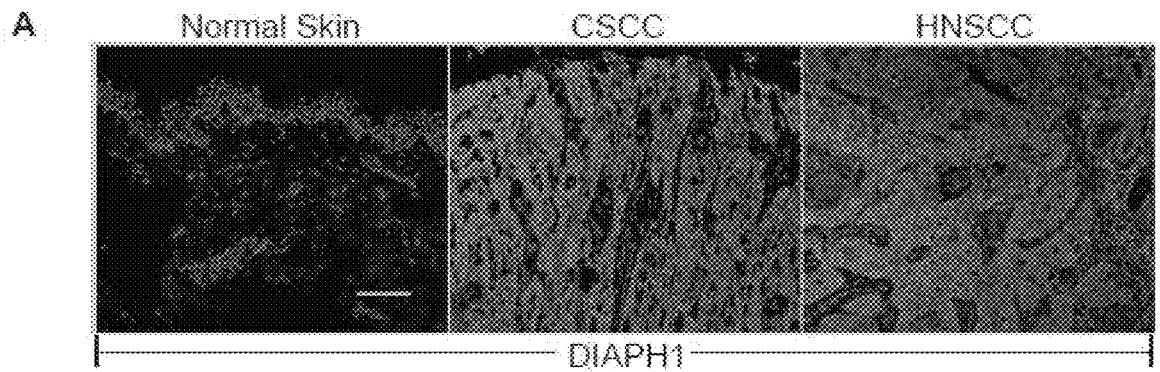
FIG. 9 provides data showing that FSTL1 and DIAPH1 enhance migration and invasion of SCC cells. A) Immunofluorescence staining of DIAPH1 on normal skin and SCC tissue sections. In the absence of miR-198, a significant increase in DIAPH1 is clearly observed in both CSCC (n=73) and HNSCC (n=64) patient samples compared to the normal skin. Scale bar—100 μM B) Morphology of SCC cells with control shRNA or shRNA against FSTL1 or DIAPH1 (top panel) visualized using phalloidin conjugated-TRITC. Knockdown of FSTL1 or DIAPH1 showed a significant difference in morphology compared to control cells. A snap shot of cell trajectory displacement over a period of 24 hours in control, shFSTL1 and shDIAPH1 cells, depicted (bottom panel). C) Analysis of cell displacement in control, shFSTL1 and shDIAPH1 cells. One-way analyses of variants (ANOVA) with Dunnett's multiple correction tests were used to calculate the statistical significance between groups. *P<0.05 P<0.01 D) Organotypic invasion assay with SCC12 cells expressing control shRNA or shRNA against FSTL1 or DIAPH1. SCC12 cells were detected by KRT14 staining (in red). E) Number of cells invading the matrix were counted and plotted as a histogram P<0.001 Error bars represent s.d.
Figure 9:
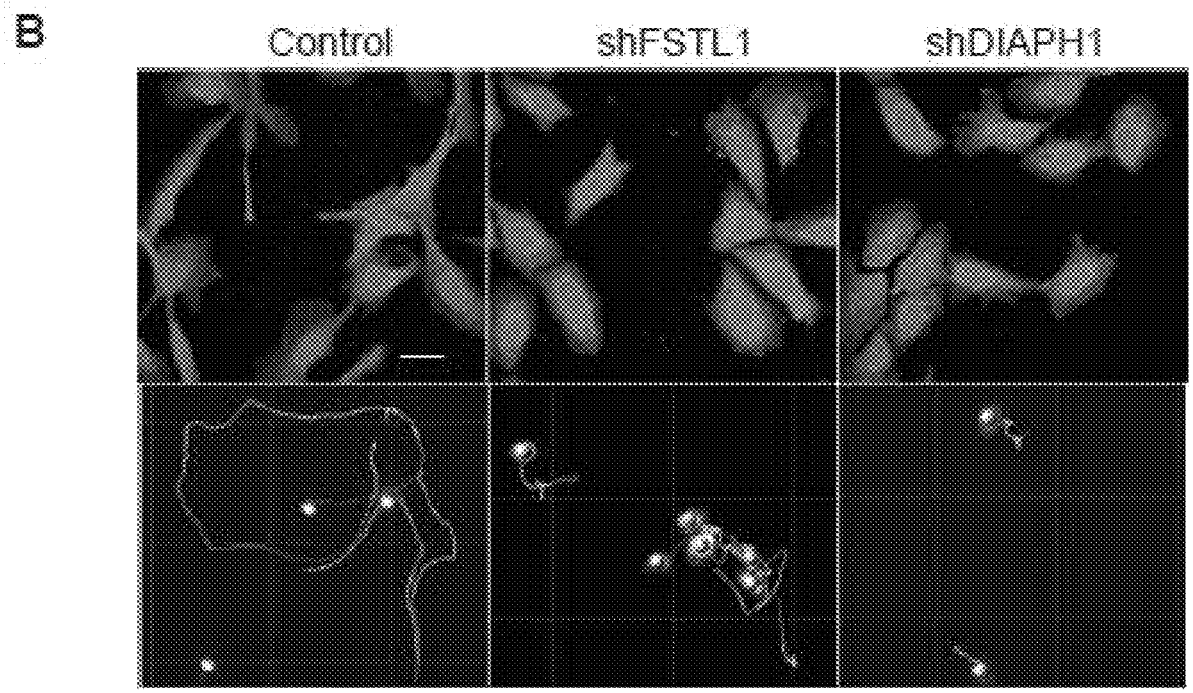
Figure 9:
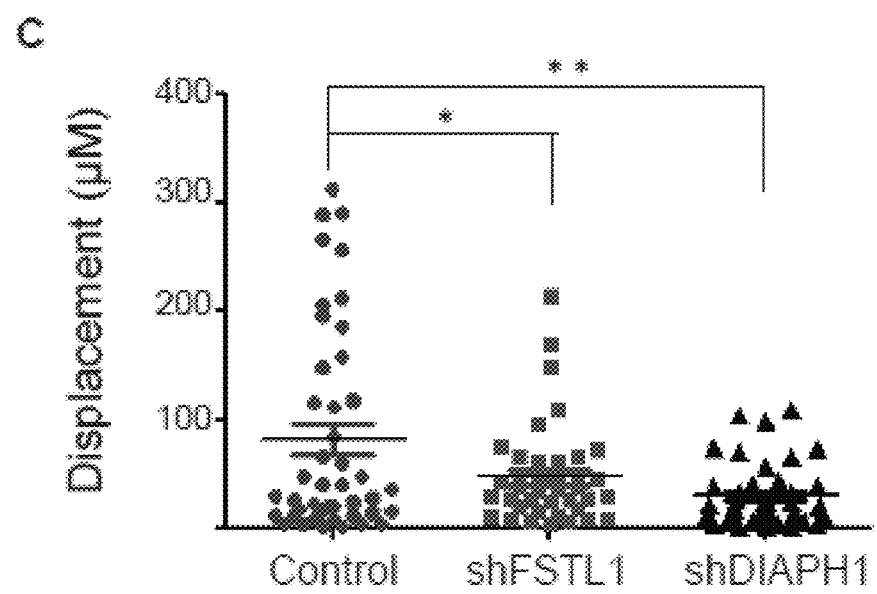
Figure 9:
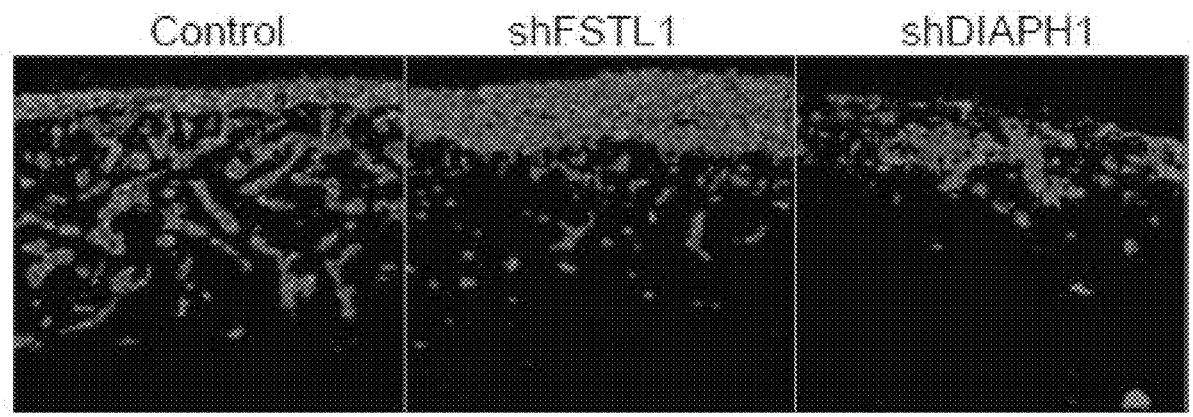
Figure 9:
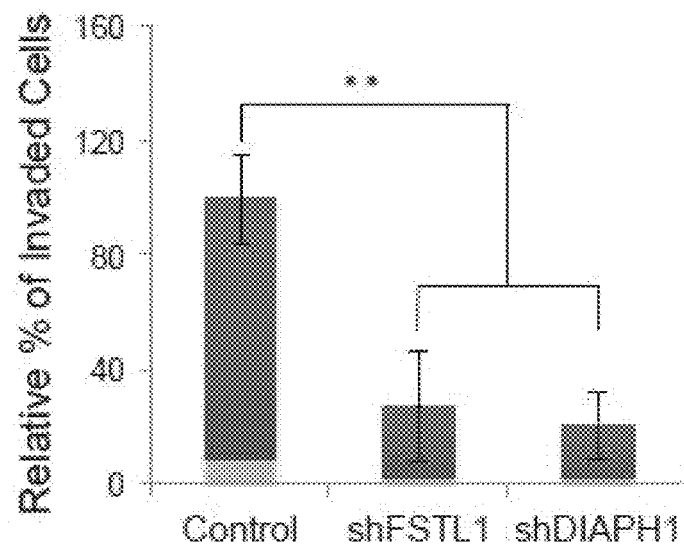

It was then sought to investigate the expression of pro-migratory targets of miR-198 in SCC. Diaphanous homolog 1 (DIAPH1) which is a crucial player in actin polymerization and directed cell migrationis a direct target of miR-198. Immunohistochemistry on CSCC and HNSCC tissue sections using anti-DIAPH1 antibody showed high expression of DIAPH1 (FIG. 9A). Thus, modulating the molecular switch, EGF blocks the expression of anti-migratory miR-198. This results in persistent expression of the pro-migratory target gene, DIAPH1.

Figure 15:
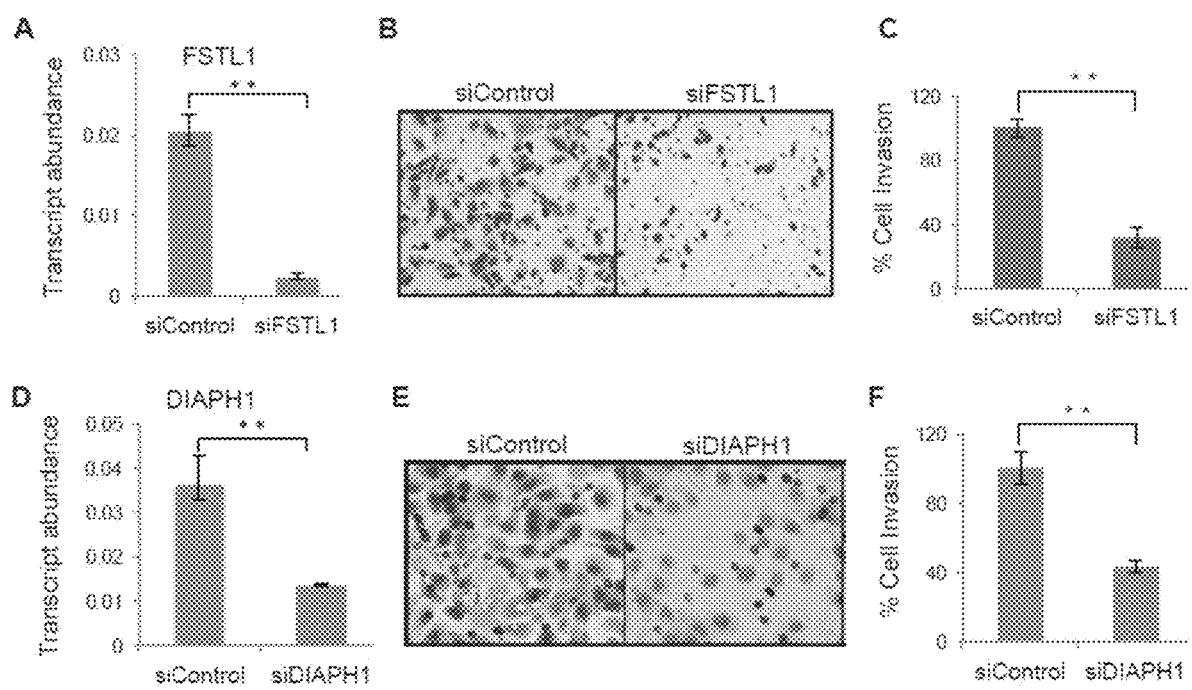
FIG. 15 shows data showing that FSTL1 and DIAPH1 are pro-invasive. A) Relative transcript abundance of FSTL1 in SCC cells transfected with non-targeting siRNA or gene specific siRNAs against FSTL1. B) Boyden chamber invasion assay on these cells show a significant decrease in the number of cells invading the chamber matrix in siFSTL1 compared to control cells. Representative images of migrated cells detected with Giemsa staining. C) Cells were counted from six independent fields and histogram represents relative number of invaded cells. P<0.001 Error bars represent s.d. D) Relative transcript abundance of DIAPH1 in SCC cells transfected with non-targeting siRNA or gene specific siRNAs against DIAPH1. E) Boyden chamber invasion assay on these cells show a significant decrease in the number of cells invading the chamber matrix in siDIAPH1 compared to control cells. Representative images of migrated cells detected with Giemsa staining. F) Cells were counted from six independent fields and histogram represents relative number of invaded cells. P<0.001; error bars represent s.d.
Figure 16:
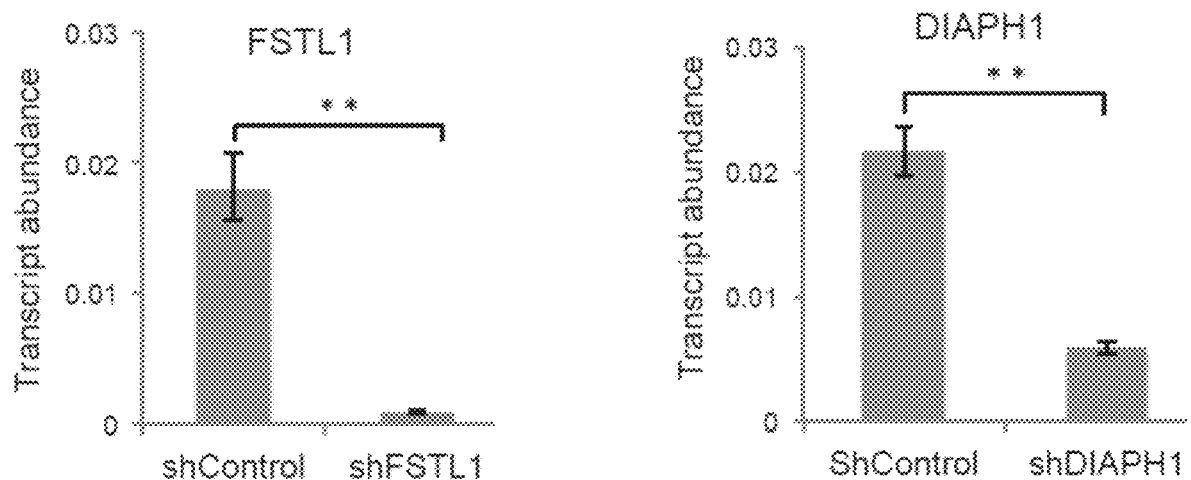
FIG. 16 shows the results of the evaluation of knockdown efficiency for FSTL1 and DIAPH1. Histogram representing FSTL1 (left panel) and DIAPH1 (right panel) transcript abundance in SCC12 cells transduced with control shRNA or shRNA against FSTL1 or DIAPH1. Student's t-test was used to calculate P value. Error bars denote mean±s.e.m. **P<0.001.
Figure 17:
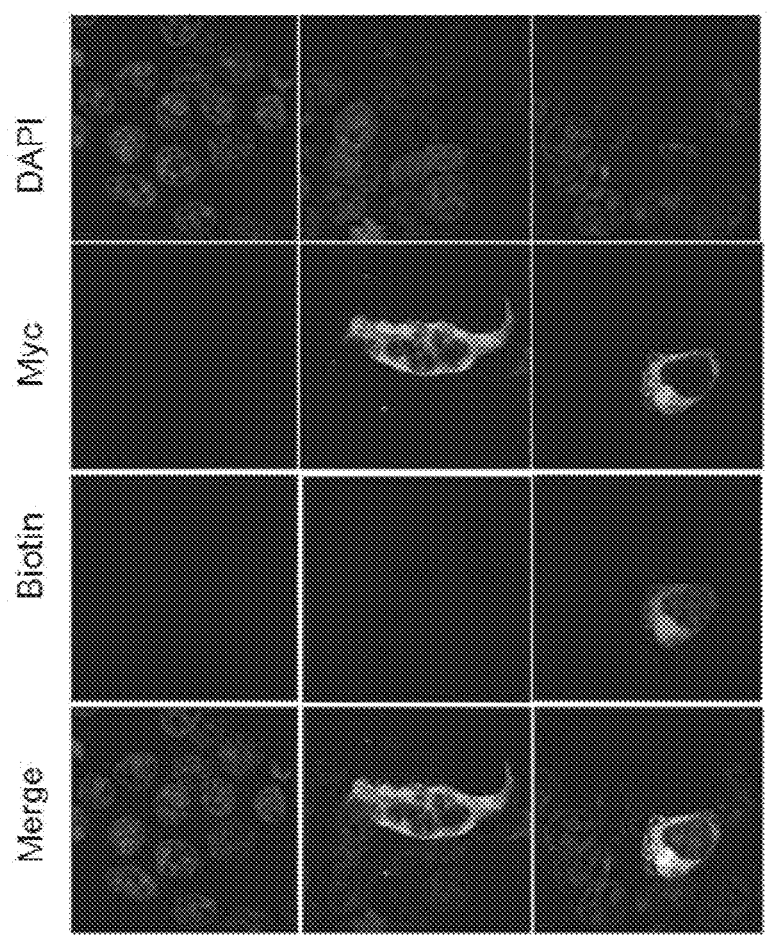
FIG. 17 shows data of the biotinylation of target proteins for BioID. 293T cells were transiently transfected with pTRIPZ vectors expressing DIAPH1 open reading frame, N-terminally fused with BirA*-myc tag under tet-inducble system. Post transfection, cells were either treated with Biotin (50 µM) alone or 10 µg/ml of Dox alone or both. BirA*-DIAPH1 fusion protein expression was probed using an anti-myc antibody, followed by a species-specific secondary antibody coupled to Alexa-488. Biotinylation of target proteins were detected using streptavidin conjugated to Alexa-555.

To investigate the specific role of FSTL1 and DIAPH1, control SCC12 cells, siFSTL1 or siDIAPH1 cells were subjected to Boyden chamber trans-well assay, after evaluation of knockdown efficiency (FIG. 152A, 152D). Following trans-well migration, cells attached to the lower surface of the filters were counted. Transient knockdown of FSTL1 or DIAPH1 leads to a significant decrease in cell migration with a ratio of 37.45±3.65% and 34.23±2.88% respectively compared to the control SCC12 cells (FIG. 15). Further, constitutive knockdown of FSTL1 or DIAPH1 using specific shRNA against FSTL1 or DIAPH1 (FIG. 16), results in a transition from mesenchymal to epithelial phenotype (FIG. 9B, upper panel). Live cell imaging to track the cellular trajectory over a 24 hour time period revealed a significant decrease in cell migration with the loss of FSTL1 or DIAPH1 (FIG. 9B, lower panel, 9C). As a final confirmation, control SCC12 cells, shFSTL1 and shDIAPH1 cells were subjected to a 3-dimensional organotypic assay that mimics in vivo stromal invasion. Knockdown of FSTL1 or DIAPH1 results in a considerable decrease in the number of cells invading the matrigel compared to control SCC12 cells (FIG. 9D, 9E). These results indicate, that sustained expression of FSTL1 and DIAPH1, potentially enhance migration and invasion of carcinoma cells.

FSTL1 and DIAPH1 Promote Metastatic Colonization

Figure 10:
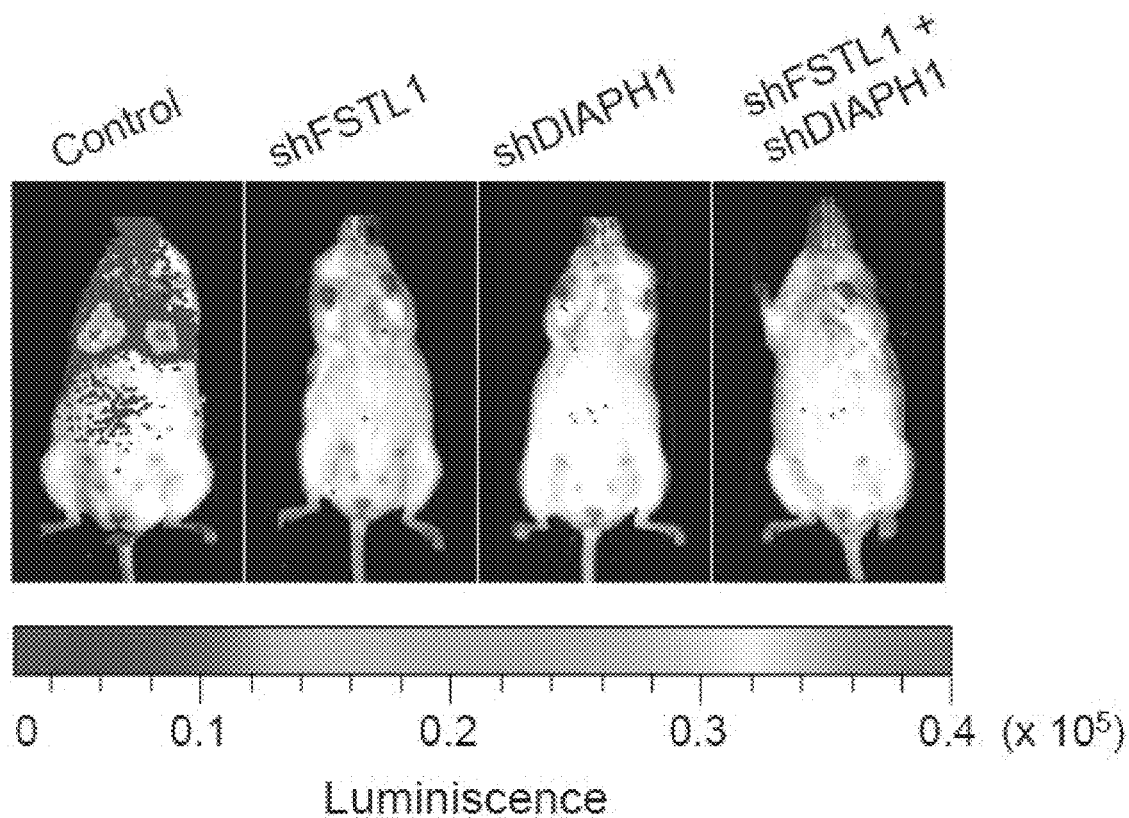
FIG. 10 provides data showing that FSTL1 and DIAPH1 promote metastatic colonization. A) Bioluminescence imaging of systemic metastasis by A253 cells expressing luciferase reporter and control shRNA or shRNA against FSTL1 or DIAPH1 individually or in combination (n=7). B) Bioluminescence quantification of lung metastasis by HNSCC cells. C) Lungs were extracted on day-26 and stained for KRT5 expression and representative images of lung metastatic colonies shown. D) Representation of the total number of metastatic foci in lung sections **P<0.001.
Figure 10:
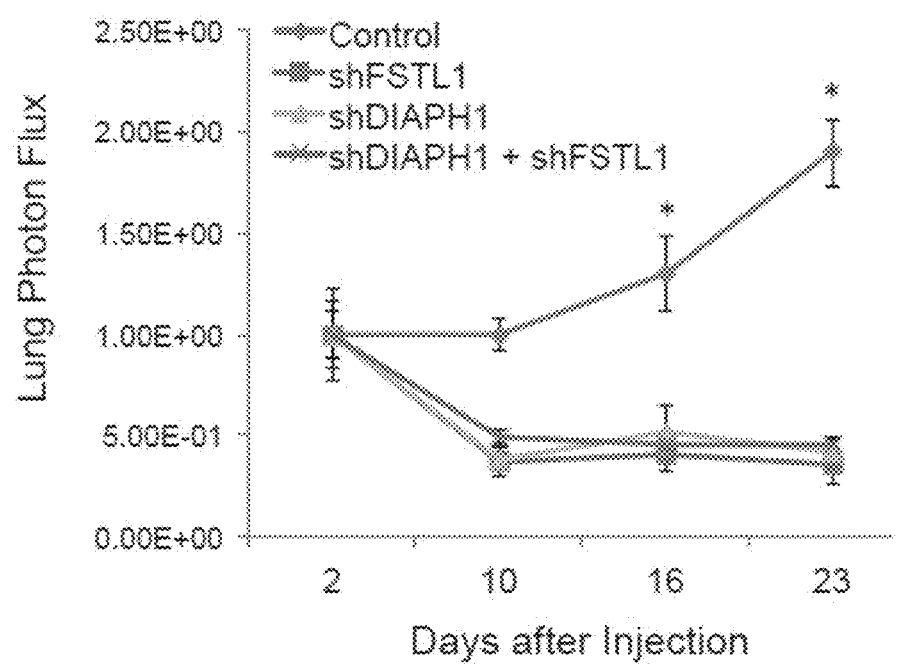
Figure 10:
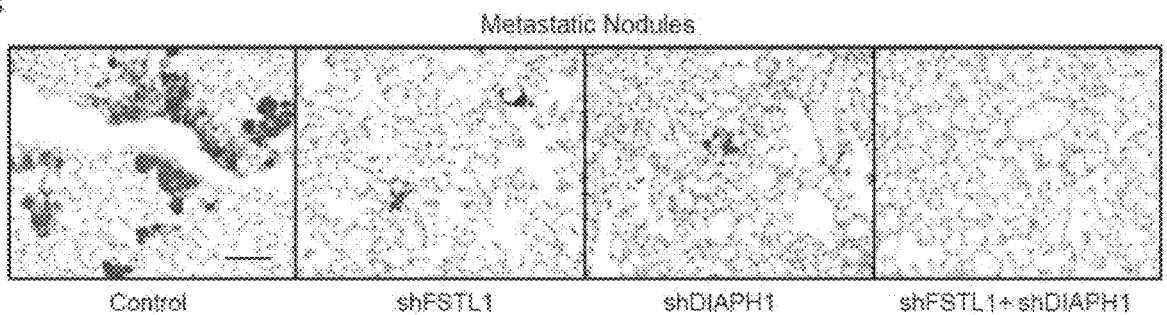
Figure 10:
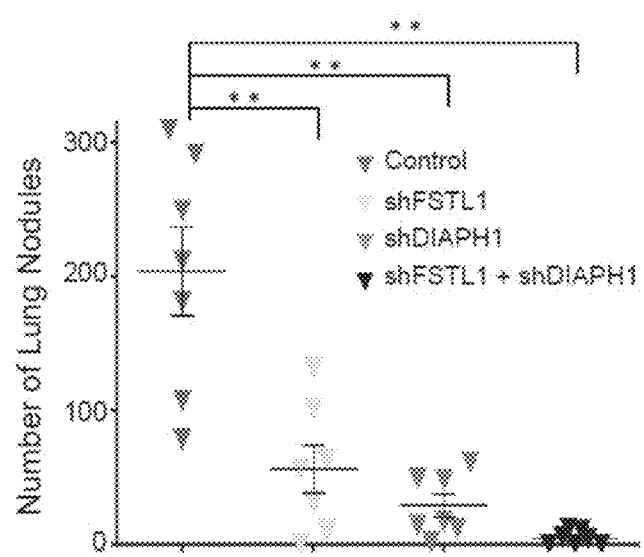

It was then sought to determine the role of FSTL1 and DIAPH1 in metastatic progression of carcinoma. Genetically modified, luciferase expressing, HNSCC cell line (A253 cell line) were transduced with lentivirus encoding shFSTL1 or shDIAPH1 individually or in combination. Cells were implanted in immunodeficient NSG mice by lateral tail vein injections and evaluated for metastatic colonization. Silencing of FSTL1 or DIAPH1 independently decreased lung colonization significantly compared to the control cells (FIGS. 10A and B). Histological quantification revealed a substantial decrease in the total number of metastatic colonies upon knockdown of FSTL1 or DIAPH1 (FIGS. 10C and D). Remarkably, concurrent knockdown of FSTL1 and DIAPH1, results in a significant decrease in the number of lung colonies with no visible colonies in majority of the mice (FIGS. 10C and D, P value<0.001). Taken together, these results suggest that FSTL1 and DIAPH1 are essential for metastasis and highlight the importance of the synergistic gene-pair, FSTL1-DIAPH1 in metastatic colonization.

Prognostic Significance of the Synergistic Gene-Pair FSTL1-DIAPH1

Figure 11:
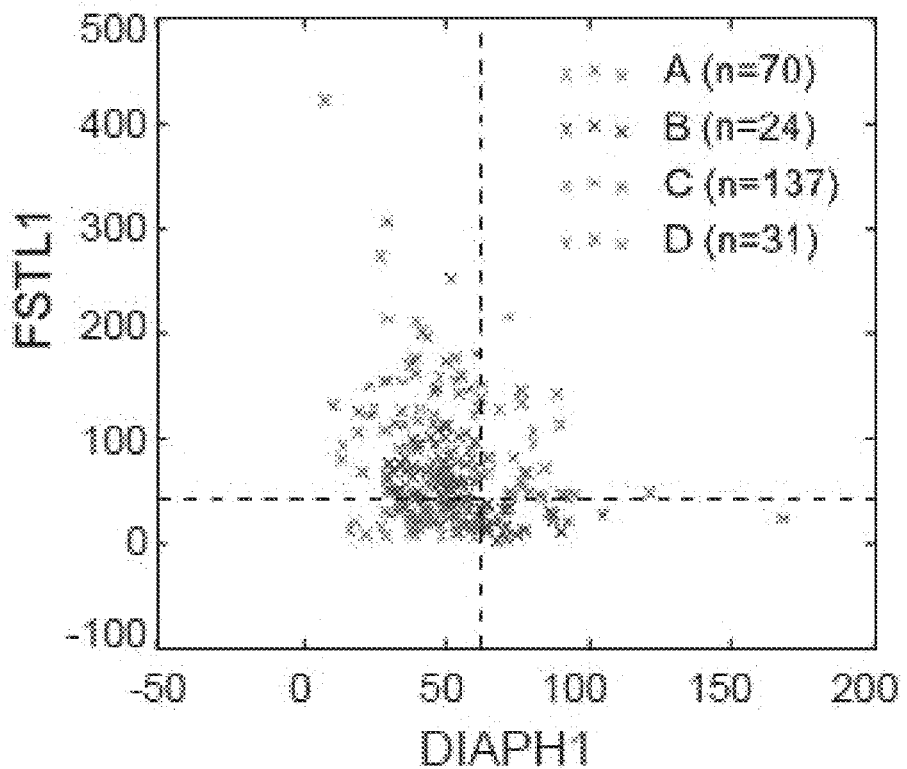
FIG. 11 provides data showing the prognostic significance of the synergistic gene-pair: FSTL1-DIAPH1. A) Scatter plot of FSTL1 and DIAPH1 expressions in 262 patients. The patients were classified into four segments based on two-dimensional data-driven grouping (2D-DDg) method. B) Panel shows the Kaplan Mayer survival curves for the individual segments A, B, C and D (A: Patients with neither DIAPH1 or FSTL1 expression, B: Patients with higher expression of DIAPH1 alone, C: Patients with higher expression of FSTL1 alone, D: Patient group expressing both FSTL1 and DIAPH1). The statistical significance was assessed via the log-rank test. C) Scatter plot of FSTL1 and DIAPH1 expressions in 262 patients as in plot A, with common colour coding for three segments ABC grouped as low risk D) Kaplan-Meier survival curves of the low risk patients (corresponding to segment ABC) and high-risk patients (corresponding to segment D). The statistical significance was assessed via the log-rank test (P=0.000061).
Figure 11:
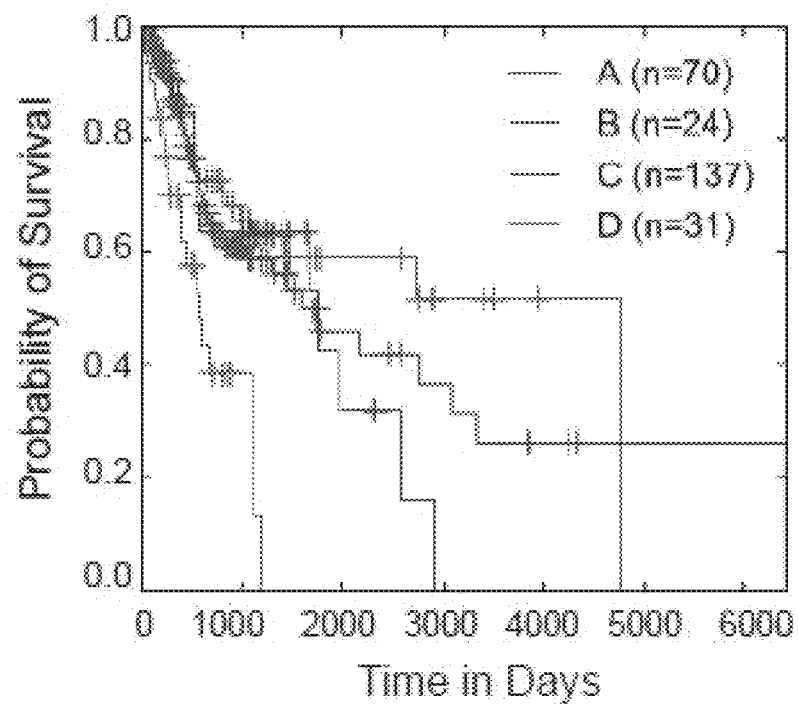
Figure 11:
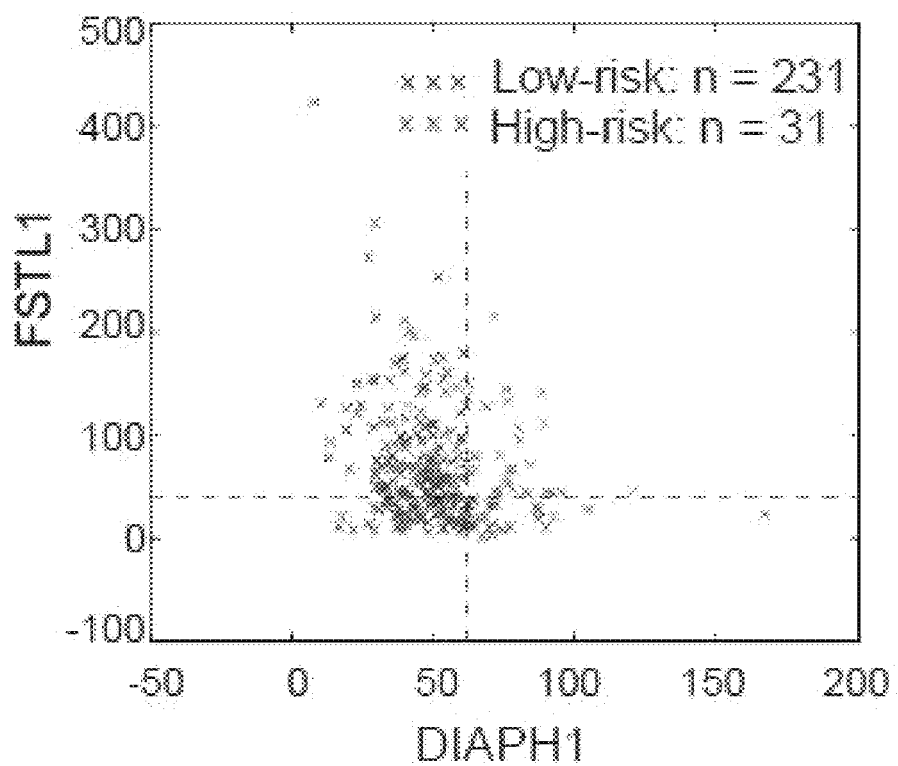
Figure 11:
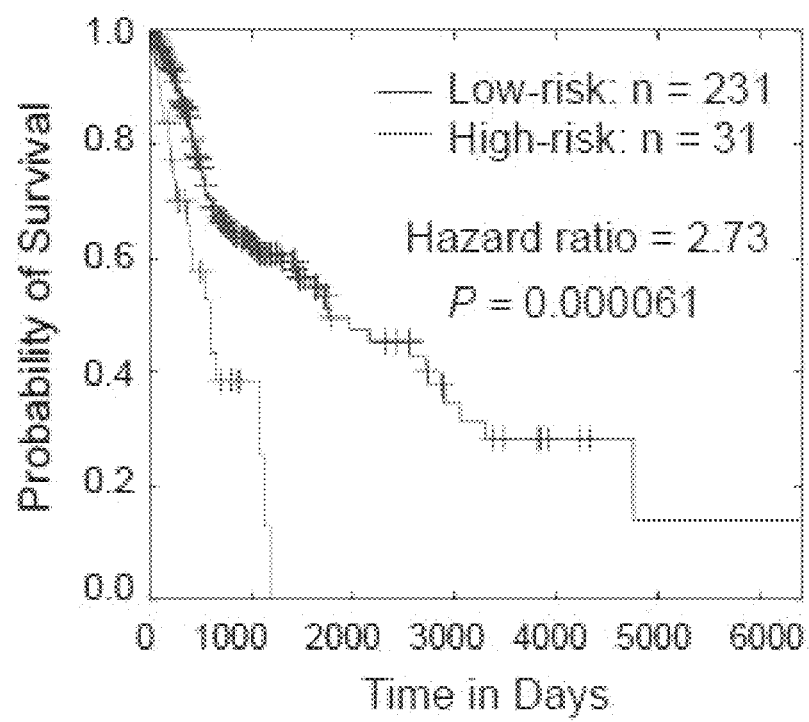

The data from 262 HNSCC patients in the TCGA database was interrogated, generating conventional Kaplan-Meier survival curves to compare their overall survival. Here, a 2-dimensional data-driven grouping (2D-DDg) method that can identify expression cut-offs on a two-dimensional axis was used to stratify the patient cohort into significant survival subgroups. The patients were classified into four segments based on a 2D-DDg method (FIGS. 11A and 11B). The results indicate that FSTL1 and DIAPH1 individually exhibit oncogenic behaviour (FIGS. 11A and B) however, when combined, the prognostic features of the gene-pair generates a robust patient stratification with a log rank p-value=0.000061 (FIGS. 11C and D).

Figure 12:
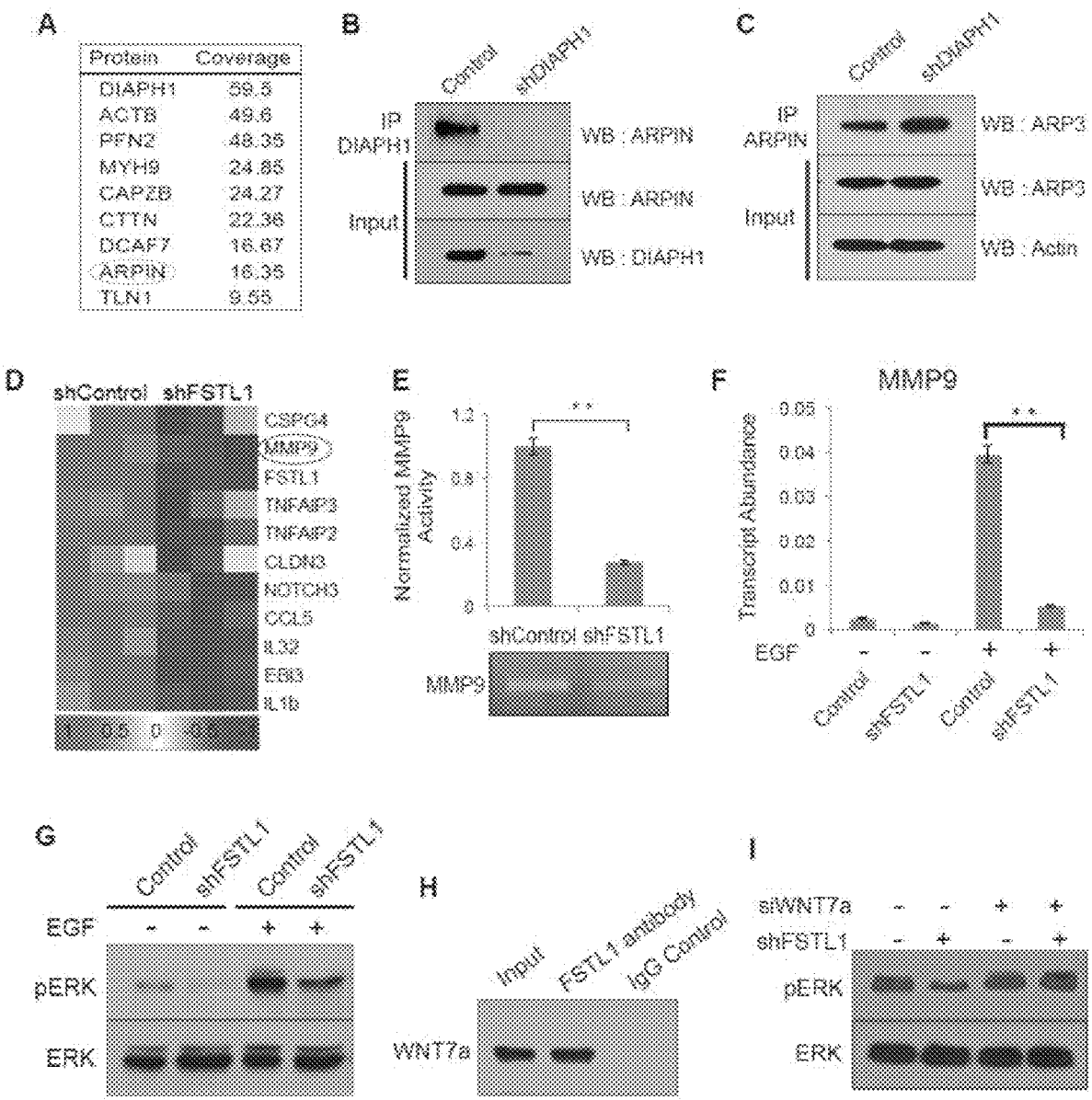
FIG. 12 provides data showing how, mechanistically, DIAPH1 and FSTL1 promote metastasis by sequestering ARPIN and Wnt7a respectively: A) List of selected candidate interacting partners of DIAPH1 shortlisted from BioID based on peptide coverage. B) SCC cell lysates from control or shDIAPH1 cells were subjected to immunoprecipitation with anti-DIAPH1 antibody and immunoprecipitates were probed for ARPIN by western blot analysis (top panel). Input cell lysates were probed for ARPIN (middle panel) and DIAPH1 (lower panel). C) A253 cell lysates from control or shDIAPH1 cells were subjected to immunoprecipitation with anti-ARPIN antibody and immunoprecipitates were probed for Arp3 by western blot analysis (top panel). Input cell lysates were probed for Arp3 (middle panel) and β-actin (lower panel). D) Gene expression values of selected genes from microarray data of SCC12 cells transfected with control non-targeting shRNA or shRNA against FSTL1 represented as a heat-map. Expression values displayed in shades of red (high) or blue (low) relative to the individual mean value of the gene in linear scale. E) Gelatin zymography was performed with equal amount of cell culture supernatant from A253 cells transduced with control shRNA or shRNA against FSTL1. Quantification of band intensities form three independent experiments represented as a histogram (top panel). P<0.001 Error bars represent s.d. F) Control or shFSTL1 A253 cells were pre-treated with 30 ng/ml of EGF. Histogram represents the relative transcript abundance of MMP9 in these samples.P<0.001 Error bars represent s.e.m. G) Western blot analysis on A253 cell lysates from control or EGF pre-treated cells. Lysates were probed for phosphoERK or total ERK. H) A253 cell lysates were subjected to immunoprecipitation with IgG or anti-FSTL1 antibody and immunoprecipitates along with input lysate were probed for Wnt7a by western blot analysis. I) A253 cells transduced with control or shFSTL1 were subjected to transfection with specific siRNA against Wnt7a. Post transfection, cells were treated with EGF to stimulate ERK phosphorylation. Cell lysates were probed for phosphoERK or total ERK by western blot analysis.
Figure 18:
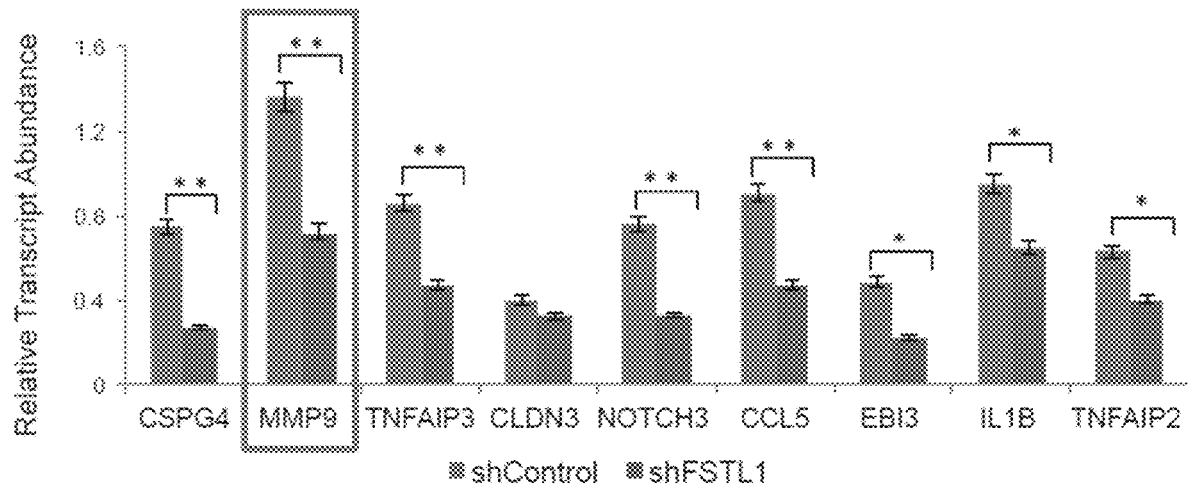
FIG. 18 shows column graphs summarizing the results of the validation of microarray data. Histogram representing relative transcript abundances (control versus FSTL1 knockdown) of selected genes identified from microarrays (FIG. 12d) and validated by qRT-PCR. Results show significant correlation with microarray data. Student's t-test was used to calculate P value and error bars denote mean±s.e.m. *P<0.05, **P<0.001.
Figure 19:
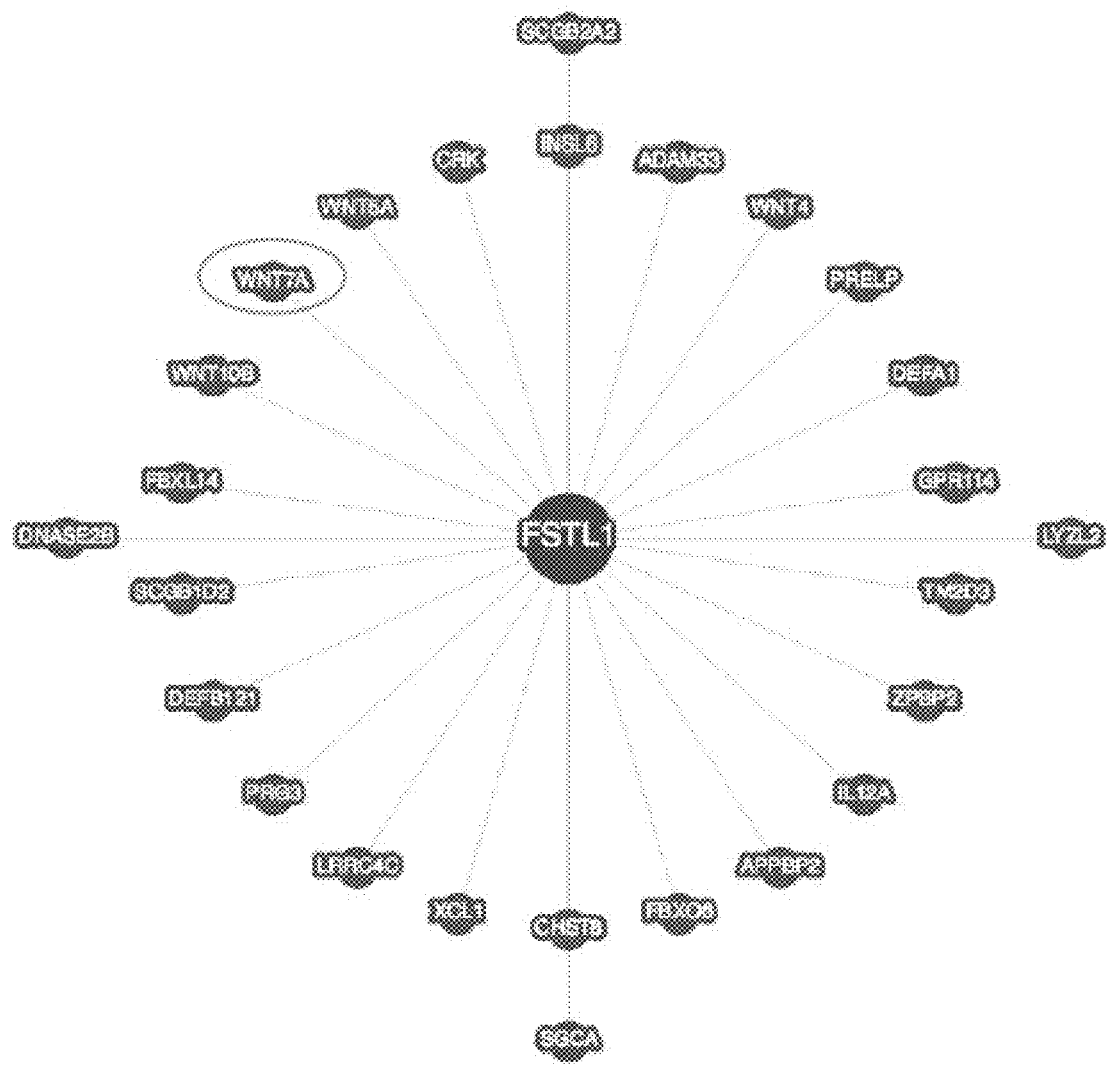
FIG. 19 shows a schematic snap shot of the BioGRID Network Analysis. This is a snap shot of proteins predicted to interact with FSTL1 protein from BioGRID version 3.4.134 showing 26 unique interacting partners.

Mechanistically DIAPH1 and FSTL1 Promote Metastasis by Sequestering ARPIN and Wnt7a Respectively To understand the mechanism by which DIAPH1 enhances metastasis, BioID (Proximity-dependent biotin identification) analysis was performed to identify candidate proteins that interact with DIAPH1 (FIG. 18). Among the several candidates that interact with DIAPH1, ARPIN was identified as a novel potential interacting partner (FIG. 12A). ARPIN is a negative regulator of cell migration which blocks association of Arp2/3 complex with other nucleating factors and inhibits cell migration. To investigate the interaction of DIAPH1 with ARPIN, cellular lysates from control or shDIAPH1 A253, cells were subjected to immuno-precipitation (IP) with anti-DIAPH1 antibody and the immunoprecipitates were probed for ARPIN by western blot analysis. Enrichment of ARPIN only in control samples, but not in DIAPH1 depleted samples, confirmed the specific interaction of ARPIN with DIAPH1 (FIG. 12B). It was hypothesized, that DIAPH1 interacts and sequesters ARPIN to prevent its interaction with Arp3 (a component of Arp2/3 complex) thus, enhancing polarized cell migration in SCC. To validate this hypothesis, cellular lysates from control or shDIAPH1 A253 cells were further subjected to immuno-precipitation with anti-ARPIN antibody, and the immunoprecipitates were probed for Arp3 by Western blot analysis. Significant enrichment of Arp3 in DIAPH1 depleted samples compared to control samples, highlight the role of DIAPH1 in sequestering ARPIN, thus preventing the interaction of ARPIN with Arp3 (FIG. 12C). In conclusion, DIAPH1 sequesters ARPIN, which is a competitive inhibitor of Arp2/3 complex and promotes incessant migration of carcinoma cells. Next, the mechanism by which FSTL1 promotes invasion and metastasis in SCC was investigated. Transcriptome analysis revealed that knockdown of FSTL1 in SCC cells results in a significant down-regulation of extracellular matrix (ECM) degrading enzyme, matrix metalloproteinase 9 (MMP9) (FIG. 12D, 18). Moreover, a decrease in the activity of MMP9 upon FSTL1 knockdown suggests, that FSTL1 may be an up-stream regulator of MMP9 expression (FIG. 12E). EGF stimulates the expression of ECM-degrading protease MMP9, through extracellular signal-regulated kinase (ERK) pathway. Further, EGF hijacks the molecular switch and enables sustained expression of FSTL1. Linking these findings, it was hypothesized that FSTL1 is a potential up-stream regulator of EGF-mediated MMP9 expression in SCC. To verify this hypothesis, control or shFSTL1 A253 cells were treated with 30 ng/ml of EGF. qRT-PCR analysis clearly indicates that, EGF-mediated up-regulation of MMP9 fails to occur in the absence of FSTL1, confirming that FSTL1 is essential for EGF-mediated MMP9 expression (FIG. 12F). As EGF regulates MMP9 expression, by activating the ERK, the cell lysates from EGF-treated, control or shFSTL1 A253 cells were probed for the expression of ERK or phosphoERK. Loss of FSTL1 results in a significant reduction in EGF-mediated phosphorylation of ERK (FIG. 12G). Taken together these results emphasize the role of FSTL1 as an upstream regulator of MMP9 expression in SCC. Next, it was asked how a secreted glycoprotein, FSTL1, regulates MMP9 expression. To identify the potential effectors of this regulation, the Biological General Repository for Interaction Datasets (BioGRID), a database containing experimentally validated protein-protein interactors, was screened. BioGRID analysis revealed 26 potential interacting partners of FSTL1, which include Wnt4, Wnt5a, Wnt7a and Wnt10b (FIG. 19). To identify specific interactors of FSTL1, cell lysates from A253 cells were subjected to immunoprecipitation with anti-FSTL1 antibody or IgG control and the immunoprecipitate was probed for Wnt4, Wnt5a, Wnt7a and Wnt10b by Western blot analysis. Detection of significant enrichment of Wnt7a confirmed its specific interaction with FSTL1 (FIG. 12H). Wnt7a inhibits EGF signalling, and suppress tumour cell invasion although, the precise mechanism is still not clear.

Figure 13:
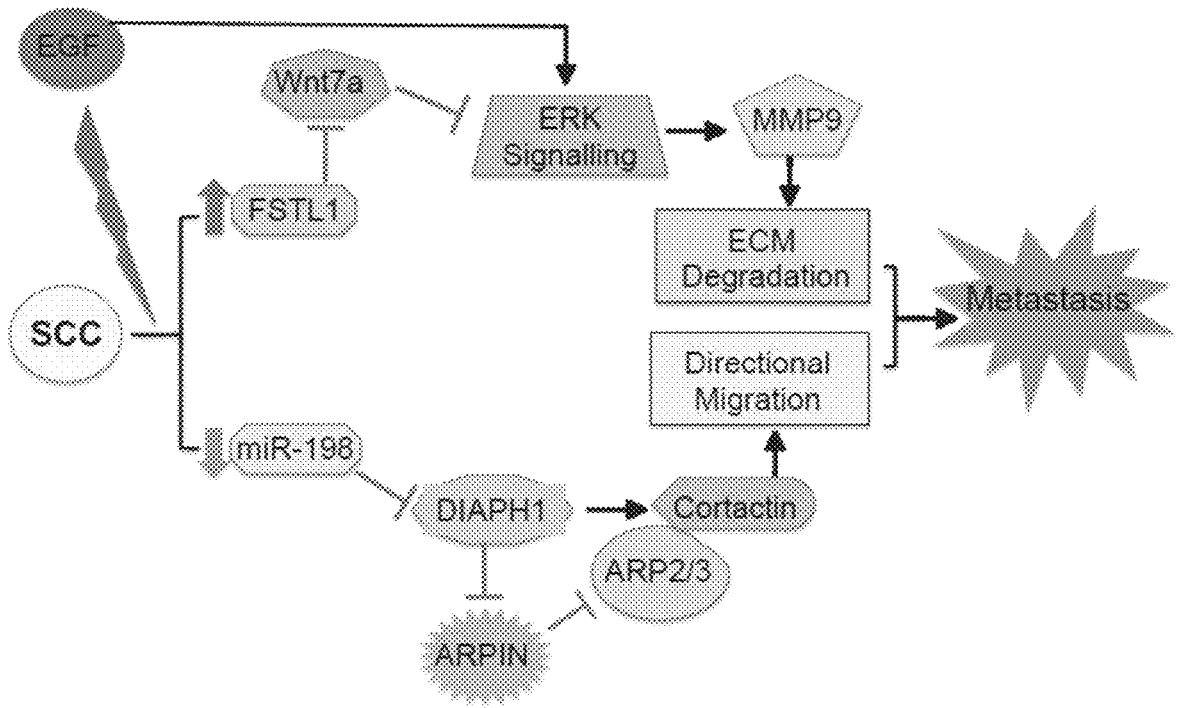
FIG. 13 a schematic of how EGF-driven micro-circuitry hijacks the molecular switch, and steers a two-pronged pathway towards metastasis: Model depicting hijack of miR-198/FSTL1 molecular switch by EGF, which restricts expression of miR-198 allowing sustained expression of FSTL1. This results in a two-pronged pathway towards metastasis.
Figure 20:
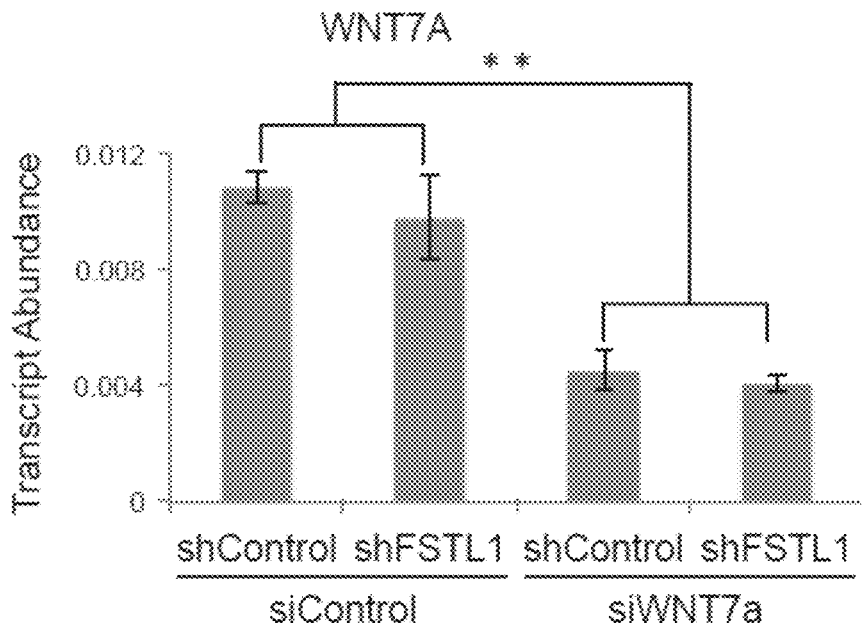
FIG. 20 shows column graphs showing results of the knockdown of WNT7a using gene-specific siRNA. SCC cells expressing control shRNA or shFSTL1, were transfected with non-targeting control siRNA or with gene-specific siRNA against WNT7A. Depicted is the histogram representing relative transcript abundance of WNT7A mRNA. Student's t-test was used to calculate P value. Error bars denote mean±s.e.m. **P<0.001.

To understand the role of Wnt7a in SCC, A253 cells transduced with control or shFSTL1 RNA, were subjected to transfection with specific siRNA against Wnt7a (FIG. 20). Post transfection, cells were treated with EGF to stimulate ERK phosphorylation. Knockdown of FSTL1, results in inhibition of ERK phosphorylation, on the contrary knockdown of Wnt7a results in restoration of ERK phosphorylation (FIG. 12I). These results suggest, that contrary to FSTL1, Wnt7a is an inhibitor of EGF-mediated ERK phosphorylation in SCC. However, concurrent knockdown of FSTL1 and Wnt7a, does not affect the phosphorylation of ERK (FIG. 12I). In conclusion, all the above results suggest that FSTL1 antagonizes Wnt7a and allows perpetual EGF-mediated phosphorylation of ERK. By precluding Wnt7a, which is a negative regulator of EGF-ERK-MMP9 cascade, FSTL1 enhances invasion and metastasis of carcinoma cells (FIG. 13).

EGF-Driven Micro-Circuitry Hijacks the Wound Healing Switch

In normal skin, expression of anti-migratory miR-198 from the 3'-UTR of FSTL1 switches to the expression of pro-migratory FSTL1 protein upon wounding to facilitate keratinocyte migration and wound re-epithelialisation. The miR-198/FSTL1 wound healing switch controls expression of two alternate gene products from a single transcript (FIG. 1A). Exploring the molecular mechanisms in parallel between wound healing and progressive squamous cell cancer, the expression of miR-198 and FSTL1 was analysed in head and neck small cell cancer (HNSCC). Fluorescent in situ hybridisation using specific probes to detect mature miR-198 revealed very little or no miR-198 in tissue sections from HNSCC, compared to the normal tongue tissue (FIG. 1B, upper panel).

Figure 21:
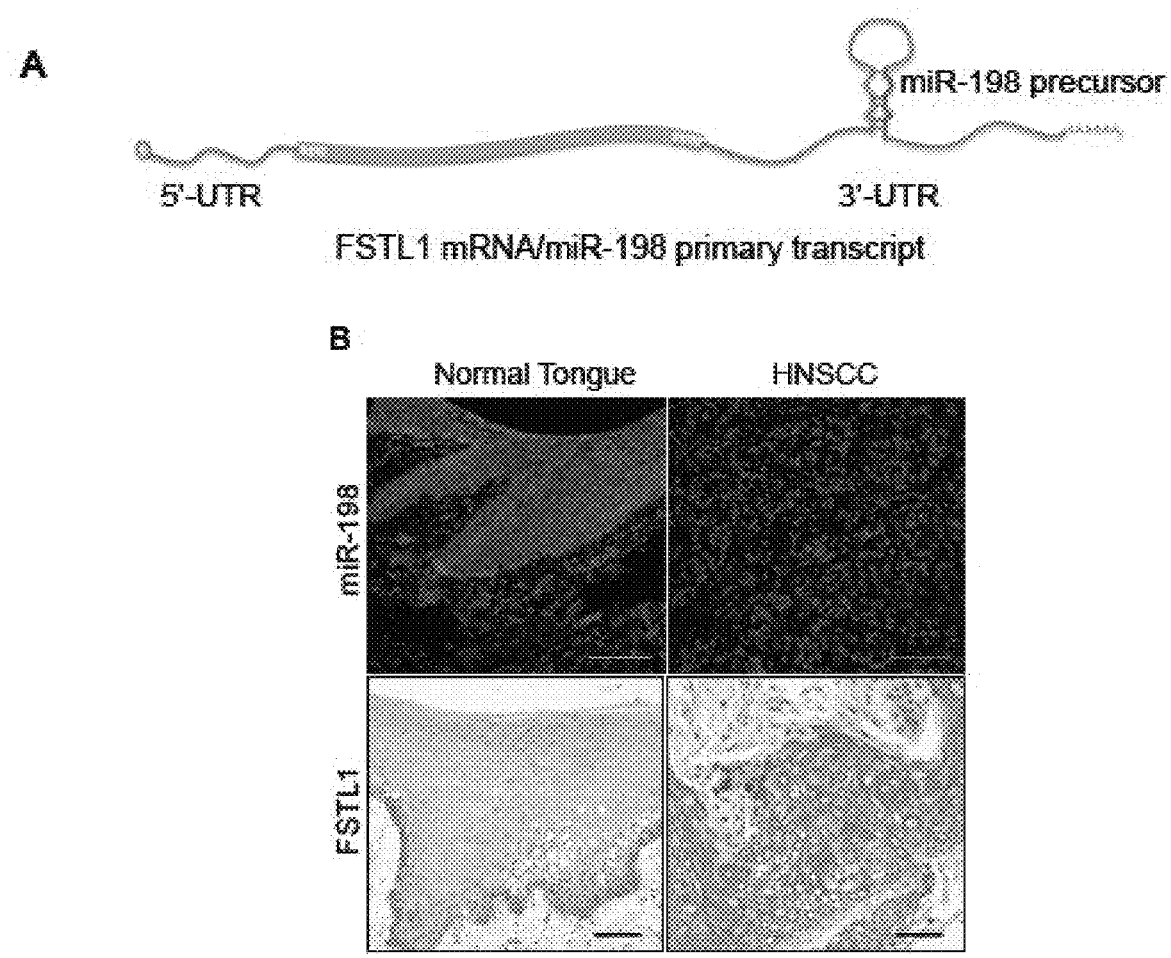
FIG. 21 shows how EGF-driven micro-circuitry hijacks the wound healing switch. A) shows a schematic representation of a transcript which functions as FSTL1 mRNA or as primary miR-198 transcript in a context-specific manner. B) Expression of miR-198 detected by in situ hybridization (top panel) and immunohistochemical localization of FSTL1 protein (bottom panel) on normal tongue (n=5) and HNSCC (n=64) tissue sections. miR-198 is stained red and nuclei are stained blue (top panel). FSTL1 is stained brown and nuclei are stained blue (bottom panel). C) Histogram representing relative transcript abundance of miR-198 in A253 cells treated with EGF as measured by qRT-PCR. D) Immunocytochemistry staining using FSTL1 and KSRP specific antibody on A253 cells treated with EGF. E) miR-181a binding site in KSRP mRNA (NM_003685). F) Histogram representing relative transcript abundance of miR-181a in A253 cells treated with EGF as measured by qRT-PCR. G) Immunofluorescence staining of KSRP on normal tongue (n=5) and HNSCC (n=64) tissue sections (top panel). Compared to the normal tongue, a significant decrease in KSRP protein expression observed in HNSCC tissue sections. In situ hybridization with LNA probes specific for mature miR-181a on normal tongue (n=5) and HNSCC (n=64) tissue sections (bottom panel). H) Western blot detection of KSRP, FSTL1 and β-actin on SCC cells transfected with control or antimiR-181a. I) Histogram representing miR-198 relative transcript abundance in SCC cells treated with control or antimiR-181a oligonucleotides. Student's t-test was used to calculate p value. Error bars denote mean±s.e.m. *[p<0.05]. Scale bar: 100 µM. J) Schematic representation of the EGF-driven micro-circuitry which hijacks the molecular switch.
Figure 21:
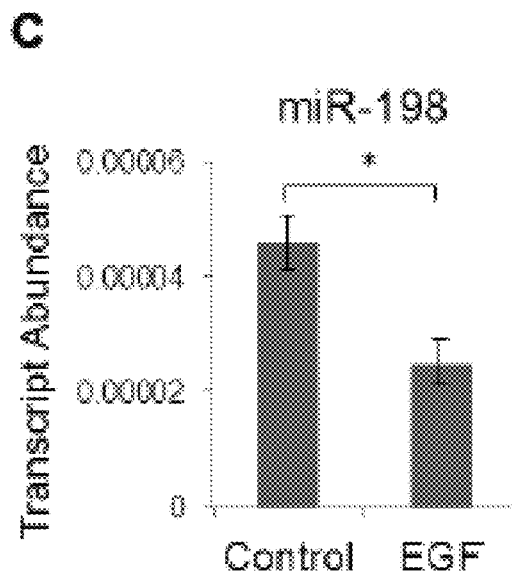
Figure 21:
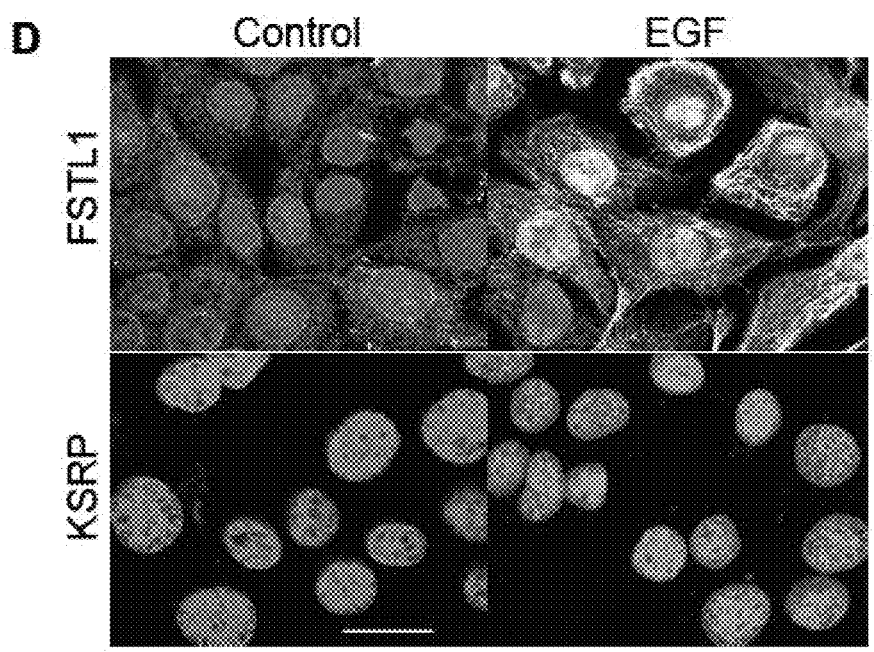
Figure 21:
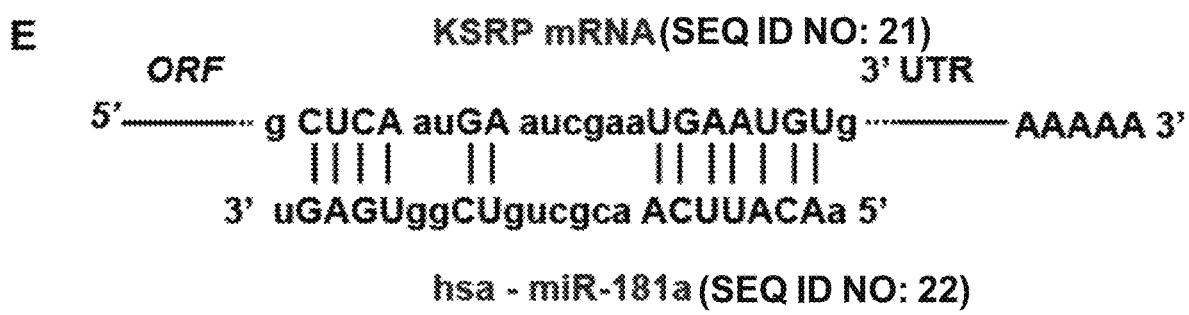
Figure 21:
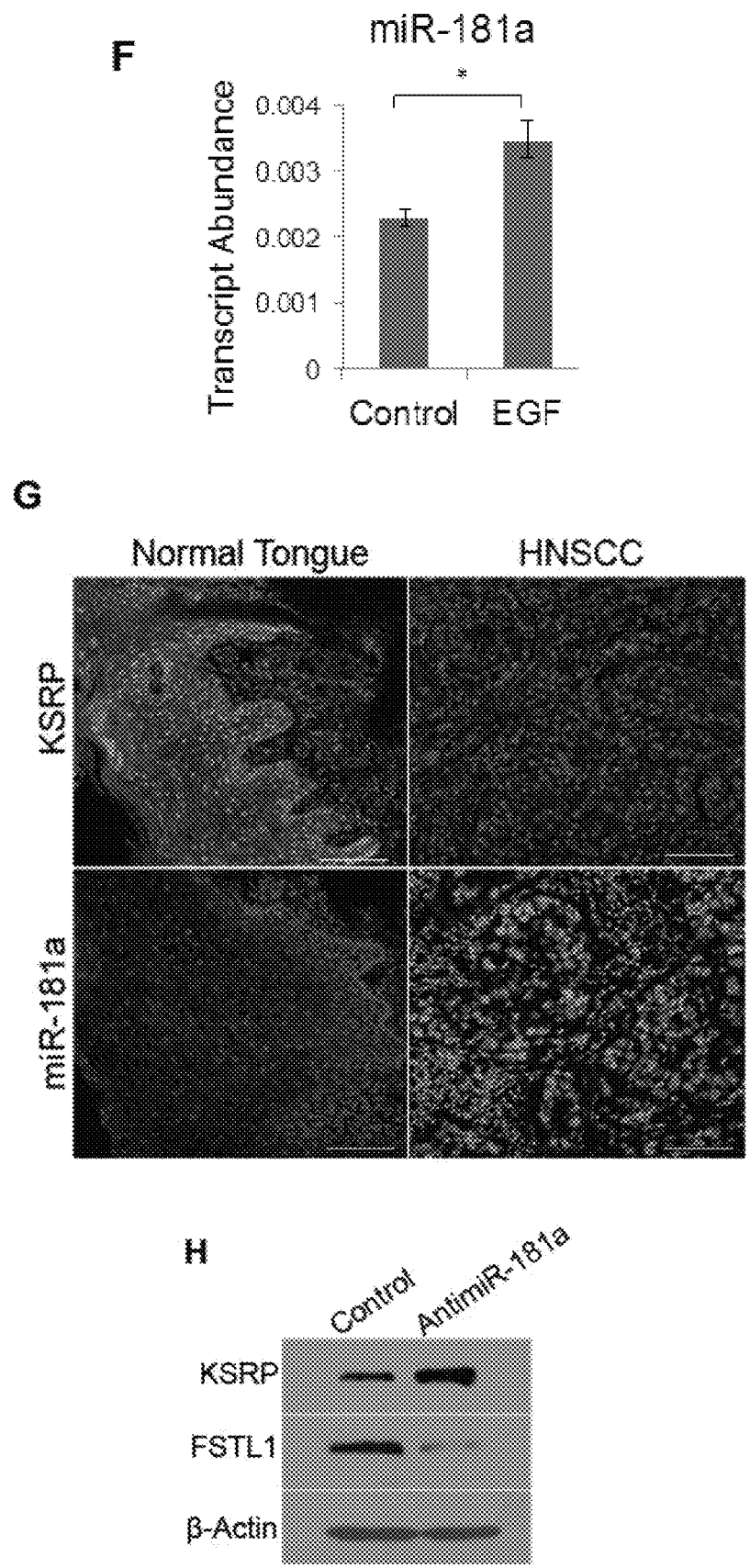
Figure 21:
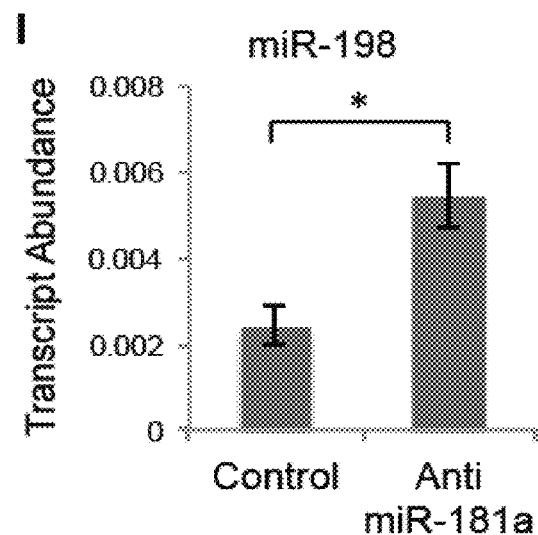
Figure 21:
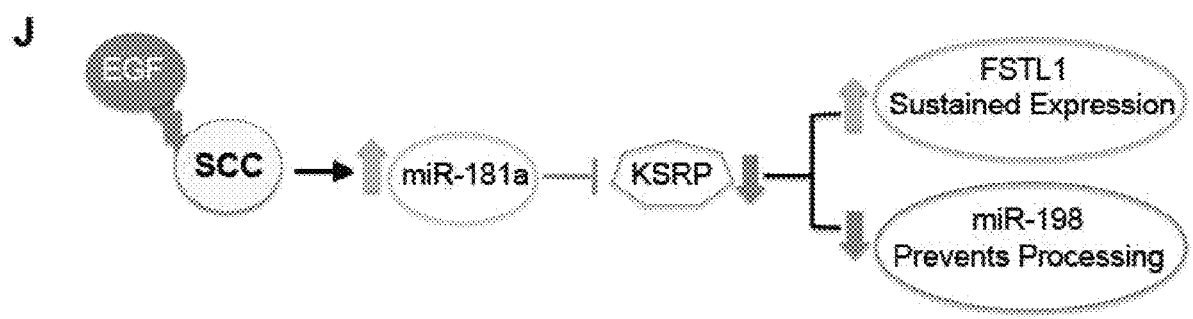

However, immunohistochemistry with anti-FSTL1 antibodies on HNSCC tissue sections revealed sustained expression of FSTL1 protein in HNSCC (FIG. 21B, lower panel). Persistent expression of pro-migratory FSTL1 and perpetual absence of anti-migratory miR-198, suggests a defective switch which may facilitate increased cell migration in HNSCC.

The wound healing switch is regulated by TGF-β, which turns off miR-198 and switches on FSTL1 expression upon injury. However, low levels of TGF-β (FIG. 8, upper panel) suggest a different mode of regulation in HNSCC. Nevertheless, increased expression of epidermal growth factor (EGF) in HNSCC (FIG. 8, lower panel) and down-regulation of miR-198 by EGF in breast cancer, suggested a link between EGF and the molecular switch. Treatment of HNSCC cell lines, including A253, SCC12 or FaDu cells with EGF resulted in the down-regulation of miR-198 (FIG. 21C) with a concomitant increase in the expression of FSTL1 (see FIG. 21D (upper panel)). To address the underlying mechanism by which EGF regulates the molecular switch, the expression of KH-type splicing regulatory protein (KSRP) was examined. MicroRNA-198 belongs to a small cohort of miRNAs that require KSRP for processing. A significant down-regulation of KSRP expression was evident upon treatment with EGF (FIG. 21D (lower panel)). All the above results indicate that the epidermal growth factor (EGF) turns off miR-198 expression by down-regulating KSRP and allows sustained expression of FSTL1.

Next, to investigate, the mechanism by which EGF down-regulates KSRP, the expression of miR-181a was analysed. The KSRP 3'-UTR which has a highly conserved binding site for miR-181a (FIG. 21E) was shown to be a direct target of miR-181a. A significant increase in the expression of miR-181a upon treatment with EGF (FIG. 21F), suggested that miR-181a is a downstream effector of EGF. Moreover, down-regulation of KSRP (FIG. 21G, upper panel) and an inverse correlation in the expression pattern of miR-181a (FIG. 21G, lower panel) in HNSCC tissues, all suggest a link between KSRP and miR-181a. Nevertheless, a significant increase in KSRP protein expression (FIG. 21H, top panel) upon knockdown of miR-181a, (FIG. 21H) confirmed that KSRP is a target of miR-181a. Further, a significant decrease in FSTL1 expression (FIG. 21H, middle panel) with a concomitant increase in miR-198 expression (FIG. 21I) was evident upon knockdown of miR-181a, thus emphasising the role of miR-181a as an upstream regulator of the molecular switch. In summary, an upstream network was deciphered, wherein EGF-mediated up-regulation of miR-181a targets KSRP and in the absence of KSRP, processing of miR-198 fails, resulting in sustained expression of FSTL1 in HNSCC (FIG. 21J).

The Defective Switch is Pro-Invasive

Figure 22:
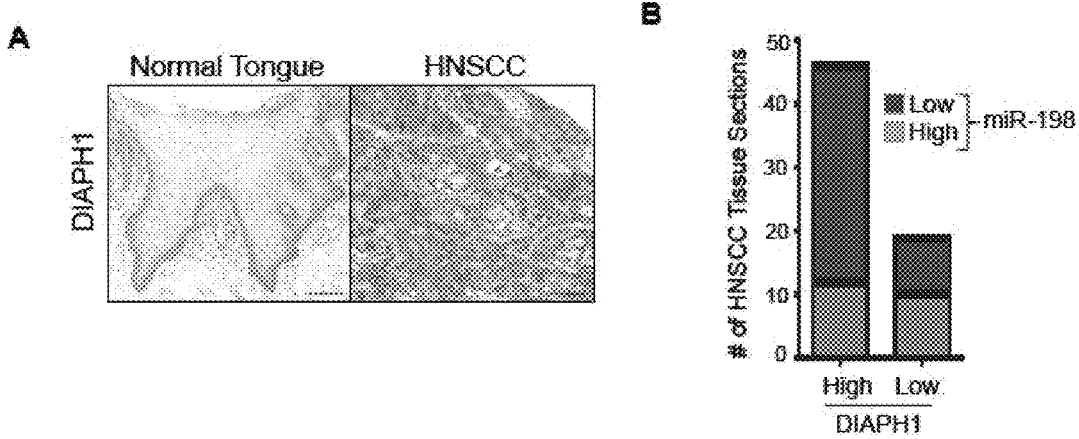
FIG. 22 shows that the defective switch is pro-invasive. A) Immunostaining of DIAPH1 on normal tongue and HNSCC tissue sections. In comparison with normal tongue tissue, a significant increase in DIAPH1 expression is clearly observed in HNSCC (n=64) tissue sections. Scale bar: 100 µM B) Expression pattern of miR-198 and DIAPH1 across HNSCC tissue samples indicates a clear inverse correlation. C, D) Boyden chamber invasion assay shows a significant decrease in the number of cells invading the chamber matrix in siDIAPH1 or siFSTL1 compared to control cells. Representative images of migrated cells detected with Giemsa staining. Cells were counted from six independent fields and histogram below represents relative number of invaded cells. **P<0.001 Error bars represent s.d. E) Morphology of SCC cells transduced with control shRNA or shRNA against FSTL1 or DIAPH1 (top panel) visualized using phalloidin conjugated-TRITC. Knockdown of FSTL1 or DIAPH1 showed a significant difference in morphology compared to control cells (upper panel). A snap shot of cell trajectory displacement over a period of 24 hours in control, shFSTL1 and shDIAPH1 cells, depicted (bottom panel). F) Analysis of cell displacement in control, shFSTL1 and shDIAPH1 cells. One-way analyses of variants (ANOVA) with Dunnett's multiple correction tests were used to calculate the statistical significance between groups. *P<0.05 **P<0.01 G) Organotypic invasion assay with SCC12 cells expressing control shRNA or shRNA against FSTL1 or DIAPH1. SCC12 cells were detected by KRT14 staining (in red).
Figure 22:
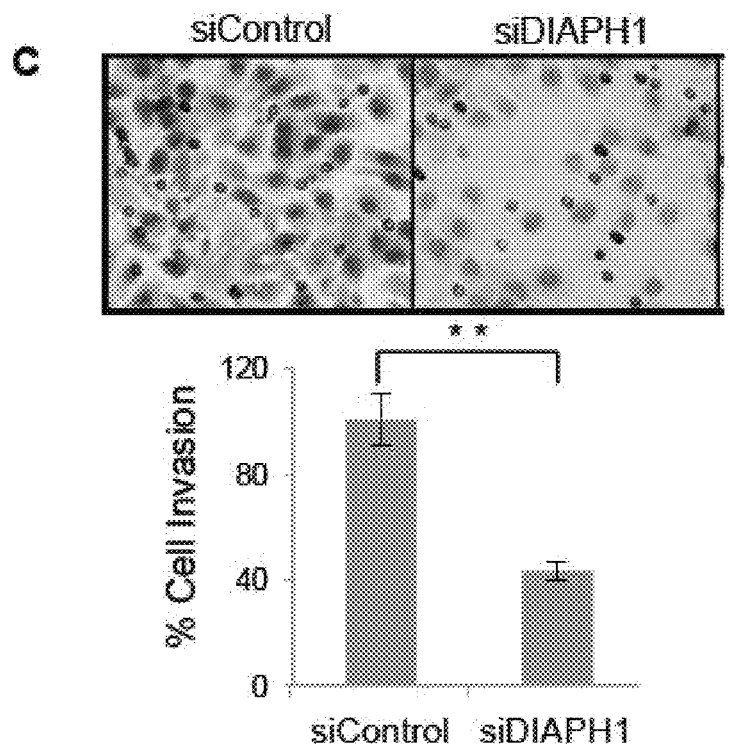
Figure 22:
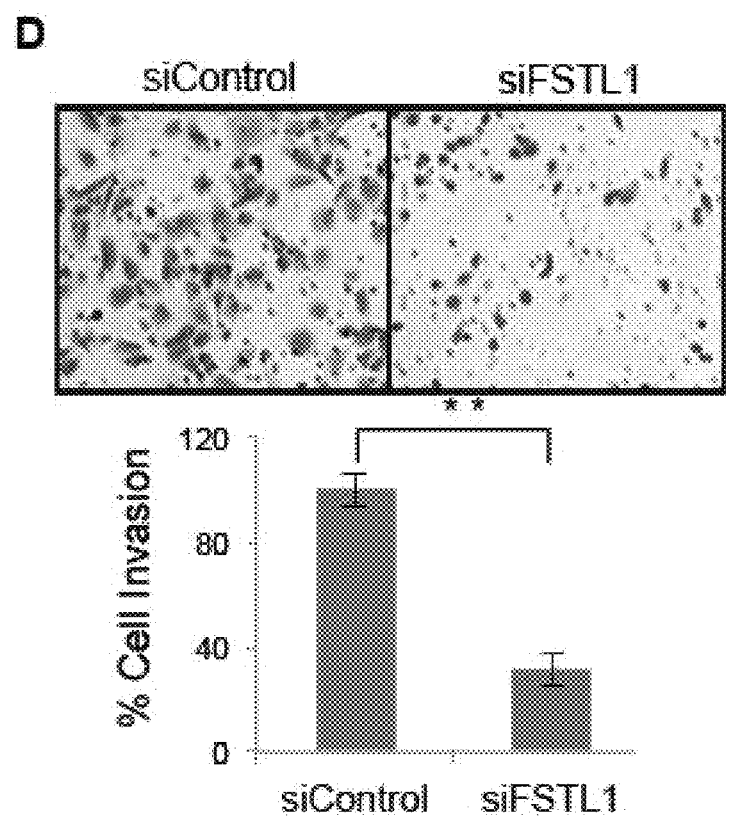
Figure 22:
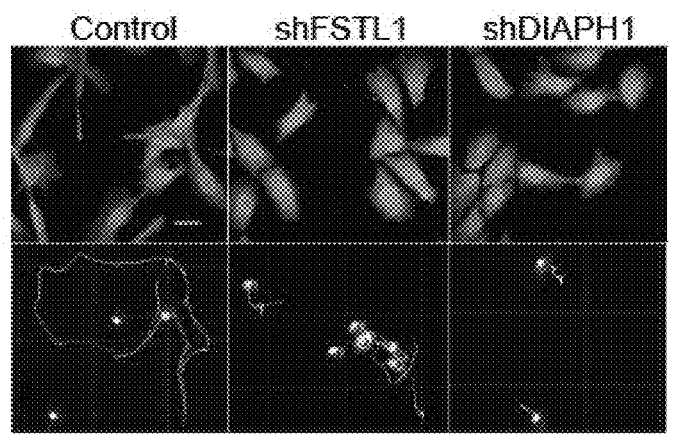
Figure 22:
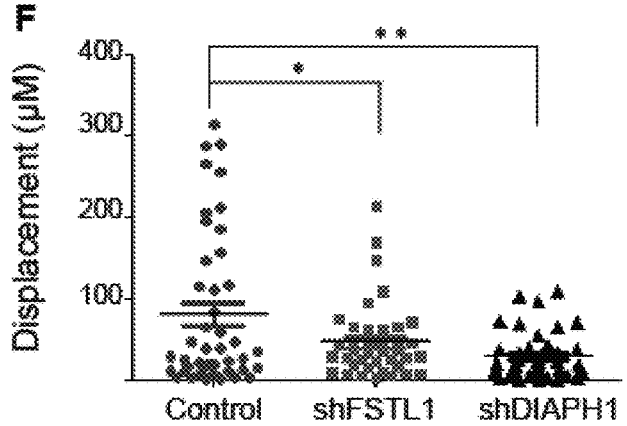
Figure 22:
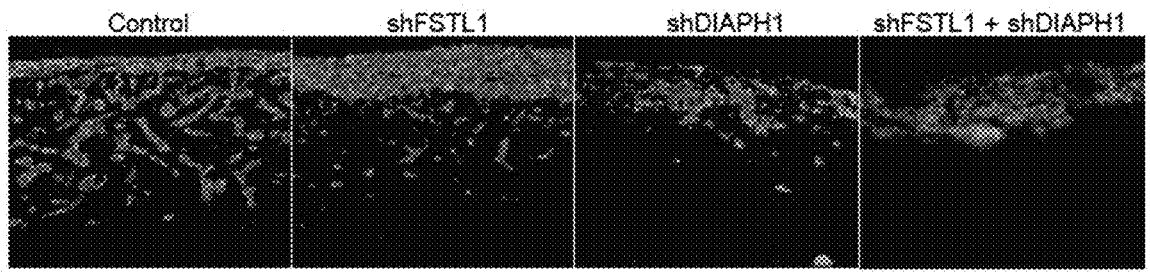

In the absence of anti-migratory miR-198 the expression of pro-migratory targets in HNSCC was examined. Upon normal epidermal wounding, the miR-198 silencing switch de-represses several diverse mechanistic pathways that promote cell migration and tissue remodelling for wound healing. These pro-migratory miR-198 target genes include urokinase-type plasminogen activator (PLAU), a serine protease involved in degradation of extracellular matrix, diaphanous homolog 1 (DIAPH1) involved in actin polymerization, and laminin gamma 2 chain (LAMC2), forming part of the essential basement membrane protein laminin 332. However, based on expression pattern in HNSCC, the focus here is on DIAPH1 and its role in HNSCC. Immunohistochemistry on HNSCC tissue sections using anti-DIAPH1 antibody clearly indicates an aberrant expression of DIAPH1 in HNSCC (FIG. 22A). DIAPH1 is a direct target of miR-198 and, as expected in the presence of high levels miR-198 in normal tongue tissue, little or no DIAPH1 was seen (FIG. 22A). Furthermore, an inverse correlation in the expression of miR-198 and DIAPH1 was apparent (FIG. 22B) with ~80% percent of the patients showing increased expression of DIAPH1 with a concomitant decrease in miR-198 in HNSCC tissue sections. The defective switch promotes sustained expression of pro-migratory DIAPH1 and FSTL1. To investigate the specific role of the two genes in HNSCC, cells were subjected to Boyden chamber trans-well assay. Following trans-well migration, cells attached to the lower surface of the filters were counted. Transient knockdown of DIAPH1 or FSTL1 (FIGS. 5A and 6A) leads to a significant decrease in cell migration with a ratio of 37.45±3.65% and 34.23±2.88% respectively compared to the control SCC12 cells (FIGS. 22C and 22D). Further, constitutive knockdown of FSTL1 or DIAPH1 using specific shRNA against FSTL1 or DIAPH1 (FIGS. 5B and 6B), results in a transition from mesenchymal to epithelial phenotype (FIG. 22E, upper panel). Live cell imaging to track the cellular trajectory over a 24 hour time period revealed a significant decrease in cell migration with the loss of FSTL1 or DIAPH1 (FIG. 22E, lower panel and 22F). Finally, shFSTL1 or shDIAPH1 cells or combined knockdown cells were subjected to a 3-dimensional organotypic assay that mimics in vivo stromal invasion. Knockdown of FSTL1 or DIAPH1 results in a considerable decrease in the number of cells invading the matrigel compared to control SCC cells, however a combined knockdown of both the genes almost completely inhibits the cells from invading the matrigel (FIG. 22G). Together all these results indicate that sustained expression of FSTL1 and DIAPH1 potentially enhance migration/invasion of carcinoma cells and the defective switch is pro-invasive.

Prognostic Significance of FSTL1-DIAPH1 Gene-Pair

Figure 23:
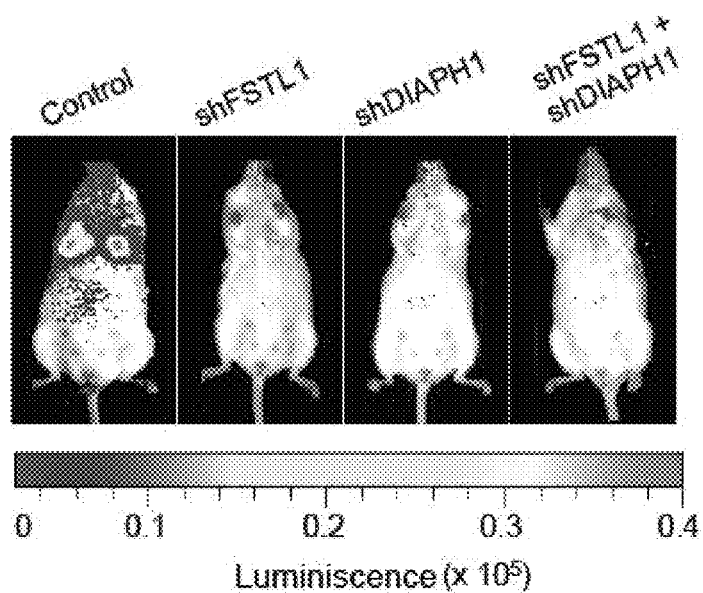
FIG. 23 shows data depicting the prognostic significance of FSTL1-DIAPH1 gene-pair. A) shows the results of bioluminescence imaging of systemic metastasis by A253 cells expressing luciferase reporter and control shRNA or shRNA against FSTL1 or DIAPH1 individually, or in combination (n=7). B) shows a representation of the total number of metastatic foci in lung sections **P<0.001. C) shows images showing lungs that were extracted on day 26 and stained for KRT5 expression, and shows representative images of lung metastatic colonies. D) shows a scatter plot of FSTL1 and DIAPH1 expression determined in 262 patients, classified into four distinct segments a, b, c and d, based on 2D-DDg method. E) Kaplan-Meier survival curves of individual segments. F) Kaplan-Meier survival curves with statistical significance by log-rank test of two groups, where patients were grouped as low-risk (segments a, b and c) and high-risk (segment d).
Figure 23:
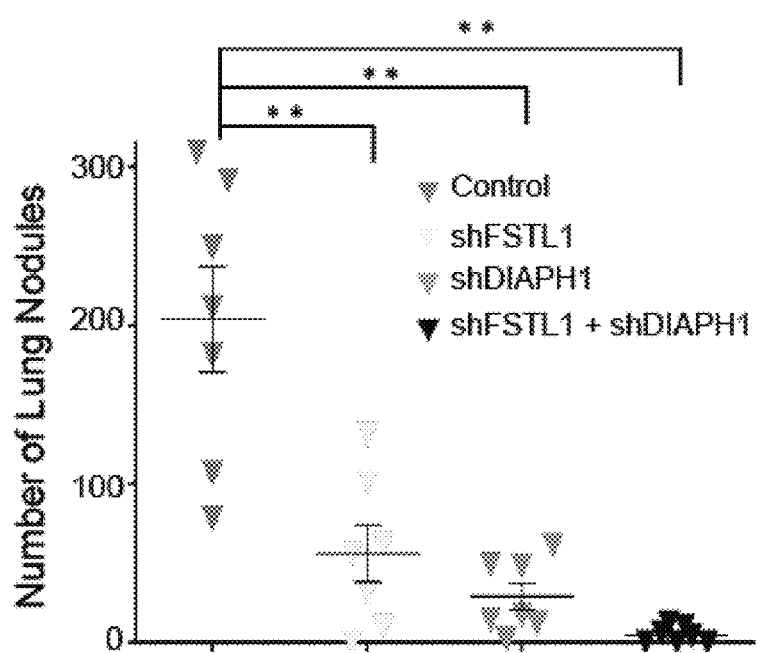
Figure 23:
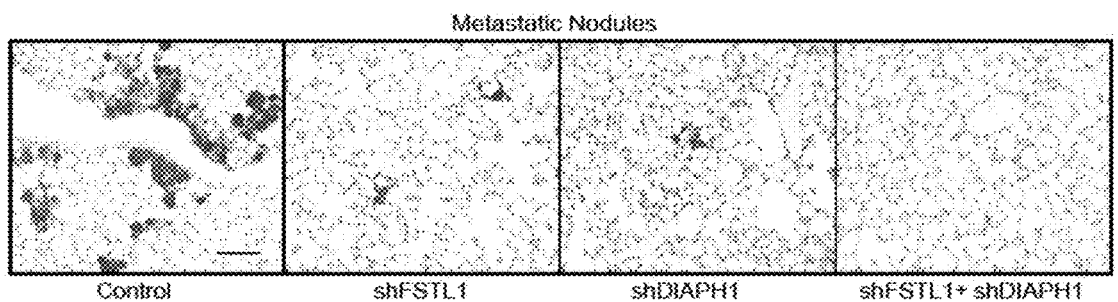
Figure 23:
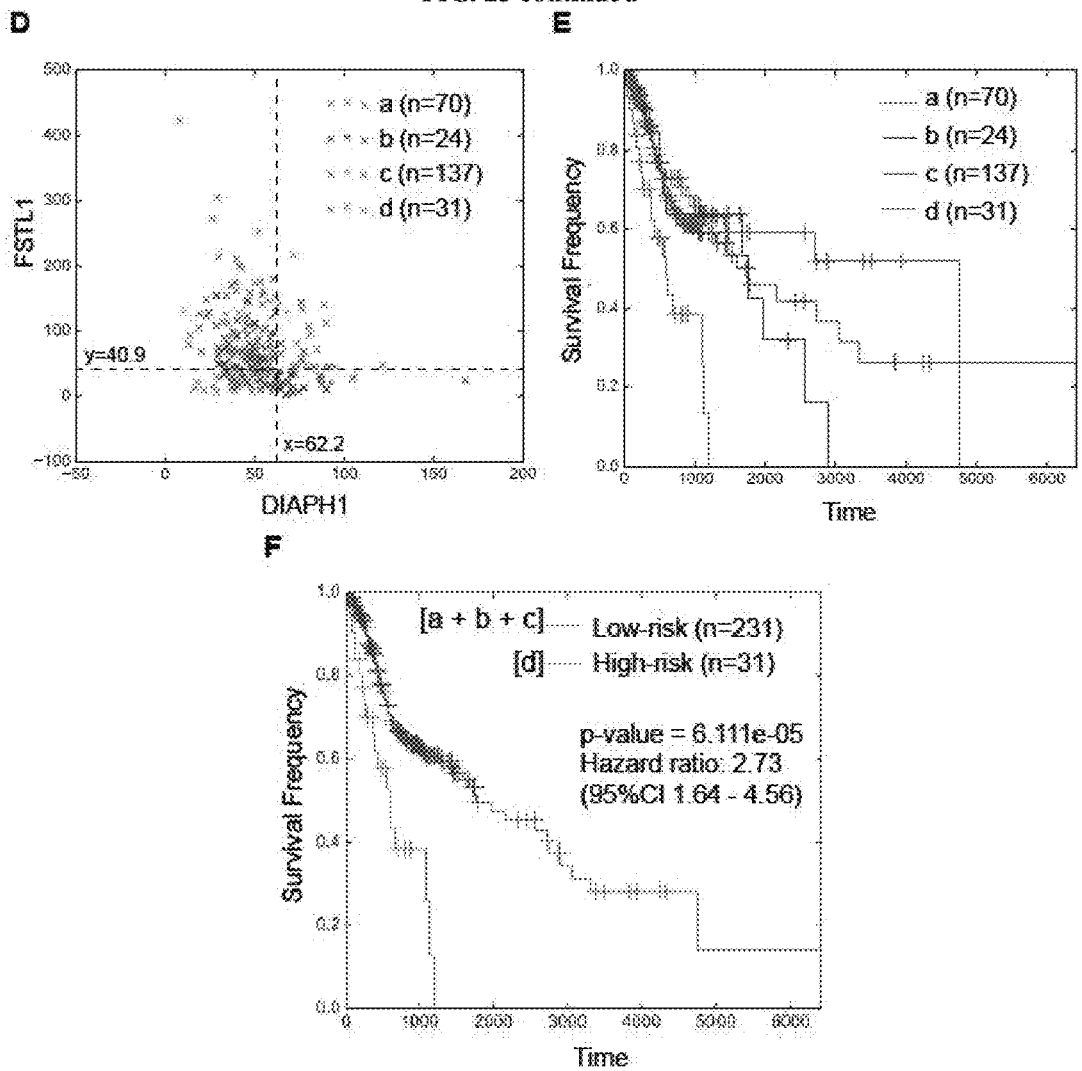

To determine the role of FSTL1 and DIAPH1 in metastasis, genetically modified luciferase expressing A253 and FaDu cell lines were transduced with lentivirus encoding shFSTL1 or shDIAPH1 individually or in combination. Cells were implanted in immunodeficient NSG mice by lateral tail vein injections and evaluated for metastatic colonization. Silencing of FSTL1 or DIAPH1 independently decreased lung colonization significantly compared to the control cells (FIG. 23A). Histological quantification revealed a substantial decrease in the total number of metastatic colonies upon knockdown of FSTL1 or DIAPH1 (FIG. 23B). Concurrent knockdown of FSTL1 and DIAPH1 results in a significant decrease in the number of lung colonies with no visible colonies in majority of the mice (FIGS. 23A, 23B, and 23C, p<0.001). Results were consistent in both A253 and FaDu cell lines (data not shown). In summary, the above results highlight the importance of the gene-pair, FSTL1-DIAPH1 in metastatic colonization of HNSCC.

To understand the clinical significance of the defective switch, the expression profile and clinical data of 262 patients diagnosed with head and neck cancer from The Cancer Genome Atlas (TCGA) research network (TCGA, 2015) were interrogated. The level 3 RPKM intensity values of the RNA expression were downloaded from the database and analysed. Independently, the survival significance of the genes FSTL1 and DIAPH1 were assessed via 1D-DDg. Results revealed that independently, both FSTL1 (borderline significant, logrank p=0.0583) and DIAPH1 (logrank p=0.00160) exhibited oncogenic behaviour, whereas higher expression corresponded to poor overall survival of patients.

Next, to study the potential combinatorial effect of the two genes FSTL1 and DIAPH1, a 2-dimensional data-driven grouping (2D-DDg) method was used to identify expression cut-offs on a two-dimensional axis to stratify the patient cohort into significant survival subgroups. Based on the expression cut-offs obtained via the 2D-DDg method, the Kaplan-Meier survival plots showed that patients with low expression of both FSTL1 and DIAPH1 exhibited relatively good overall survival (FIG. 23D—quadrant a and 23E). In contrast, in patient subgroups where either only FSTL1 (FIG. 23D—quadrant c and 23E) or DIAPH1 (FIGS. 23D—quadrant b and 23E) has higher expression, there was an observable trend towards poor survival.

Finally, in patients with high expressions of both FSTL1 and DIAPH1 (FIGS. 23D—quadrant d and 23E), the overall survival rates were significantly poor, compared to the other patient subgroups. Results indicated that FSTL1 and DIAPH1 both exhibited oncogenic behaviour, however, when combined, the prognostic features of the gene-pair generates a robust patient stratification with a logrank p-value=6.111e-05 (FIG. 23F). This suggested a potential combinatorial effect between these two genes in the development, progression and prognosis of HNSCC.

EGF-Driven Microcircuitry Steers a Two-Pronged Pathway Towards Metastasis

Figure 24:
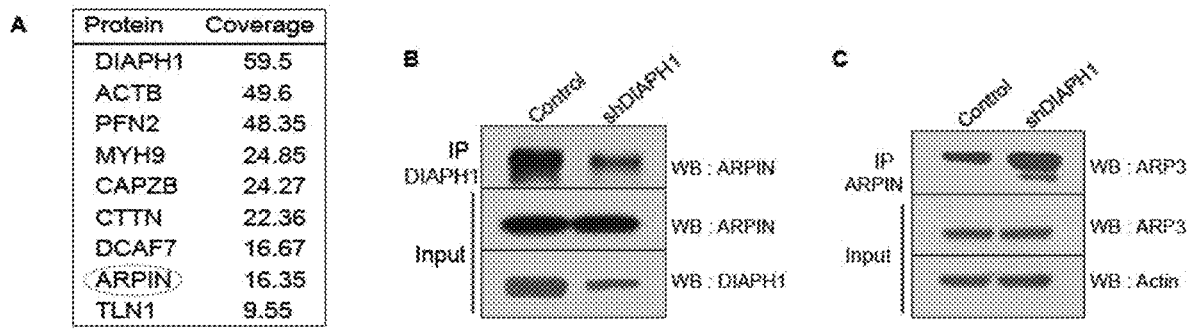
FIG. 24 shows that EGF-driven micro-circuitry steers a two-pronged pathway towards metastasis. A) provides a list of selected interacting partners of DIAPH1 shortlisted from the BioID database. B) shows the results of a pull-down analysis. Following immunoprecipitation (IP) with anti-DIAPH1 antibody, cell lysates from SCC12 control or shDIAPH1 cells were probed for the presence of Arpin by western blot analysis (top panel). Input cell lysates were probed for Arpin (middle panel) and DIAPH1 (lower panel). C) shows the results of a further pull-down analysis. Following immunoprecipitation (IP) with anti-Arpin antibody cell lysates from SCC12 control or shDIAPH1 cells were probed for Arp3 by western blot analysis (top panel). Input cell lysates were probed for Arp3 (middle panel) and β-actin (lower panel). D) shows the gene expression values of selected genes from microarray data of SCC12 cells transfected with control non-targeting shRNA or shRNA against FSTL1, represented as a heat-map. Expression values displayed in shades of red (high) or blue (low) relative to the individual mean value of the gene in linear scale. E) shows the results of a gelatin zymography, to assess the proteolytic activity of proteins separated by polymerase gene electrophorese. Quantification of band intensities represented as a histogram (top panel). P<0.001. Error bars represent standard deviations (s.d.). F) shows the results of Western blot analysis on A253 cell lysates from control or EGF pre-treated cells. Lysates were probed for phosphoERK or total ERK. G) shows histograms representing the relative transcript abundance of MMP9 in control or shFSTL1 in A253 cells treated with EGF [P<0.001]. H) shows the result of A253 cell lysates which were subjected to immunoprecipitation with IgG or anti-FSTL1 antibody. The immunoprecipitates, along with input lysate, were probed for Wnt7a by western blot analysis. I) shows the results of shFSTL1 cells which were transfected with specific siRNA against Wnt7a. Cells were treated with EGF post-transfection and cell lysates were probed for phosphoERK or total ERK by western blot analysis. J) shows a schematic illustrating a model mechanism of, without being bound by theory, the hijacking of miR-198/FSTL1 molecular switch by EGF, leading to a two-pronged pathway towards metastasis.
Figure 24:
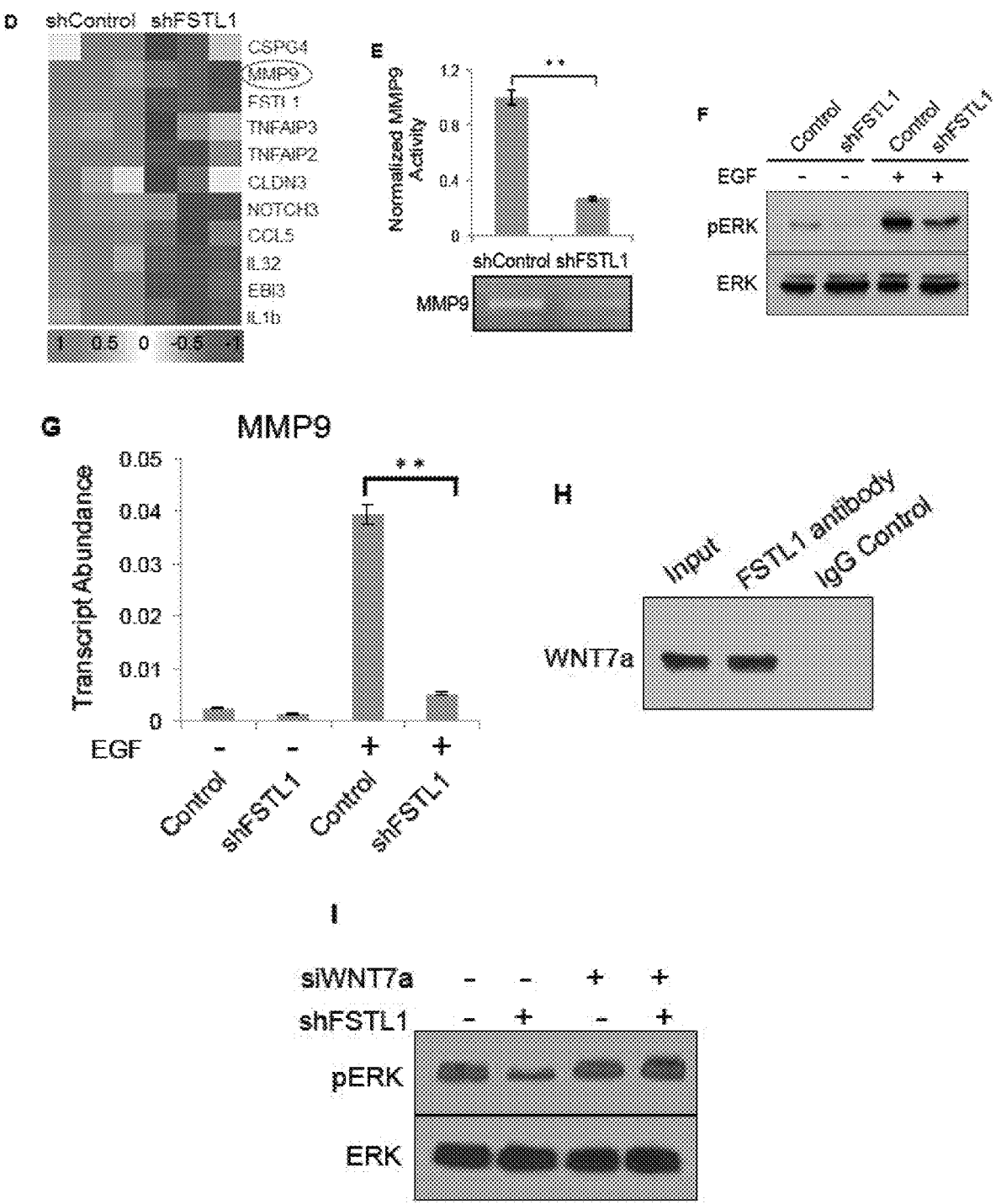
Figure 24:
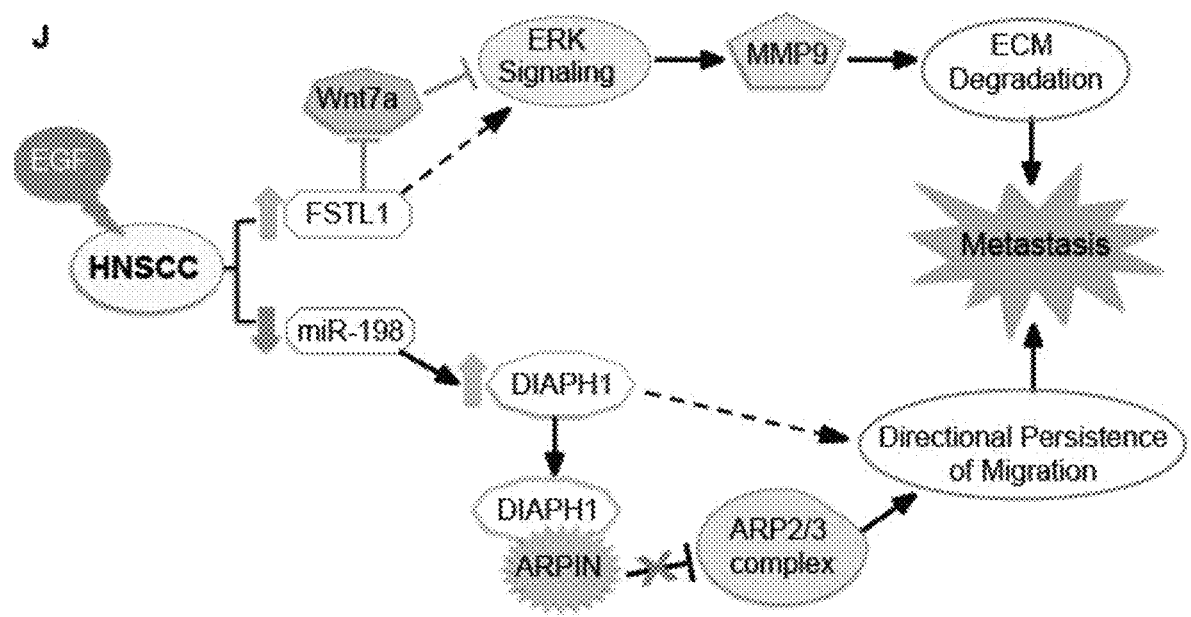

To investigate the underlying molecular mechanism, by which DIAPH1 promotes metastasis, a BioID (Proximity-dependent biotin identification) analysis was performed to identify potential interacting partners of DIAPH1. Arpin, which is a negative regulator of cell migration, was identified as a candidate interaction partner of DIAPH1 (FIG. 24A). Arpin, a competitive inhibitor of the Arp2/3 complex is known to contribute to the collapse of lamellipodia and restrict cell migration. On the other hand, DIAPH1 which is an EGF-regulated actin nucleator, together with Arp2/3 complex, is known to nucleate polymerization of branched actin filaments to form lamellipodia, thin sheet-like membrane protrusions which drives cell migration. Without being bound by theory, it was hypothesized that DIAPH1 may sequester Arpin, and prevent its association with Arp2/3 complex, thus enhancing cell migration.

To confirm the interaction of DIAPH1 with Arpin, cellular lysates from control or shDIAPH1 A253, SCC12 or SCC13 cells were subjected to immunoprecipitation (IP) using anti-DIAPH1 antibody and the immunoprecipitates were probed for Arpin by Western blot analysis. Significant enrichment of Arpin in control samples, compared to DIAPH1 depleted samples, confirmed the specific interaction of Arpin with DIAPH1 (FIG. 24B). Further, cellular lysates from control or shDIAPH1 cells were subjected to immunoprecipitation with anti-Arpin antibody, and the immunoprecipitates were probed for Arp3 by Western blot analysis. Significant enrichment of Arp3 in DIAPH1 depleted samples compared to control samples, highlight the role of DIAPH1 in sequestering Arpin, thus preventing the interaction of Arpin with Arp3 (FIG. 24C). These results were consistent across multiple cell lines. In conclusion, the data highlights sequestration of the negative regulator Arpin, by DIAPH1. Arpin is known to reduce the cell speed and directional persistence of migration simultaneously. The data shown herein indicates that DIAPH1 sequesters and blocks the interaction of Arpin with Arp2/3 complex, leading to increased cell motility, directional persistence of migration and metastasis of carcinoma.

To investigate the mechanistic pathway by which FSTL1 contributes to metastasis of HNSCC, a microarray analysis was performed comparing gene expression from control versus shFSTL1 SCC12 cells. A significant downregulation of MMP9 upon knockdown of FSTL1 was apparent (FIG. 24D) and was further verified by qRT-PCR analysis (FIG. 24G). Moreover, detection of MMP9 in control cells and a decrease in the activity of MMP9 upon knockdown of FSTL1, (FIG. 24E) all suggests that FSTL1 is an upstream regulator of MMP9 expression. However, it is known that activation of extracellular signal-regulated kinases (ERK) by EGF, stimulates expression of MMP9. As EGF regulates MMP9 expression by activating the ERK pathway, the cell lysates from EGF-treated, control or shFSTL1 A253 cells were probed for the expression of ERK or phosphoERK. Loss of FSTL1 results in a significant reduction in EGF-mediated phosphorylation of ERK (FIG. 24F) suggesting that FSTL1 is essential for EGF-mediated ERK phosphorylation. Further, qRT-PCR analysis clearly indicates that, EGF-mediated up-regulation of MMP9 fails in the absence of FSTL1, confirming that FSTL1 is essential for EGF-mediated MMP9 expression (FIG. 24G). These results were consistent across multiple cell lines tested. In summary, all the above results indicate the vital role of FSTL1 as an upstream regulator of EGF-mediated MMP9 expression. EGF hijacks the molecular switch and allows sustained expression of FSTL1, resulting in activation of ERK; which now stimulates MMP9 expression, leading to ECM degradation and metastasis of HNSCC.

To understand how a secreted glycoprotein, FSTL1, regulates ERK phosphorylation, the protein interactors of FSTL1 were elucidated. The Biological General Repository for Interaction Datasets (BioGRID) analysis revealed multiple interacting partners of FSTL1, including Wnt4, Wnt5a, Wnt7a and Wnt10b (FIG. 19). Cell lysates from A253 cells were subjected to immunoprecipitation with anti-FSTL1 antibody or IgG control and the immunoprecipitates were probed for Wnt4, Wnt5a, Wnt7a and Wnt10b by Western blot analysis. However, detection of only Wnt7a, indicates specific interaction with FSTL1 with Wnt7a in HNSCC (FIG. 24H). On the other hand, Wnt7a is known to inhibit EGF signalling, and suppress tumour cell invasion. Taken together, this leads to the hypothesis, that FSTL1 interacts, sequesters and blocks Wnt7a, thus allowing EGF-mediated ERK phosphorylation, which leads to MMP9 expression. To test this hypothesis shFSTL1 A253 cells, were transfected with specific siRNA against Wnt7a and post-transfection, cells were treated with EGF to stimulate ERK phosphorylation.

Depletion of FSTL1 inhibits ERK phosphorylation, however, knockdown of Wnt7a results in restoration of ERK phosphorylation (FIG. 24I) suggesting the role of Wnt7a as an inhibitor of EGF-mediated ERK phosphorylation in HNSCC. However, simultaneous knockdown of FSTL1 and Wnt7a, does not affect the phosphorylation of ERK (FIG. 24I). In conclusion, all the above results suggest that the secreted glycoprotein FSTL1 interacts with Wnt7a and antagonises Wnt7a-mediated repression of ERK phosphorylation in HNSCC. This allows phosphorylation of ERK, which stimulates expression of MMP9, leading to extracellular matrix degradation and promotes metastasis of carcinoma cells (FIG. 24J).

Wound healing is a self-limiting dynamic event where barrier disruption is transient. Following wound repair activated keratinocytes revert to a quiescent state and re-differentiate to restore a functional epidermal barrier, whereas carcinoma cells persist in an activated state maintaining a gene expression profile typical for migration and metastasis.

Specific role of many miRNAs in cancer as tumour-suppressors or oncogenes is well known. The anti-migratory miR-198 targets regulators of mitogenic and motogenic pathways and inhibits migration. However, as a consequence of the defective switch, in HNSCC, miR-198 expression is blocked, leading to sustained expression of pro-migratory target genes including DIAPH1. The role of DIAPH1 in stabilisation of interphase microtubules is well known and a decrease in metastatic potential of cancer cells was observed upon depletion of DIAPH1 in colon cancer cells. DIAPH1, which is an EGF-regulated actin nucleator, together with Arp2/3 complex, nucleates polymerisation of branched actin filaments to form thin sheet-like membrane protrusions, known as lamellipodia and drives polarised cell migration. However, Arpin, which is a competitive inhibitor and a negative regulator of Arp2/3 complex, contributes to the collapse of lamellipodia, applying stringent brakes and restricts cell migration. In HNSCC, an additional role of the multifunctional DIAPH1, which sequesters Arpin, and favours directional persistence of migration, to enhance metastasis of carcinoma, was revealed (FIG. 24J).

EGF-mediated activation of ERK cascade regulates cell migration and acquisition of an invasive phenotype. Further, inhibition of MMP9 activity using a neutralising antibody impaired EGF-induced HNSCC invasion, confirming the role of MMP9 in SCC invasion. The data disclosed herein also substantiates the role of EGF in regulating the expression of MMP9, a known prognostic biomarker for HNSCC. However, it is shown that in the absence of FSTL1, EGF-driven signalling cascade fails to up-regulate MMP9, indicating FSTL1 is an upstream regulator of MMP9. Wnt7a is known to inhibit EGF signalling, suppress tumour cell proliferation and invasion. In HNSCC, the secreted glycoprotein, FSTL1 interacts with Wnt7a and antagonises Wnt7a-mediated repression of ERK phosphorylation, leading to MMP9 expression (FIG. 24J).

The subtle but crucial boundaries between the function of FSTL1 in wound healing and its role in the pathology of HNSCC, indicate that FSTL1 expression must be tightly regulated, allowing the protein to perform its physiological function while avoiding the detrimental consequences of sustained inappropriate expression. This emphasises the importance of the regulatory switch, which controls temporal and mutually exclusive expression of miR-198 and FSTL1. Cancer cells hijack the regulatory switch, turn-off miR-198 expression, thus allowing persistent expression of pro-migratory FSTL1 and DIAPH1 (FIG. 24J). The results add another line of evidence to this complex system, highlighting that normal wound healing events are not sufficient to trigger tumour formation. However, aberrant maintenance of the wound microenvironment promotes increased cell migration, invasion and metastasis, leading to carcinogenesis. Modulation of the defective switch is shown here to lead to the development of a therapeutic strategy to treat HNSCC with improved patient outcome.

Materials and Methods

Cell Culture and SCC Tissue Array

HNSCC cell lines (A253, SCC12, SCC13 and FaDu) were cultured in RM+ media (3:1 DMEM; F12 HAMS media supplemented with 10% FBS, 0.5 µg/ml hydrocortisone, 5 µg/ml of insulin and transferrin, 13 ng/ml liothyronin, 1% glutamine, 10 ng/ml epidermal growth factor and penicillin/streptomycin). Tissue array (SK802a) containing cutaneous squamous cell carcinoma sections (76 cutaneous SCC tissue sections, 2 normal sections adjacent to tumour and 2 normal skin sections) was obtained from US Biomax. Human foreskin dermal fibroblasts and lenti-X 293T (Clonetech) were cultured in DMEM supplemented with 10% FCS and penicillin/streptomycin. HNSCC tissue arrays (HN803b) were obtained from US Biomax. Five HNSCC sections were negative for KRT14/KRT5 and therefore omitted for further study. Human foreskin dermal fibroblasts and lenti-X 293T (Clontech) were cultured in DMEM supplemented with 10% FCS and penicillin/streptomycin Antibodies Antibodies used in this study are as follows. Goat anti-FSTL1 antibody (#ab11805, Abcam), Rabbit anti-FSTL1 antibody (Protein tech), Rabbit anti-DIAPH1 antibody (#5486, Cell Signaling), Rabbit anti-KSRP antibody (#A302-22A, Bethyl laboratories), ms anti-KRT14 (clone LL001), mouse anti-EGF (R&D systems, clone 10825), mouse anti-TGFβ1 (Novacastra) Rabbit anti-GFP (Covance), Rabbit anti-cMyc (Sigma). Streptavidin Alexa 555, Chicken anti-goat Alexa 488 and Donkey anti-rabbit/mouse Alexa 488/555 were from Molecular probes. Rabbit anti-Arp3 (#4738), phospho (#9101) and total ERK antibodies (#9102) were from Cell Signaling. Rabbit anti-Arpin (#ABT251) was purchased from Merck Millipore. Other antibodies used herein are Mouse anti-LAMC2 antibody (#sc25341, Santacruz biotechnologies), Rabbit anti-PLAU (#ab24121, Abcam), Mouse anti-TGF-β1 (clone 9016, R&D systems), Rabbit anti-HuR antibody (#ab85539), Rabbit anti-CSPG4 (#ab104535), mouse anti-cMET (clone 11.1, Wong et al., 2013), mouse anti-MMP9 (#sc13520, Santa Cruz biotechnologies).

Stable Knock-Down and Microarray Analysis

ShRNAs were designed against the open reading frame of FSTL1/DIAPH1 sequences using siRNA wizard software (Invitrogen). ShRNAs were cloned into a lentiviral shRNA expression vector (pKAMU), in which H1 promoter drives the expression of shRNA by RNA polymerase III. Third generation lentiviruses were produced in Lenti-X 293T cells (Clontech) by co-transfection of shControl/shFSTL1/shDIAPH1 vectors and lentiviral packaging plasmid mix (pMDLg/pRRE, pRSV-Rev and pMD2.G). HNSCC cell lines were transduced with either control lentivirus encoding a scrambled shRNA or shRNA against FSTL1/DIAPH1. Cells with stable integration of lentiviruses were selected with 2 μg of puromycin for 2 weeks. Total RNA was isolated from cells using the Exiqon miRcury RNA isolation kit. 250 ng of total RNA was converted into biotinylated cRNA using a TargetAmp Nano-g Biotin-aRNA labeling kit (Epicenter). 750 ng of biotinylated cRNA was hybridized to HT-12 V4 expression bead chip (Illumina) using samples in triplicate. Hybridization, washing and scanning were performed according to the manufacturer's protocol. Data extracted was normalized and analyzed using Illumina BeadStudio.

Boyden Chamber Invasion Assays

Transient knock-down of FSTL1, DIAPH1, PLAU and LAMC2 were achieved by transfection of 50 nM of On-target plus smart-pool siRNA (Dharmacon/Thermofischer scientific) using Dharmafect 1 transfection reagent as per manufacturer's protocol. A non-targeting siRNA was transfected as negative control. In vitro invasion assays were performed in BD biocoat matrigel invasion assay chambers. Two days post transfection cells were harvested and seeded onto the upper chamber in RM+ media without serum. Complete RM+ medium was used as a chemo-attractant in the lower chambers. 20 hours post seeding, cells above the membrane was wiped out with a cotton swab and the invaded cells were fixed in methanol and stained with Giemsa solution. Cell invasion was expressed as the percentage of cells invaded in six microscopic fields per chamber in three biological replicates. Invaded cell numbers in non-targeting siRNA transfected was considered as 100%.

Organotypic Invasion Assay and Quantification

Organotypic assays were set up as described in the art, with minor modifications. Briefly, in ice cold conditions, equal amount of matrigel (#354234 BD Biosciences) and rat tail collagen type I (#354236 BD Biosciences) with one tenth volume of FCS and 10×DMEM were mixed and pH adjusted to neutral by addition of 0.1N NaOH. About 800 μl of this solution was added to millicell hanging cell culture inserts and placed in 12-well plates (Nunc) for 1 hour at 37° C. for solidification. Complete fibroblast medium was added to both top and bottom of the insert and left overnight at 37° C. Human dermal fibroblasts ($1 \times 10^5$) was mixed with SCC cell line ($2.5 \times 10^5$) and seeded onto the gel and allowed to grow submerged in RM+ medium for 24 hours. Inserts were lifted to air liquid interface the very next day and cultures were maintained in RM− media (RM+ media without epidermal growth factor) for two weeks after which the organotypic gels were processed for histology. The depth of invasion of Keratin 14 positive cells were quantified as described in the art.

Immunohistochemistry

Five micron tissue sections were mounted on polylysine-coated glass slides (Thermo Scientific). Sections were deparaffinised in xylene and rehydrated using descending ethanol concentrations and finally in phosphate buffered saline (PBS). Endogenous peroxidase was quenched by immersing the slides in 3% hydrogen peroxide and methanol for 30 minutes. Antigen retrieval (dependant on the antibody), was performed using programmable pressure cooker with "target retrieval solution", pH 6.0 (Dako). Non-specific reactivity in the tissues was blocked by incubation in 10% goat serum in PBS before incubating with the primary antibody at room temperature. Primary antibodies were removed before incubation with species matched secondary HRP-labelled polymer antibodies (Dako). Chromogen 3,3'-diaminobenzidine (Dako) was used as substrate for colour development. Slides were counterstained with hematoxylin before dehydration and mounted with DPX (Sigma). For fluorescent immunodetection, species specific secondary antibodies conjugated to Alexa 488/555 were used instead of HRP-labelled polymer antibodies. Sections were washed with running tap water, counterstained with DAPI (100 ng/ml) and mounted using Florsave (Calbiochem) mounting medium. For experiments where goat primary antibodies were used, 5% BSA in PBS was substituted for 10% goat serum. Images were acquired on a Zeiss Axioimager microscope (for bright field imaging) or on Olympus FluoView FV1000 (for fluorescent antibody detection). Quantification of staining intensities in tissue arrays was performed visually by two independent observers. Intensities were classified as negative, week, moderate and strong by averaging the independent observations.

miRNA In Situ Hybridization

5 μm sections were processed and boiled in pre-treatment solution (Panomics), washed in PBS, followed by protease (Panomics) treatment at 37° C. Sections were incubated with LNA probes [5'-DIG labelled LNA probes specific for miR-198/miR-181a or scrambled probe with no homology to known vertebrate miRNAs (Exiqon)] in hybridization buffer (Roche) at 51° C. for 4 hours. Following stringent wash, sections were blocked with 10% Goat serum and further incubated with anti-DIG alkaline phosphatase (Roche) overnight at 4° C. Sections were washed in PBS-T (0.1%) and miRNA bound LNA probes were detected by fast red substrate (Panomics). After counterstaining with DAPI, slides were mounted using FluorSave (Merck). Image acquisition was performed with Olympus FluoView FV1000 using TRITC filter.

In Vivo Lung Metastasis Assay

Six- to eight-week-old female NOD-scid IL2Re$^{null}$ inbred mice were obtained from Jackson Laboratories, Bar Harbor, Me., USA and housed in a specific pathogen-free animal facility. The animals were fed with irradiated mouse chow and autoclaved reverse osmosis treated water. All the animal procedures were performed in accordance with a protocol approved by the Institutional Animal Care and Usage Committee (IACUC #120793). A253 cells constitutively expressing luciferase, transduced with lentiviruses expressing control shRNA or shRNAs against FSTL1, or DIAPH1 or a combination of both FSTL1 and DIAPH1, were harvested with trypsin/EDTA. Cells were washed and re-suspended at a concentration of $5\times10^6$ cells per ml. A total of $0.5\times10^6$ cells were injected into mice via tail vein and cohorts of 7 mice were used in each group. Survival and successful injection of the cells was monitored by detection of bioluminescence in the lungs after 24 hours using IVIS Spectrum in vivo Imaging System (Xenogen, Perkin Elmer, Mass., USA). In each imaging session, a total of 150 mg of Luciferin per kg body weight was administered into the peritoneal cavity. Mice were imaged 9 minutes after Luciferin injection to ensure consistent photon flux. The bioluminescent signal was expressed in photons per second and displayed as an intensity map. The image display was adjusted to provide optimal contrast and resolution in the image without affecting quantitation. Following acquisition, all images were normalized to units of average efficiency, displayed in the same scale of luminescence intensity, and analysed using the Living Image 4 software (Xenogen, Perkin Elmer, Mass., USA). Luminescence from the cells was measured in the lungs using a region of interest tool. This quantification was plotted as Relative Bioluminescence Units against time. The data were expressed as mean±standard deviation (SD). Statistical analysis was estimated using Student's t-test method. The values with $p<0.05$ were interpreted to be significant. 30 days post injection mice were euthanized, lungs were harvested, fixed and processed into FFPE blocks. Cancer cells in micro-metastatic foci were detected by immunohistochemistry using a rabbit-anti-human KRT5 antibody.

Zymography

20 µl of cell culture supernatant was loaded and resolved on to SDS-PAGE containing 0.15% gelatin followed by two washes in 2.5% Triton x 100. Gel was soaked in a developer buffer containing 50 mM Tris HCl pH 7.4, 150 mM NaCl and 10 mM $CaCl_2$) overnight at 37° C. and visualized by staining the gel in 0.2% Coomassie brilliant blue R-250 for 1 hour followed by multiple de-staining rounds in 30% methanol and 7% acetic acid. Band intensity was quantified by Image J and plotted after normalizing the values to background intensity. The position of MMP9 was identified by co-migration of recombinant MMP9 in the same gel.

Biotin-Streptavidin Affinity Purification of DIAPH1 Interacting Partners

Full-length cDNA for DIAPH1 (accession no: NM_005219) was purchased from Origene. DIAPH1 ORF was PCR amplified and cloned as a fusion protein N-terminally with a myc-tagged BirA in pTRIPZ vector system. The entire myc-BirA-DIAPH1 cassette is under the control of Tetracycline inducible promoter system (Tet-ON) for the stringent control of fusion protein expression. For affinity purification of biotinylated interacting partners of DIAPH1, 293T cells were transfected with 20 µg of plasmid DNA using calcium phosphate transfection method. Cells were selected with puromycin (2 m/ml) and 72 hrs post-transfection cells were supplemented with Doxycycline (Dox) (5 m/ml) for 24 hrs to induce transgene expression. In order to induce biotinylation of interacting partners, 50 µM of biotin was added to cells and incubated for 24 hours. Cells were harvested by trypsinization and subjected to biotin affinity capture purification (BioID) (Roux et al., 2013). Briefly, cells were lysed in buffer containing 50 mM Tris Cl (pH 7.4), 500 mM NaCl, 0.2% SDS with 1× protease inhibitor cocktail (Roche). After clarifying the cell debris by centrifugation, lysates were incubated with Dynabeads (MyOne Streptavidine C1, Life Technologies) overnight. Unbound and non-specific proteins were removed following wash buffer formulation as described in the art. After final wash with 50 mM Tris Cl (pH 7.4), proteins bound to beads were subjected to mass spectrometry analysis as described below. For initial validation of BioID methodology, cells were transfected in coverslips as above. The fusion protein and biotinylated proteins were detected by Rabbit anti-myc and streptavidin conjugated Alexaflour-555 (Invitrogen), respectively.

Mass Spectrometry and Data Analysis

For mass spectrometric analysis, proteins bound to streptavidin beads were digested on-bead following protocols known in the art. The peptides were separated using a gradient of 2% to 80% acetonitrile in 0.1% formic acid at a flow rate of ~350 nL/min. Data was collected by Orbitrap Fusion™ Tribrid™ Mass Spectrometer (MS) (ThermoFisher Scientific, San Jose, Calif.) and proxeon EASY-nLC 1000 liquid chromatography (LC-MS/MS). Raw data was analyzed using Proteome Discoverer (Version 1.4.0.288 Thermo Fisher Scientific) and Scaffold 4.1 (Proteome Software, Portland, Oreg.) with mascot search engine. (http://www.uniprot.org/uniprot/?query=Human&sort=score).

The peptide spectral matches (PSM) were validated using percolator based on q-values at a 1% false discovery rate (FDR). For protein identification, a high-confidence database search with peptide target FDR (strict) of 0.1%, and target FDR (relaxed) 0.5% and ranked peptides were used for peptide filtering. Identified peptides were grouped into individual protein cluster by Scaffold. The list of proteins obtained by this method was further shortlisted. Proteins identified in cells without dox treatment but with biotin, proteins commonly found in BioID methodology and proteins with less than 8% peptide coverage were subtracted from the list.

BioGRID Analysis

[http://thebiogrid.org/116338/summary/homo-sapiens/fstl1.html] BioGRID version 3.4.134 was used to predict the interacting partners of FSTL1 protein.

Co-Immunoprecipitation and Western Blotting:

Total cell extract was prepared from A253 cells by directly lysing the cells in RIPA buffer in culture wells. Cells were lysed at 5 pulses of sonication followed by clarification at 16,000 RCF for 10 minutes at 4° C. Co-immunoprecipitation analysis for selected proteins was performed using a co-immunoprecipitation kit (Peirce) as per the manufacturer's recommendations. Proteins bound to beads were eluted in Lamelli buffer, resolved through 10% SDS-PAGE and subjected to Western blot analysis. Proteins were detected by chemiluminescence.

Live Cell Imaging $10\times10^3$ cells were seeded in a glass bottom culture dish (Ibidi GmbH) for 24 hours. A drop of Nucblue live cell stain (Life Technologies; R37605) was added to the cells in the culture medium and incubated for 30 minutes. The cells were washed with PBS and fresh medium was added. The live cell migration was followed for 24 hours, using Olympus IX-83 LCI RM 5.17 live cell imaging system. The data was processed and analysed using Imaris 8.1.2 software tool.

Data-driven grouping method (DDg): One-dimensional data-driven grouping (1DDDg) method is a computational and statistical approach to identify an optimal expression cut-off on a linear scale that provides maximal and most statistically significant stratification of the survival curves. Two-dimensional data-driven grouping (2D-DDg) method further extends the idea of 1DDg, and evaluates the potential synergistic effect of gene-pairs in patient prognosis. Briefly, 2D-DDg identifies one expression cut-off on each orthogonal axis (each representing one gene of the gene-pair) that collectively could stratify patients into two subgroups with the most significantly different survival curves. The methods of 1DDg and 2DDg were previously used to identify and experimentally validate molecular signatures of ovarian cancer, breast cancer, as well as used in evaluating the survival significance of gene features in glioblastoma.

Gel Retardation Assay

The pre-miR-198 substrate for gel retardation assay was prepared as described earlier. The U-rich element present within pre-miR-198 sequence were converted to C residues (See SEQ ID NO: 19 and 20 in the table below) using Quick change site directed mutagenesis Kit. Increasing concentration of recombinant HuR protein (0.2, 0.4 and 0.6 μM) was incubated with the wild type or mutant pre-miR-198 transcripts in 20 μl of reaction buffer containing 30 mM Tris HCl, pH 7.4, 5 mM $MgCl_2$, 50 mM KCl, 0.5 mM DTT, 40 U/ml of RNaseOUT, 250 μg/ml of yeast tRNA and 10% glycerol. After 30 minutes at room temperature, reaction products were resolved through 6% native polyacrylamide gel electrophoresis. For competitive binding assay, 0.2 μM of KSRP was co-incubated with indicated concentration of HuR in the presence of pre-miR-198 transcript. The resulting gel was dried and the protein RNA complex and unbound RNA were visualized by phosphor-imaging.

In Vitro Transcription and Translation

Generation of pMIRGLO dual luciferase containing FSTL1 3'-untranslated region (UTR) downstream of firefly luciferase open reading frame was performed as described in the art. Primers with T7 RNA polymerase promoter linkers (see paragraph 00176 for sequence table) were used to amplify the entire luciferase-FSTL1 3'-UTR fragment along with the Kozak sequence. A PCR fragment containing the copGFP ORF was amplified from pCDH vector (System biosciences), using primers listed in tables section. PCR products were purified and subjected to in vitro transcription with Ambion mMessage mMachine kit. For in vitro translation, 500 ng of purified Luc-FSTL1 chimeric RNA and 200 ng of GFP RNA was added to 30 μl of rabbit reticulocyte lysate, 20 μM of methionine free amino acid mixture, 50 μCi of Easy tag Express 35S protein labeling mix and 10 μg of cell extract in a total volume of 50 μl for 1 hour at 30° C. 10 μl aliquot of the reaction mix was separated on 10% SDS-PAGE, fixed in 10% acetic acid/40% methanol, dried and exposed to phosphorimaging.

Statistical Analysis—Values are Reported as the Mean±the Standard Error

Statistical significance between 2 samples was determined with two-tailed Student's t-test or one-way analysis of variance (ANOVA) when comparing multiple groups. Statistical significance between 2 samples was determined with two-tailed Student's t test using GraphPad InStat 3.0 software (GraphPad Software, Inc.). For tissue arrays, chi square analysis was performed as described in the art. Values were reposted as mean±standard error.

Sequences

Table of sequences: unless otherwise stated, nucleic acid sequences are provided in 5' to 3' direction and peptide sequences are provided from N- to C-terminus according to convention.

| SEQ ID NO: | Description | Sequence |
| --- | --- | --- |
| 1 | Human microRNA-198 (miRNA-198) DNA sequence | GGTCCAGAGG GGAGATAGGTTC |
| 2 | 5' section of human microRNA-198 (miRNA-198) | GTCCAGAG |
| 3 | Follistatin-related protein 1 (FSTL1) | MWKRWLALALALVAVAWVRAEEELRSKS KICANVFCGAGRECAVTEKGEPTCLCIEQCK PHKRPVCGSNGKTYLNHCELHRDACLTGSK IQVDYDGHCKEKKSVSPSASPVVCYQSNRD ELRRRIIQWLEAEIIPDGWFSKGSNYSEILDK YFKNFDNGDSRLDSSEFLKFVEQNETAINIT TYPDQENNKLLRGLCVDALIELSDENADWK LSFQEFLKCLNPSFNPPEKKCALEDETYADG AETEVDCNRCVCACGNWVCTAMTCDGKN QKGAQTQTEEEMTRYVQELQKHQETAEKT KRVSTKEI |
| 4 | Protein diaphanous homolog 1 (DIAPH1) | MEPPGGSLGPGRGTRDKKKGRSPDELPSAG GDGGKSKKFTLKRLMADELERFTSMRIKKE KEKPNSAHRNSSASYGDDPTAQSLQDVSDE QVLVLFEQMLLDMNLNEEKQQPLREKDIIIK REMVSQYLYTSKAGMSQKESSKSAMMYIQ ELRSGLRDMPLLSCLESLRVSLNNNPVSWV QTFGAEGLASLLDILKRLHDEKEETAGSYDS RNKHEIIRCLKAFMNNKFGIKTMLETEEGIL LLVRAMDPAVPNMMIDAAKLLSALCILPQP EDMNERVLEAMTERAEMDEVERFQPLLDG LKSGTTIALKVGCLQLINALITPAEELDFRVH IRSELMRLGLHQVLQDLREIENEDMRVQLN VPDEQGEEDSYDLKGRLDDIRMEMDDFNE VFQILLNTVKDSKAEPHFLSILQHLLLVRND YEARPQYYKLIEECISQIVLHKNGADPDFKC RHLQIEIEGLIDQMIDKTKVEKSEAKAAELE KKLDSELTARHELQVEMKKMESDFEQKLQ DLQGEKDALHSEKQQIATEKQDLEAEVSQL TGEVAKLTKELEDAKKEMASLSAAAITVPP |

| SEQ ID NO: | Description | Sequence |
|---|---|---|
| | | SVPSRAPVPPAPPLPGDSGTIIPPPPAPGDSTT PPPPPPPPPPPPLPGGVCISSPPSLPGGTAISP PPPLSGDATIPPPPPLPEGVGIPSPSSLPGGTAI PPPPPLPGSARIPPPPPPLPGSAGIPPPPPPLPG EAGMPPPPPPLPGGPGIPPPPPFPGGPGIPPPP PGMGMPPPPPPFGFGVPAAPVLPFGLTPKKLY KPEVQLRRPNWSKLVAEDLSQDCFWTKVK EDRFENNELFAKLTLTFSAQTKTSKAKKDQ EGGEEKKSVQKKKVKELKVLDSKTAQNLSI FLGSFRMPYQEIKNVILEVNEAVLTESMIQN LIKQMPEPEQLKMLSELKDEYDDLAESEQF GVVMGTVPRLRPRLNAILFKLQFSEQVENIK PEIVSVTAACEELRKSESFSNLLEITLLVGNY MNAGSRNAGAFGFNISFLCKLRDTKSTDQK MTLLHFLAELCENDYPDVLKFPDELAHVEK ASRVSAENLQKNLDQMKKQISDVERDVQN FPAATDEKDKFVEKMTSFVKDAQEQYNKL RMMHSNMETLYKELGEYFLFDPKKLSVEEF FMDLHNFRNMFLQAVKENQKRRETEEKMR RAKLAKEKAEKERLEKQQKREQLIDMNAE GDETGVMDSLLEALQSGAAFRRKRGPRQA NRKAGCAVTSLLASELTKDDAMAAVPAKV SKNSETFPTILEEAKELVGRAS |
| 5 | Laminin subunit gamma-2 (LAMC2) | MPALWLGCCLCFSLLLPAARATSRREVCDC NGKSRQCIFDRELHRQTGNGFRCLNCNDNT DGIHCEKCKNGFYRHRERDRCLPCNCNSKG SLSARCDNSGRCSCKPGVTGARCDRCLPGF HMLTDAGCTQDQRLLDSKCDCDPAGIAGPC DAGRCVCKPAVTGERCDRCRSGYYNLDGG NPEGCTQCFCYGHSASCRSSAEYSVHKITST FHQDVDGWKAVQRNGSPAKLQWSQRHQD VFSSAQRLDPVYFVAPAKFLGNQQVSYGQS LSFDYRVDRGGRHPSAHDVILEGAGLRITAP LMPLGKTLPCGLTKTYTFRLNEHPSNNWSP QLSYFEYRRLLRNLTALRIRATYGEYSTGYI DNVTLISARPVSGAPAPWVEQCICPVGYKG QFCQDCASGYKRDSARLGPFGTCIPCNCQG GGACDPDTGDCYSGDENPDIECADCPIGFY NDPHDPRSCKPCPCHNGFSCSVMPETEEVV CNNCPPGVTGARCELCADGYFGDPFGEHGP VRPCQPCQCNNNVDPSASGNCDRLTGRCLK CIHNTAGIYCDQCKAGYFGDPLAPNPADKC RACNCNPMGSEPVGCRSDGTCVCKPGFGGP NCEHGAFSCPACYNQVKIQMDQFMQQLQR MEALISKAQGGDGVVPDTELEGRMQQAEQ ALQDILRDAQISEGASRSLGLQLAKVRSQEN SYQSRLDDLKMTVERVRALGSQYQNRVRD THRLITQMQLSLAESEASLGNTNIPASDHYV GPNGFKSLAQEATRLAESHVESASNMEQLT RETEDYSKQALSLVRKALHEGVGSGSGSPD GAVVQGLVEKLEKTKSLAQQLTREATQAEI EADRSYQHSLRLLDSVSRLQGVSDQSFQVE EAKRIKQKADSLSSLVTRHMDEFKRTQKNL GNWKEEAQQLLQNGKSGREKSDQLLSRAN LAKSRAQEALSMGNATFYEVESILKNLREF DLQVDNRKAEAEEAMKRLSYISQKVSDASD KTQQAERALGSAAADAQRAKNGAGEALEIS SETEQEIGSLNLEANVTADGALAMEKGLASL KSEMREVEGELERKELEFDTNMDAVQMVIT EAQKVDTRAKNAGVTIQDTLNTLDGLLHL MDQPLSVDEEGLVLLEQKLSRAKTQINSQL RPMMSELEEERARQQRGHLHLLETSIDGILAD VKNLENIRDNLPPGCYNTQALEQQ |
| 6 | Urokinase-type plasminogen activator (PLAU) | MRALLARLLLCVLVVSDSKGSNELHQVPSN CDCLNGGTCVSNKYFSNIHWCNCPKKFGGQ HCEIDKSKTCYEGNGHFYRGKASTDTMGRP CLPWNSATVLQQTYHAHRSDALQLGLGKH NYCRNPDNRRRPWCYVQVGLKPLVQECMV HDCADGKKPSSPPEELKFQCGQKTLRPRFKI IGGEFTTIENQPWFAAIYRRHRGGSVTYVCG GSLISPCWVISATHCFIDYPKKEDYIVYLGRS RLNSNTQGEMKFEVENLILHKDYSADTLAH HNDIALLKIRSKEGRCAQPSRTIQTICLPSMY NDPQFGTSCEITGFGKENSTDYLYPEQLKMT |

| SEQ ID NO: | Description | Sequence |
|---|---|---|
| | | VVKLISHRECQQPHYYGSEVTTKMLCAADP QWKTDSCQGDSGGPLVCSLQGRMTLTGIVS WGRGCALKDKPGVYTRVSHFLPWIRSHTKE ENGLAL |
| 7 | siRNA sequence FSTL1 | CGGATACTATTGATGAATAA |
| 8 | siRNA sequence LAMC2 | AGAATCCTGACATTGAGTGT |
| 9 | siRNA sequence DIAPH1 | CTGCATGTGAGGAGTTACGT |
| 10 | siRNA sequence PLAU | AATTCTACCGACTATCTCTA |
| 11 | Sequence of Pre-miR-198 WT probe | TCATTGGTCCAGAGGGGAGATAGGTTCCT GTGATTTTTCCTTCTTCTCTATAGAATAAA TGA |
| 12 | Sequence of Pre-miR-198 WT probe | TCATTGGTCCAGAGGGGAGATAGGTTCCT GTGACCCCCCCTTCTTCTCTATAGAATAAA T GA |
| 13 | Luciferase T7 forward primer (binds 9 base pairs upstream of Luciferase AUG in pMIRGLO. Includes the Kozak sequence) | TAATACGACTCACTATAGGGAAAGCCACC ATGGAAGATGCC |
| 14 | FSTL1 3' UTR reverse primer (Binds to position 2617 in FSTL1 3'UTR) | CCG AAA AGG AAG AAT CAG GAG |
| 15 | CopGFP start T7F primer | TAATACGACTCACTATAGGG cta gac gcc acc atg gag agc |
| 16 | CopGFP stop R | GTCGACTTAGCGAGATCCGGTG |
| 17 | Human microRNA-198 (miRNA-198)-RNA sequence | GGUCCAGAGG GGAGAUAGGU UC |
| 18 | Human microRNA-198 (miRNA-198)-Seed sequence | GUCCAGAG |
| 19 | Pre-miR-198 WT | TCATTGGTCCAGAGGGGAGATAGGTTCCT GTGATTTTTCCTTCTTCTCTATAGAATAAA TGA |
| 20 | Pre-miR-198 Mut | TCATTGGTCCAGAGGGGAGATAGGTTCCT GTGACCCCCCCTTCTTCTCTATAGAATAA ATGA |

---

What is claimed is:

1. A method of treating cutaneous squamous cell carcinoma or head and neck squamous cell carcinoma, wherein the method comprises administration of one or more oligonucleotides comprising or consisting of the sequence of miR-198 (SEQ ID:
  1), a functional part thereof, or a combination thereof, an siRNA or shRNA molecule which reduces expression of follistatin-related protein 1 (FSTL1), wherein the siRNA or shRNA molecule comprises the sequence of SEQ ID NO: 7, wherein the functional part comprises or consists of 5'GTCCAGAG 3' (SEQ ID NO: 2).

2. The method of claim 1, wherein the oligonucleotide is unmodified, or is modified with one or more chemical groups selected from the group consisting of 2'O-methoxy, phosphorothioate, locked nucleic acid and cholesterol.

* * * * *

SEQUENCE LISTING

<160> NUMBER OF SEQ ID NOS: 20

<210> SEQ ID NO 1
<211> LENGTH: 22
<212> TYPE: DNA
<213> ORGANISM: Artificial sequence
<220> FEATURE:
<223> OTHER INFORMATION: Human microRNA-198 (miRNA-198) DNA sequence

<400> SEQUENCE: 1
ggtccagagg ggagataggt tc         22

<210> SEQ ID NO 2
<211> LENGTH: 8
<212> TYPE: DNA
<213> ORGANISM: Artificial sequence
<220> FEATURE:
<223> OTHER INFORMATION: 5' section of human microRNA-198 (miRNA-198)

<400> SEQUENCE: 2 gtccagag                                                                    8

<210> SEQ ID NO 3
<211> LENGTH: 308
<212> TYPE: PRT
<213> ORGANISM: Artificial sequence
<220> FEATURE:
<223> OTHER INFORMATION: Follistatin-related protein 1 (FSTL1)

<400> SEQUENCE: 3

Met Trp Lys Arg Trp Leu Ala Leu Ala Leu Ala Leu Ala Val Ala Ala
1               5                   10                  15

Trp Val Arg Ala Glu Glu Glu Leu Arg Ser Lys Ser Lys Ile Cys Ala
            20                  25                  30

Asn Val Phe Cys Gly Ala Gly Arg Glu Cys Ala Val Thr Glu Lys Gly
        35                  40                  45

Glu Pro Thr Cys Leu Cys Ile Glu Gln Cys Lys Pro His Lys Arg Pro
    50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Arg Ile Ile Gln Trp
        115                 120                 125

Leu Glu Ala Glu Ile Ile Pro Asp Gly Trp Phe Ser Lys Gly Ser Asn
    130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
    210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Met Thr Arg Tyr Val Gln
        275                 280                 285

Glu Leu Gln Lys His Gln Glu Thr Ala Glu Lys Thr Lys Arg Val Ser
    290                 295                 300

Thr Lys Glu Ile
305

<210> SEQ ID NO 4
<211> LENGTH: 1272
<212> TYPE: PRT
<213> ORGANISM: Artificial sequence
<220> FEATURE:
<223> OTHER INFORMATION: Protein diaphanous homolog 1 (DIAPH1)

<400> SEQUENCE: 4

```
Met Glu Pro Pro Gly Gly Ser Leu Gly Pro Gly Arg Gly Thr Arg Asp
1               5                   10                  15

Lys Lys Lys Gly Arg Ser Pro Asp Glu Leu Pro Ser Ala Gly Gly Asp
            20                  25                  30

Gly Gly Lys Ser Lys Lys Phe Thr Leu Lys Arg Leu Met Ala Asp Glu
        35                  40                  45

Leu Glu Arg Phe Thr Ser Met Arg Ile Lys Lys Glu Lys Glu Lys Pro
50                  55                  60

Asn Ser Ala His Arg Asn Ser Ser Ala Ser Tyr Gly Asp Asp Pro Thr
65                  70                  75                  80

Ala Gln Ser Leu Gln Asp Val Ser Asp Glu Gln Val Leu Val Leu Phe
                85                  90                  95

Glu Gln Met Leu Leu Asp Met Asn Leu Asn Glu Glu Lys Gln Gln Pro
            100                 105                 110

Leu Arg Glu Lys Asp Ile Ile Ile Lys Arg Glu Met Val Ser Gln Tyr
        115                 120                 125

Leu Tyr Thr Ser Lys Ala Gly Met Ser Gln Lys Glu Ser Ser Lys Ser
130                 135                 140

Ala Met Met Tyr Ile Gln Glu Leu Arg Ser Gly Leu Arg Asp Met Pro
145                 150                 155                 160

Leu Leu Ser Cys Leu Glu Ser Leu Arg Val Ser Leu Asn Asn Asn Pro
                165                 170                 175

Val Ser Trp Val Gln Thr Phe Gly Ala Glu Gly Leu Ala Ser Leu Leu
            180                 185                 190

Asp Ile Leu Lys Arg Leu His Asp Glu Lys Glu Thr Ala Gly Ser
        195                 200                 205

Tyr Asp Ser Arg Asn Lys His Glu Ile Ile Arg Cys Leu Lys Ala Phe
210                 215                 220

Met Asn Asn Lys Phe Gly Ile Lys Thr Met Leu Glu Thr Glu Glu Gly
225                 230                 235                 240

Ile Leu Leu Leu Val Arg Ala Met Asp Pro Ala Val Pro Asn Met Met
                245                 250                 255

Ile Asp Ala Ala Lys Leu Leu Ser Ala Leu Cys Ile Leu Pro Gln Pro
            260                 265                 270

Glu Asp Met Asn Glu Arg Val Leu Glu Ala Met Thr Glu Arg Ala Glu
        275                 280                 285

Met Asp Glu Val Glu Arg Phe Gln Pro Leu Leu Asp Gly Leu Lys Ser
290                 295                 300

Gly Thr Thr Ile Ala Leu Lys Val Gly Cys Leu Gln Leu Ile Asn Ala
305                 310                 315                 320

Leu Ile Thr Pro Ala Glu Glu Leu Asp Phe Arg Val His Ile Arg Ser
                325                 330                 335

Glu Leu Met Arg Leu Gly Leu His Gln Val Leu Gln Asp Leu Arg Glu
            340                 345                 350

Ile Glu Asn Glu Asp Met Arg Val Gln Leu Asn Val Phe Asp Glu Gln
        355                 360                 365

Gly Glu Glu Asp Ser Tyr Asp Leu Lys Gly Arg Leu Asp Asp Ile Arg
370                 375                 380

Met Glu Met Asp Asp Phe Asn Glu Val Phe Gln Ile Leu Leu Asn Thr
385                 390                 395                 400
```

```
Val Lys Asp Ser Lys Ala Glu Pro His Phe Leu Ser Ile Leu Gln His
            405                 410                 415

Leu Leu Leu Val Arg Asn Asp Tyr Glu Ala Arg Pro Gln Tyr Tyr Lys
                420                 425                 430

Leu Ile Glu Glu Cys Ile Ser Gln Ile Val Leu His Lys Asn Gly Ala
            435                 440                 445

Asp Pro Asp Phe Lys Cys Arg His Leu Gln Ile Glu Ile Glu Gly Leu
        450                 455                 460

Ile Asp Gln Met Ile Asp Lys Thr Lys Val Glu Lys Ser Glu Ala Lys
465                 470                 475                 480

Ala Ala Glu Leu Glu Lys Lys Leu Asp Ser Glu Leu Thr Ala Arg His
                485                 490                 495

Glu Leu Gln Val Glu Met Lys Lys Met Glu Ser Asp Phe Glu Gln Lys
            500                 505                 510

Leu Gln Asp Leu Gln Gly Glu Lys Asp Ala Leu His Ser Glu Lys Gln
        515                 520                 525

Gln Ile Ala Thr Glu Lys Gln Asp Leu Glu Ala Glu Val Ser Gln Leu
530                 535                 540

Thr Gly Glu Val Ala Lys Leu Thr Lys Glu Leu Glu Asp Ala Lys Lys
545                 550                 555                 560

Glu Met Ala Ser Leu Ser Ala Ala Ala Ile Thr Val Pro Pro Ser Val
                565                 570                 575

Pro Ser Arg Ala Pro Val Pro Pro Ala Pro Leu Pro Gly Asp Ser
            580                 585                 590

Gly Thr Ile Ile Pro Pro Pro Ala Pro Gly Asp Ser Thr Thr Pro
            595                 600                 605

Pro Pro Pro Pro Pro Pro Pro Pro Pro Pro Leu Pro Gly Gly
        610                 615                 620

Val Cys Ile Ser Ser Pro Pro Ser Leu Pro Gly Gly Thr Ala Ile Ser
625                 630                 635                 640

Pro Pro Pro Pro Leu Ser Gly Asp Ala Thr Ile Pro Pro Pro Pro
                645                 650                 655

Leu Pro Glu Gly Val Gly Ile Pro Ser Pro Ser Ser Leu Pro Gly Gly
            660                 665                 670

Thr Ala Ile Pro Pro Pro Pro Leu Pro Gly Ser Ala Arg Ile Pro
            675                 680                 685

Pro Pro Pro Pro Leu Pro Gly Ser Ala Gly Ile Pro Pro Pro
        690                 695                 700

Pro Pro Leu Pro Gly Glu Ala Gly Met Pro Pro Pro Pro Pro Leu
705                 710                 715                 720

Pro Gly Gly Pro Gly Ile Pro Pro Pro Pro Phe Pro Gly Gly Pro
            725                 730                 735

Gly Ile Pro Pro Pro Pro Gly Met Gly Met Pro Pro Pro Pro
            740                 745                 750

Phe Gly Phe Gly Val Pro Ala Ala Pro Val Leu Pro Phe Gly Leu Thr
            755                 760                 765

Pro Lys Lys Leu Tyr Lys Pro Glu Val Gln Leu Arg Arg Pro Asn Trp
    770                 775                 780

Ser Lys Leu Val Ala Glu Asp Leu Ser Gln Asp Cys Phe Trp Thr Lys
785                 790                 795                 800

Val Lys Glu Asp Arg Phe Glu Asn Asn Glu Leu Phe Ala Lys Leu Thr
                805                 810                 815
```

```
Leu Thr Phe Ser Ala Gln Thr Lys Thr Ser Lys Ala Lys Lys Asp Gln
            820                 825                 830

Glu Gly Gly Glu Glu Lys Lys Ser Val Gln Lys Lys Val Lys Glu
        835                 840                 845

Leu Lys Val Leu Asp Ser Lys Thr Ala Gln Asn Leu Ser Ile Phe Leu
850                 855                 860

Gly Ser Phe Arg Met Pro Tyr Gln Glu Ile Lys Asn Val Ile Leu Glu
865                 870                 875                 880

Val Asn Glu Ala Val Leu Thr Glu Ser Met Ile Gln Asn Leu Ile Lys
                885                 890                 895

Gln Met Pro Glu Pro Glu Gln Leu Lys Met Leu Ser Glu Leu Lys Asp
                900                 905                 910

Glu Tyr Asp Asp Leu Ala Glu Ser Glu Gln Phe Gly Val Val Met Gly
            915                 920                 925

Thr Val Pro Arg Leu Arg Pro Arg Leu Asn Ala Ile Leu Phe Lys Leu
        930                 935                 940

Gln Phe Ser Glu Gln Val Glu Asn Ile Lys Pro Glu Ile Val Ser Val
945                 950                 955                 960

Thr Ala Ala Cys Glu Glu Leu Arg Lys Ser Glu Ser Phe Ser Asn Leu
                965                 970                 975

Leu Glu Ile Thr Leu Leu Val Gly Asn Tyr Met Asn Ala Gly Ser Arg
            980                 985                 990

Asn Ala Gly Ala Phe Gly Phe Asn  Ile Ser Phe Leu Cys  Lys Leu Arg
        995                 1000                1005

Asp Thr  Lys Ser Thr Asp Gln  Lys Met Thr Leu Leu  His Phe Leu
    1010                1015                1020

Ala Glu  Leu Cys Glu Asn Asp  Tyr Pro Asp Val Leu  Lys Phe Pro
    1025                1030                1035

Asp Glu  Leu Ala His Val Glu  Lys Ala Ser Arg Val  Ser Ala Glu
    1040                1045                1050

Asn Leu  Gln Lys Asn Leu Asp  Gln Met Lys Lys Gln  Ile Ser Asp
    1055                1060                1065

Val Glu  Arg Asp Val Gln Asn  Phe Pro Ala Ala Thr  Asp Glu Lys
    1070                1075                1080

Asp Lys  Phe Val Glu Lys Met  Thr Ser Phe Val Lys  Asp Ala Gln
    1085                1090                1095

Glu Gln  Tyr Asn Lys Leu Arg  Met Met His Ser Asn  Met Glu Thr
    1100                1105                1110

Leu Tyr  Lys Glu Leu Gly Glu  Tyr Phe Leu Phe Asp  Pro Lys Lys
    1115                1120                1125

Leu Ser  Val Glu Glu Phe Phe  Met Asp Leu His Asn  Phe Arg Asn
    1130                1135                1140

Met Phe  Leu Gln Ala Val Lys  Glu Asn Gln Lys Arg  Arg Glu Thr
    1145                1150                1155

Glu Glu  Lys Met Arg Arg Ala  Lys Leu Ala Lys Glu  Lys Ala Glu
    1160                1165                1170

Lys Glu  Arg Leu Glu Lys Gln  Gln Lys Arg Glu Gln  Leu Ile Asp
    1175                1180                1185

Met Asn  Ala Glu Gly Asp Glu  Thr Gly Val Met Asp  Ser Leu Leu
    1190                1195                1200

Glu Ala  Leu Gln Ser Gly Ala  Ala Phe Arg Arg Lys  Arg Gly Pro
    1205                1210                1215

Arg Gln  Ala Asn Arg Lys Ala  Gly Cys Ala Val Thr  Ser Leu Leu
```

-continued

```
              1220                1225                1230

Ala Ser Glu Leu Thr Lys Asp Asp Ala Met Ala Ala Val Pro Ala
        1235                1240                1245

Lys Val Ser Lys Asn Ser Glu Thr Phe Pro Thr Ile Leu Glu Glu
    1250                1255                1260

Ala Lys Glu Leu Val Gly Arg Ala Ser
    1265                1270

<210> SEQ ID NO 5
<211> LENGTH: 1193
<212> TYPE: PRT
<213> ORGANISM: Artificial sequence
<220> FEATURE:
<223> OTHER INFORMATION: Laminin subunit gamma-2 (LAMC2)

<400> SEQUENCE: 5

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
```

```
                    305                 310                 315                 320
                Glu His Pro Ser Asn Asn Trp Ser Pro Gln Leu Ser Tyr Phe Glu Tyr
                                325                 330                 335
                Arg Arg Leu Leu Arg Asn Leu Thr Ala Leu Arg Ile Arg Ala Thr Tyr
                                340                 345                 350
                Gly Glu Tyr Ser Thr Gly Tyr Ile Asp Asn Val Thr Leu Ile Ser Ala
                                355                 360                 365
                Arg Pro Val Ser Gly Ala Pro Ala Pro Trp Val Glu Gln Cys Ile Cys
                370                 375                 380
                Pro Val Gly Tyr Lys Gly Gln Phe Cys Gln Asp Cys Ala Ser Gly Tyr
                385                 390                 395                 400
                Lys Arg Asp Ser Ala Arg Leu Gly Pro Phe Gly Thr Cys Ile Pro Cys
                                405                 410                 415
                Asn Cys Gln Gly Gly Ala Cys Asp Pro Asp Thr Gly Asp Cys Tyr
                                420                 425                 430
                Ser Gly Asp Glu Asn Pro Asp Ile Glu Cys Ala Asp Cys Pro Ile Gly
                                435                 440                 445
                Phe Tyr Asn Asp Pro His Asp Pro Arg Ser Cys Lys Pro Cys Pro Cys
                450                 455                 460
                His Asn Gly Phe Ser Cys Ser Val Met Pro Glu Thr Glu Val Val
                465                 470                 475                 480
                Cys Asn Cys Pro Pro Gly Val Thr Gly Ala Arg Cys Glu Leu Cys
                                485                 490                 495
                Ala Asp Gly Tyr Phe Gly Asp Pro Phe Gly Glu His Gly Pro Val Arg
                                500                 505                 510
                Pro Cys Gln Pro Cys Gln Cys Asn Asn Asn Val Asp Pro Ser Ala Ser
                                515                 520                 525
                Gly Asn Cys Asp Arg Leu Thr Gly Arg Cys Leu Lys Cys Ile His Asn
                                530                 535                 540
                Thr Ala Gly Ile Tyr Cys Asp Gln Cys Lys Ala Gly Tyr Phe Gly Asp
                545                 550                 555                 560
                Pro Leu Ala Pro Asn Pro Ala Asp Lys Cys Arg Ala Cys Asn Cys Asn
                                565                 570                 575
                Pro Met Gly Ser Glu Pro Val Gly Cys Arg Ser Asp Gly Thr Cys Val
                                580                 585                 590
                Cys Lys Pro Gly Phe Gly Gly Pro Asn Cys Glu His Gly Ala Phe Ser
                                595                 600                 605
                Cys Pro Ala Cys Tyr Asn Gln Val Lys Ile Gln Met Asp Gln Phe Met
                                610                 615                 620
                Gln Gln Leu Gln Arg Met Glu Ala Leu Ile Ser Lys Ala Gln Gly Gly
                625                 630                 635                 640
                Asp Gly Val Val Pro Asp Thr Glu Leu Glu Gly Arg Met Gln Gln Ala
                                645                 650                 655
                Glu Gln Ala Leu Gln Asp Ile Leu Arg Asp Ala Gln Ile Ser Glu Gly
                                660                 665                 670
                Ala Ser Arg Ser Leu Gly Leu Gln Leu Ala Lys Val Arg Ser Gln Glu
                                675                 680                 685
                Asn Ser Tyr Gln Ser Arg Leu Asp Asp Leu Lys Met Thr Val Glu Arg
                                690                 695                 700
                Val Arg Ala Leu Gly Ser Gln Tyr Gln Asn Arg Val Arg Asp Thr His
                705                 710                 715                 720
                Arg Leu Ile Thr Gln Met Gln Leu Ser Leu Ala Glu Ser Glu Ala Ser
                                725                 730                 735
```

```
Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
            770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                    805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
            850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                    885                 890                 895

Lys Asn Leu Gly Asn Trp Lys Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
            930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
            965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
            995                 1000                1005

Asn Gly Ala Gly Glu Ala Leu Glu Ile Ser Ser Glu Ile Glu Gln
            1010                1015                1020

Glu Ile Gly Ser Leu Asn Leu Glu Ala Asn Val Thr Ala Asp Gly
            1025                1030                1035

Ala Leu Ala Met Glu Lys Gly Leu Ala Ser Leu Lys Ser Glu Met
            1040                1045                1050

Arg Glu Val Glu Gly Glu Leu Glu Arg Lys Glu Leu Glu Phe Asp
            1055                1060                1065

Thr Asn Met Asp Ala Val Gln Met Val Ile Thr Glu Ala Gln Lys
            1070                1075                1080

Val Asp Thr Arg Ala Lys Asn Ala Gly Val Thr Ile Gln Asp Thr
            1085                1090                1095

Leu Asn Thr Leu Asp Gly Leu His Leu Met Asp Gln Pro Leu
            1100                1105                1110

Ser Val Asp Glu Glu Gly Leu Val Leu Leu Glu Gln Lys Leu Ser
            1115                1120                1125

Arg Ala Lys Thr Gln Ile Asn Ser Gln Leu Arg Pro Met Met Ser
            1130                1135                1140
```

```
Glu Leu Glu Glu Arg Ala Arg Gln Gln Arg Gly His Leu His Leu
    1145                1150                1155

Leu Glu Thr Ser Ile Asp Gly Ile Leu Ala Asp Val Lys Asn Leu
    1160                1165                1170

Glu Asn Ile Arg Asp Asn Leu Pro Pro Gly Cys Tyr Asn Thr Gln
    1175                1180                1185

Ala Leu Glu Gln Gln
    1190

<210> SEQ ID NO 6
<211> LENGTH: 431
<212> TYPE: PRT
<213> ORGANISM: Artificial sequence
<220> FEATURE:
<223> OTHER INFORMATION: Urokinase-type plasminogen activator (PLAU)

<400> SEQUENCE: 6

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Ile Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300
```

```
Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
            325                 330                 335

Val Lys Leu Ile Ser His Arg Glu Cys Gln Gln Pro His Tyr Tyr Gly
        340                 345                 350

Ser Glu Val Thr Thr Lys Met Leu Cys Ala Ala Asp Pro Gln Trp Lys
    355                 360                 365

Thr Asp Ser Cys Gln Gly Asp Ser Gly Gly Pro Leu Val Cys Ser Leu
370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
            405                 410                 415

Pro Trp Ile Arg Ser His Thr Lys Glu Glu Asn Gly Leu Ala Leu
        420                 425                 430
```

```
<210> SEQ ID NO 7
<211> LENGTH: 20
<212> TYPE: DNA
<213> ORGANISM: Artificial sequence
<220> FEATURE:
<223> OTHER INFORMATION: siRNA sequence FSTL1

<400> SEQUENCE: 7
cggatactat tgatgaataa                                              20

<210> SEQ ID NO 8
<211> LENGTH: 20
<212> TYPE: DNA
<213> ORGANISM: Artificial sequence
<220> FEATURE:
<223> OTHER INFORMATION: siRNA sequence LAMC2

<400> SEQUENCE: 8
agaatcctga cattgagtgt                                              20

<210> SEQ ID NO 9
<211> LENGTH: 20
<212> TYPE: DNA
<213> ORGANISM: Artificial sequence
<220> FEATURE:
<223> OTHER INFORMATION: siRNA sequence DIAPH1

<400> SEQUENCE: 9
ctgcatgtga ggagttacgt                                              20

<210> SEQ ID NO 10
<211> LENGTH: 20
<212> TYPE: DNA
<213> ORGANISM: Artificial sequence
<220> FEATURE:
<223> OTHER INFORMATION: siRNA sequence PLAU

<400> SEQUENCE: 10
aattctaccg actatctcta                                              20

<210> SEQ ID NO 11
<211> LENGTH: 62
<212> TYPE: DNA
<213> ORGANISM: Artificial sequence
<220> FEATURE:
<223> OTHER INFORMATION: Sequence of Pre-miR-198 WT probe
```

<400> SEQUENCE: 11
tcattggtcc agaggggaga taggttcctg tgattttttcc ttcttctcta tagaataaat    60
ga    62

<210> SEQ ID NO 12
<211> LENGTH: 62
<212> TYPE: DNA
<213> ORGANISM: Artificial sequence
<220> FEATURE:
<223> OTHER INFORMATION: Sequence of Pre-miR-198 WT probe

<400> SEQUENCE: 12
tcattggtcc agaggggaga taggttcctg tgacccccccc ttcttctcta tagaataaat    60
ga    62

<210> SEQ ID NO 13
<211> LENGTH: 41
<212> TYPE: DNA
<213> ORGANISM: Artificial sequence
<220> FEATURE:
<223> OTHER INFORMATION: Luciferase T7 forward primer (binds 9 base
      pairs upstream of Luciferase AUG in pMIRGLO. Includes the Kozak
      sequence)

<400> SEQUENCE: 13
taatacgact cactataggg aaagccacca tggaagatgc c    41

<210> SEQ ID NO 14
<211> LENGTH: 21
<212> TYPE: DNA
<213> ORGANISM: Artificial sequence
<220> FEATURE:
<223> OTHER INFORMATION: FSTL1 3' UTR reverse primer (Binds to position
      2617 in FSTL1 3'UTR)

<400> SEQUENCE: 14
ccgaaaagga agaatcagga g    21

<210> SEQ ID NO 15
<211> LENGTH: 41
<212> TYPE: DNA
<213> ORGANISM: Artificial sequence
<220> FEATURE:
<223> OTHER INFORMATION: CopGFP start T7F primer

<400> SEQUENCE: 15
taatacgact cactataggg ctagacgcca ccatggagag c    41

<210> SEQ ID NO 16
<211> LENGTH: 22
<212> TYPE: DNA
<213> ORGANISM: Artificial sequence
<220> FEATURE:
<223> OTHER INFORMATION: CopGFP stop R

<400> SEQUENCE: 16
gtcgacttag cgagatccgg tg    22

<210> SEQ ID NO 17
<211> LENGTH: 22
<212> TYPE: RNA
<213> ORGANISM: Artificial sequence
<220> FEATURE:
<223> OTHER INFORMATION: Human microRNA-198 (miRNA-198) - RNA sequence -continued

```
<400> SEQUENCE: 17
gguccagagg ggagauaggu uc                                              22

<210> SEQ ID NO 18
<211> LENGTH: 8
<212> TYPE: RNA
<213> ORGANISM: Artificial sequence
<220> FEATURE:
<223> OTHER INFORMATION: Human microRNA-198 (miRNA-198)  - Seed sequence

<400> SEQUENCE: 18 guccagag                                                               8

<210> SEQ ID NO 19
<211> LENGTH: 62
<212> TYPE: DNA
<213> ORGANISM: Artificial sequence
<220> FEATURE:
<223> OTHER INFORMATION: Pre-miR-198 WT

<400> SEQUENCE: 19
tcattggtcc agaggggaga taggttcctg tgattttcc ttcttctcta tagaataaat       60
ga                                                                    62

<210> SEQ ID NO 20
<211> LENGTH: 62
<212> TYPE: DNA
<213> ORGANISM: Artificial sequence
<220> FEATURE:
<223> OTHER INFORMATION: Pre-miR-198 Mut

<400> SEQUENCE: 20
tcattggtcc agaggggaga taggttcctg tgacccccc ttcttctcta tagaataaat       60
ga                                                                    62
```